US012194261B2

(12) United States Patent
Noyes

(10) Patent No.: US 12,194,261 B2
(45) Date of Patent: Jan. 14, 2025

(54) ENDOSCOPIC BALLOON DILATOR SYSTEMS

(71) Applicant: ResnENT, LLC, Bloomington, IL (US)

(72) Inventor: Willard S. Noyes, Bloomington, IL (US)

(73) Assignee: RESNENT, LLC, Bloomington, IL (US)

( * ) Notice: Subject to any disclaimer, the term of this patent is extended or adjusted under 35 U.S.C. 154(b) by 635 days.

(21) Appl. No.: 17/330,210

(22) Filed: May 25, 2021

(65) Prior Publication Data

US 2022/0184359 A1    Jun. 16, 2022

Related U.S. Application Data

(63) Continuation of application No. 17/181,925, filed on Feb. 22, 2021, which is a continuation-in-part of
(Continued)

(51) Int. Cl.
*A61B 1/00* (2006.01)
*A61M 16/04* (2006.01)
(Continued)

(52) U.S. Cl.
CPC ........ *A61M 29/02* (2013.01); *A61M 16/0461* (2013.01); *A61M 16/0465* (2013.01);
(Continued)

(58) Field of Classification Search
CPC .. A61B 1/0125; A61B 1/00135; A61M 29/02; A61M 16/0461; A61M 16/0465;
(Continued)

(56) References Cited

U.S. PATENT DOCUMENTS 3,087,493 A    4/1963  Schossow
3,810,474 A *  5/1974  Cross ................ A61M 16/0443
                                            128/207.15
(Continued)

FOREIGN PATENT DOCUMENTS

EP    1547641    6/2005
EP    1626764    2/2006
(Continued)

OTHER PUBLICATIONS

Australian Examination Report No. 1 dated Nov. 25, 2022 for Australian Application No. 2018255426.
(Continued)

*Primary Examiner* — Anh Tuam T Nguyen
*Assistant Examiner* — Rynae E Boler
(74) *Attorney, Agent, or Firm* — Sheppard, Mullin, Richter & Hampton LLP

(57) ABSTRACT

Some implementations of the disclosure are directed to a balloon dilator system, including: a balloon pump hand piece configured to pump pressurized fluid through a flexible tube to inflate an inflatable balloon, the balloon pump hand piece comprising: an attachment mechanism for removably coupling the balloon pump hand piece to a proximal end of an endoscope; the flexible tube, wherein the flexible tube is configured to be in fluid communication with the balloon pump hand piece at a first end of the flexible tube, and the inflatable balloon at a second end of the flexible tube; a hollow inner cannula; and the inflatable balloon, wherein the inflatable balloon is external to and circumferentially attached to the hollow inner cannula between the proximal end of the hollow inner cannula and the distal end of the hollow inner cannula.

19 Claims, 50 Drawing Sheets

Related U.S. Application Data application No. 16/664,723, filed on Oct. 25, 2019, now Pat. No. 10,925,467, which is a continuation-in-part of application No. 15/958,351, filed on Apr. 20, 2018, now Pat. No. 10,512,391.

(60) Provisional application No. 62/633,540, filed on Feb. 21, 2018, provisional application No. 62/487,903, filed on Apr. 20, 2017.

(51) Int. Cl.
    *A61M 25/10*    (2013.01)
    *A61M 29/02*    (2006.01)

(52) U.S. Cl.
    CPC ... *A61M 25/1018* (2013.01); *A61M 2029/025* (2013.01); *A61M 2210/1032* (2013.01); *A61M 2210/105* (2013.01)

(58) Field of Classification Search
    CPC ........ A61M 25/1018; A61M 2029/025; A61M 2210/1032; A61M 2210/105; A61M 16/0463; A61M 16/0472
    See application file for complete search history.

(56) References Cited

U.S. PATENT DOCUMENTS

| | | | |
|---|---|---|---|
| 3,889,688 A * | 6/1975 | Eamkaow | A61M 16/0486 128/207.15 |
| 4,459,984 A * | 7/1984 | Liegner | A61M 16/0465 128/207.15 |
| 5,005,943 A | 4/1991 | Fort | |
| 5,653,230 A * | 8/1997 | Ciaglia | A61M 16/0431 128/200.26 |
| 5,921,917 A * | 7/1999 | Barthel | A61B 1/07 128/200.26 |
| 6,706,017 B1 * | 3/2004 | Dulguerov | A61M 16/085 128/207.29 |
| 8,414,476 B2 | 4/2013 | Jenkins et al. | |
| 9,011,412 B2 | 4/2015 | Albritton, IV et al. | |
| 9,161,769 B2 | 10/2015 | Stoddard et al. | |
| 9,655,639 B2 | 5/2017 | Mark | |
| 10,137,285 B2 | 11/2018 | Jenkins et al. | |
| 10,639,462 B2 | 5/2020 | Matlock et al. | |
| 2002/0161280 A1 | 10/2002 | Chatenever et al. | |
| 2004/0034369 A1 | 2/2004 | Sauer et al. | |
| 2004/0230157 A1 * | 11/2004 | Perry | A61M 5/14566 604/99.02 |
| 2004/0255954 A1 * | 12/2004 | Zgoda | A61M 16/0445 128/207.29 |
| 2005/0234297 A1 | 10/2005 | Devierre et al. | |
| 2006/0015012 A1 | 1/2006 | Sato | |
| 2007/0276183 A1 | 11/2007 | Melder | |
| 2008/0147018 A1 | 6/2008 | Squilla et al. | |
| 2009/0131785 A1 | 5/2009 | Lee et al. | |
| 2010/0012130 A1 | 1/2010 | Guerra | |
| 2010/0125165 A1 | 5/2010 | Torii et al. | |
| 2011/0028785 A1 | 2/2011 | Chen | |
| 2011/0290245 A1 * | 12/2011 | Cuevas | A61M 29/02 128/200.26 |
| 2012/0180787 A1 * | 7/2012 | Bosel | A61M 16/0459 128/200.26 |
| 2013/0006287 A1 | 1/2013 | West et al. | |
| 2013/0096378 A1 * | 4/2013 | Alexander | A61B 1/00114 606/191 |
| 2014/0128902 A1 * | 5/2014 | Guerra | A61M 16/0472 606/196 |
| 2014/0375784 A1 | 12/2014 | Massetti | |
| 2015/0119923 A1 | 4/2015 | Liberatore et al. | |
| 2016/0067465 A1 | 3/2016 | Gerrans et al. | |
| 2016/0106300 A1 | 4/2016 | Noyes | |
| 2016/0198936 A1 | 7/2016 | Sueyasu et al. | |
| 2016/0278626 A1 * | 9/2016 | Cornhill | A61M 25/1011 |
| 2016/0287851 A1 | 10/2016 | Ha et al. | |
| 2016/0310647 A1 | 10/2016 | Jenkins et al. | |
| 2017/0065155 A1 | 3/2017 | Farhadi | |
| 2017/0143188 A1 | 5/2017 | Oskin et al. | |
| 2017/0215706 A1 | 8/2017 | Harrah et al. | |
| 2017/0293139 A1 | 10/2017 | Rehe | |
| 2018/0008138 A1 * | 1/2018 | Thommen | A61B 1/051 |
| 2018/0256009 A1 | 9/2018 | Ouyang | |
| 2018/0303314 A1 | 10/2018 | Noyes | |
| 2018/0326144 A1 | 11/2018 | Truckai | |
| 2019/0313881 A1 | 10/2019 | Francher | |
| 2019/0374095 A1 | 12/2019 | Lord et al. | |

FOREIGN PATENT DOCUMENTS

| | | |
|---|---|---|
| EP | 1726248 | 11/2006 |
| EP | 1736094 | 12/2006 |
| EP | 1929929 | 6/2008 |
| EP | 2522272 | 11/2012 |
| EP | 2594189 | 5/2013 |
| EP | 3146927 | 3/2017 |
| JP | S63-230163 A | 9/1988 |
| JP | 2013-106712 | 6/2013 |
| WO | WO 1994/015522 | 7/1994 |
| WO | WO 2010/027109 | 3/2010 |
| WO | WO 2011/070845 | 6/2011 |
| WO | WO 2018/064343 | 4/2018 |

OTHER PUBLICATIONS

European Examination Report dated Dec. 2, 2022 for European Application No. EP 21207854.7.

European Examination Report dated Dec. 22, 2022 for European Application No. EP 21207855.4.

International Search Report and Written Opinion dated Jul. 6, 2018 in International Application No. PCT/US2018/028663, filed Apr. 20, 2018.

International Search Report and Written Opinion mailed Feb. 23, 2021 for International Application No. PCT/US2020/056128, filed Oct. 16, 2020.

Witt et al., "Types of Sialendoscopes and Accessories-Diagnostic Sialendoscopy: Polydiagnost Modular Endoscope," Surgery of the Salivary Glands (2021), 7 pages.

Office Action issued Sep. 6, 2022 for Japanese Application No. 2021-149888.

Extended European Search Report dated Feb. 9, 2022 for European Application No. 21207854.7.

Extended European Search Report dated Feb. 9, 2022 for European Application No. 21207855.4.

Communication pursuant to Article 94(3) EPC dated Apr. 19, 2023 for European Application No. 21207854.7.

Examination Report—Communication pursuant to Article 94(3) EPC dated Nov. 8, 2023 for European Application No. 21207854.7.

Non-final Office Action dated Dec. 21, 2023 for U.S. Appl. No. 17/181,925.

Office Action dated Feb. 27, 2024 for Canadian Application No. 3,060,092.

Notification of Reasons for Refusal dated Jul. 9, 2024 for Japanese Application No. 2023-110381.

* cited by examiner

ENDOSCOPIC BALLOON DILATOR SYSTEMS

CROSS-REFERENCE TO RELATED APPLICATIONS

This application is a continuation of and claims priority to U.S. patent application Ser. No. 17/181,925 filed Feb. 22, 2021, titled "ENDOSCOPIC BALLOON DILATOR SYSTEMS," and issued as U.S. Pat. No. 12,083,300 on Sep. 10, 2024, which is a continuation-in-part of and claims priority to U.S. patent application Ser. No. 16/664,723 filed Oct. 25, 2019, titled "Portable Endoscope System," and issued as U.S. Pat. No. 10,925,467 on Feb. 23, 2021, which is a continuation-in-part of and claims priority to U.S. patent application Ser. No. 15/958,351 filed Apr. 20, 2018, titled "Flexible-Rigid Hybrid Endoscope And Instrument Attachments," and issued as U.S. Pat. No. 10,512,391 on Dec. 24, 2019, which claims the benefit of U.S. Provisional Patent Application No. 62/487,903 filed Apr. 20, 2017 and titled "Flexible-Rigid Hybrid Endoscope and Instrument Attachment Examples," and U.S. Provisional Patent Application No. 62/633,540 filed Feb. 21, 2018 and titled "Flexible-Rigid Hybrid Endoscope and Instrument Attachment." All of the above-mentioned applications are incorporated herein by reference in their entirety.

BACKGROUND

Endoscopes are illuminated tubular instruments with eyepieces or cameras that are used to look inside a body cavity in procedures called an endoscopy. During performance of a medical procedure with an instrument that is inserted within a patient's body cavity, endoscopes may be used to visualize the medical instrument and body cavity during the procedure. For example, the endoscope may be used to allow the physician to view tissue or other matter within a cavity in a patient while using suction or grasping forceps to remove tissue from the cavity.

In procedures that utilize medical instruments in combination with endoscopes, the endoscope is typically a rigid or flexible tool that is manipulated separately from the medical instrument. During the procedure, medical personnel hold and guide the endoscope with one hand and the instrument used to treat the patient with the other hand. Such endoscopes may either be rigid or flexible.

Current implementations of rigid endoscopes have significant limitations with respect to visualizing the patient's body cavity during a procedure. For example, current implementations of rigid nasal endoscopes do not allow for direct visualization of the removal of hard to reach sinus tissue or cauterization of hard to reach bleeding sites. The rigid endoscope cannot be inserted directly into the frontal sinuses or gain proper visualization of the medial inferior maxillary sinus cavity. Removing laryngeal tissue and foreign bodies as well as tissue in patients with nasopharyngeal stenosis is also difficult because of inadequate visualization and difficulty in reaching desired anatomical sites. Further, angled rigid scope visualization often distorts the surgeon's perspective and is cumbersome to use in conjunction with secondary instruments such as forceps in a small cavity.

As a result, ear, nose, throat (ENT) physicians are typically unable to directly visualize removal of all maxillary sinus tissue during endoscopic sinus procedures. The surgeon is often handicapped by the rigidity of the endoscope and the angle of visualization when trying to perform tasks in areas difficult to reach with sinus instruments. The surgeon is handicapped even with the available angled rigid scope visualization. In addition, especially in pediatric cases, there is simply not enough room to insert multiple instruments in a nasal passage or sinus opening at the same time.

Likewise, current implementations of flexible endoscopes present their own set of problems. In some current flexible endoscopic systems on the market, a tool is required to be threaded through a tiny instrument channel incorporated within the length of a flexible endoscope. In such systems, the size of the tool is limited to the diameter of the endoscopic channel, and thus greatly limits the tool options available for endoscopic tissue manipulation. For example, while the typical ear, nose, throat (ENT) flexible nasopharyngoscope may be used to visualize around corners in body cavities, it does not have a channel for accommodating a grasping forceps, laser, balloon, cautery, or other appropriately sized surgical tool.

Conversely, trying to thread a thin flexible endoscope through a channel attached to the outside of a larger instrument or shaft is difficult. Flexible endoscopes used for this purpose are typically long and thin with fragile fibers. They are difficult to stabilize, hang off the back of the instrument, and do not connect or transfer easily from one instrument to another. Use of currently available flexible endoscopes requires two hands: one hand to manipulate the tip flexion and another hand to stabilize the tip at the nostril. For example, current, in-office methods for trans-oral laryngeal injection of Botox and/or Radeisse® hydroxyl-appetite paste are cumbersome. They require a flexible nasopharyngoscope in the nose and a separate needle injector to be manipulated simultaneously through the mouth in a manner that is unmanageable by the physician and uncomfortable to the patient. If a physician wants to biopsy, cauterize, or inject under flexible endoscope guidance, the hand at the nostril must be released in order to work the second instrument, balloon, cautery, or suction.

SUMMARY

Implementations described herein are directed to an improved flexible-rigid hybrid design for an endoscope and attachment mechanisms for removably coupling and decoupling the endoscope to a handle portion and/or a tool portion of a variety of different instruments. Further implementations described herein are directed to designs for instruments that may be coupled to the flexible-rigid endoscope described herein or other endoscopes. Further implementations described herein are directed to a lightweight and flexible endoscope system design including an endoscope that removably couples to a control box using a cable connector.

In one embodiment, an endoscope includes: a rigid proximal end, the rigid proximal end including: a rigid proximal attachment segment to removably couple the endoscope to a handle portion of an instrument; and a distal flexible end to be inserted in a patient cavity to image the cavity. In some instances, the endoscope may include a tapered transition between the rigid proximal end and the flexible distal end.

In some implementations, metal bands may be spaced along a length of the distal flexible segment. The metal bands may be to protect the distal flexible segment and/or magnetically couple the distal flexible segment to a tool portion of an instrument.

In some implementations, the rigid proximal end includes the rigid proximal attachment segment and a distal non-attachment segment. The rigid proximal attachment segment may include multiple longitudinally spaced slots to removably couple the endoscope to an instrument, wherein the slots are to be inserted into ridges of an attachment mechanism of an instrument. The rigid proximal attachment segment may also include multiple longitudinal grooves to removably couple the endoscope to an instrument. In some implementations, the rigid proximal attachment segment has a rectangular or circular cross section.

In some implementations, the proximal attachment segment includes a twist-lock mechanism including one or more projections to removably couple the endoscope to an instrument.

In implementations, the endoscope may include: a lens and light emitter positioned at a tip of the distal flexible end, the light emitter to illuminate a cavity, and the lens to collect light reflected by the cavity; and an eye piece or camera assembly coupled to the rigid proximal end.

In implementations, the endoscope may include: a housing proximal to the rigid proximal end, the housing including an illumination device (e.g., one or more LEDs); and a connector proximal to the housing, the connector to removably couple to a connector cable that connects the endoscope to a control box, where the control box includes one or more of: a battery pack, an image sensor, and a WIFI module.

In some implementations, the rigid proximal end has a longitudinal length between 10 cm and 20 cm, and a thickness between 0.5 cm and 2 cm; and the flexible distal end has a longitudinal length between 2.5 cm and 15 cm, and a thickness between 1 mm and 4 mm.

In another embodiment, an endoscope system includes: an endoscope including: a distal flexible end and a rigid proximal end; and an instrument to removably couple to the endoscope at both the rigid proximal end and the distal flexible end of the endoscope. In this embodiment, the rigid proximal end of the endoscope may be to removably couple to a handle portion of the instrument, and the distal flexible end of the endoscope may be to removably couple to a tool portion of the instrument. For example, the handle portion of the instrument may include the various means described herein for removably coupling the handle portion to the rigid proximal end, and/or the tool portion of the instrument may include the various means described herein for removably coupling the handle portion to the rigid proximal end.

In some implementations, the instrument includes a channel housing located above an actuating portion of the handle portion of the instrument, the housing including a depressible button that actuates a retractable interior protuberance that engages one or more longitudinally spaced slots on the rigid proximal end of the endoscope.

In some implementations, the rigid proximal end includes longitudinally spaced slots and at least one longitudinal groove, and the handle portion of the instrument includes an elongated channel having spaced ridges to align with the longitudinally spaced slots and a retractable interior bar to engage the longitudinal groove.

In some implementations, the rigid proximal end of the endoscope includes a proximal attachment segment that includes a twist-lock mechanism, the twist-lock mechanism including one or more projections, and the instrument includes a slotted instrument channel that receives the projections.

In some implementations, the tool portion of the instrument includes loops that engage the distal flexible end of the flexible-rigid hybrid endoscope.

In some implementations, the distal flexible end includes metallic or magnetic bands spaced along a length of the distal flexible end, and the tool portion of the instrument includes an instrument shaft having a metallic or magnetized segment that magnetically couples to the metal bands.

In some implementations, the tool portion of the instrument includes an instrument shaft having a series of clips that attach to the distal flexible end.

In some implementations, the tool portion of the instrument includes one or more elongated tubes spaced along a distal shaft of the instrument through which the distal flexible end of the endoscope is inserted.

In some implementations, the endoscope system further includes: a removable insert having first and second channel grooves, where the first channel groove attaches to an instrument shaft of the instrument and the second channel groove attaches to the distal flexible end of the endoscope. In particular implementations, the removable insert further includes one or more hollow channels configured for the delivery of at least one of suction or irrigation.

In some implementations, the instrument is a syringe gun including a gun handle, syringe, and injection needle; and the rigid proximal end of the endoscope is to removably couple to a top portion of the gun handle.

In some implementations, the instrument is a Eustachian tube dilator including a hollow tubing balloon cannula, and the distal flexible end of the endoscope is to removably couple to a distal portion of the hollow balloon cannula.

In some implementations, wherein the instrument is a balloon dilator, and the rigid proximal end of the endoscope is removably coupled to a balloon pump hand piece of the instrument.

In some implementations, the instrument is an endoscopic trans-oral or trans-nasal esophageal balloon dilator including: a hand piece, and a hollow tube extending from the hand piece, the hollow tube to receive a balloon catheter, where the rigid proximal end of the endoscope is to removably couple to the hand piece.

In one embodiment, an endoscope system, includes: an endoscope and a portable control box that may removably couple to the endoscope using a cable connector. The endoscope of this system may include: a distal flexible end; a rigid proximal end; a housing proximal to the rigid proximal end, the housing including an illumination device; and a connector to removably couple to a first end of the cable connector. The portable control box of this system may couple to a second end of the cable connector and it may include: a power source to power the endoscope; an image sensor to collect light captured by the endoscope; and a network interface.

Other features and aspects of the disclosed technology will become apparent from the following detailed description, taken in conjunction with the accompanying drawings, which illustrate, by way of example, the features in accordance with implementations of the disclosed technology. The summary is not intended to limit the scope of any inventions described herein, which are defined by the claims and equivalents.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The present disclosure, in accordance with one or more implementations, is described in detail with reference to the following figures. The figures are provided for purposes of illustration only and merely depict example implementations. Furthermore, it should be noted that for clarity and ease of illustration, the elements in the figures have not necessarily been drawn to scale.

Some of the figures included herein illustrate various implementations of the disclosed technology from different viewing angles. Although the accompanying descriptive text may refer to such views as "top," "bottom" or "side" views, such references are merely descriptive and do not imply or require that the disclosed technology be implemented or used in a particular spatial orientation unless explicitly stated otherwise.

Figure 1:
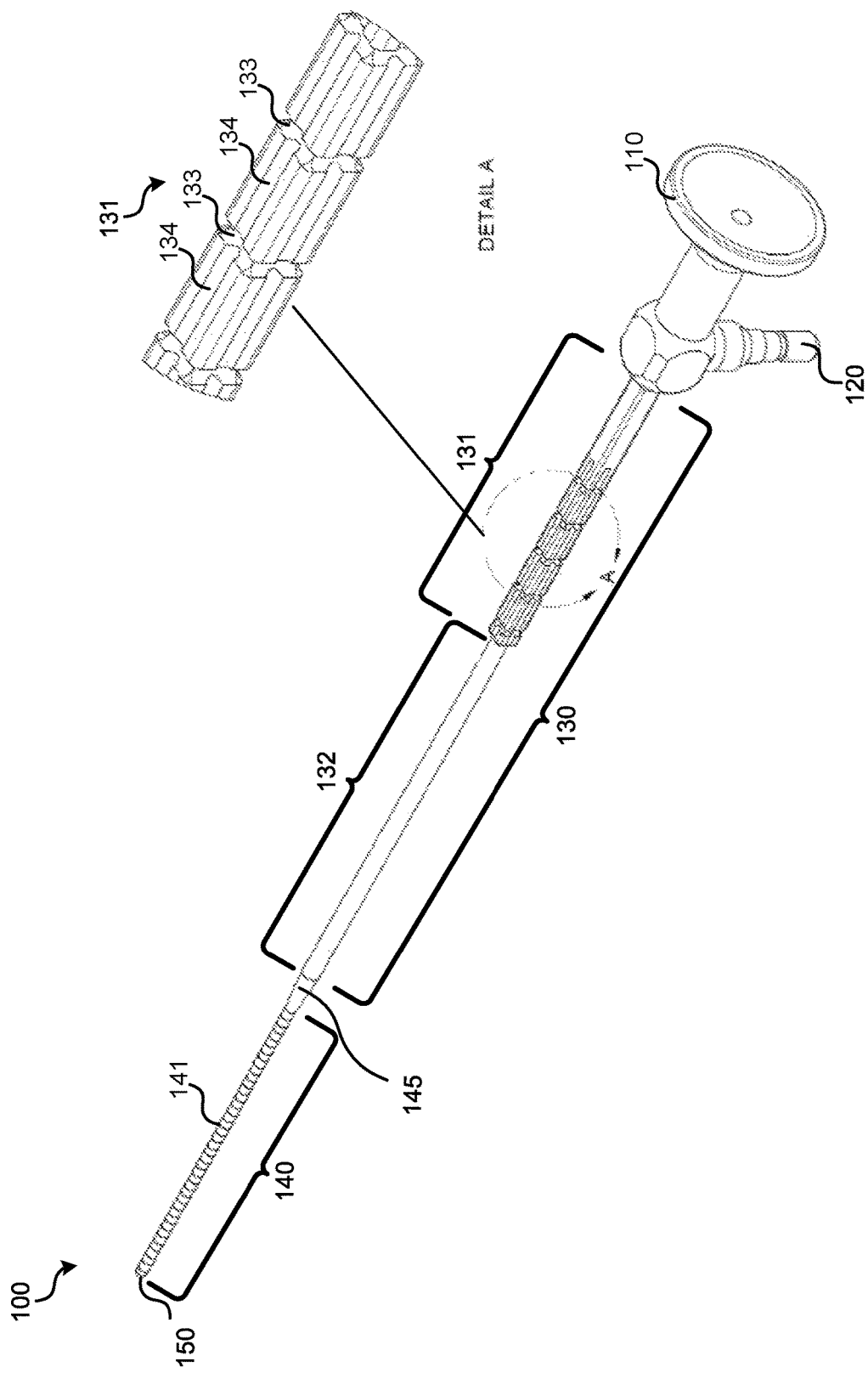
FIG. 1 shows a perspective view of a flexible-rigid hybrid endoscope including a proximal attachment segment that is square, in accordance with implementations.

The figures are not exhaustive and do not limit the present disclosure to the precise form disclosed.

DETAILED DESCRIPTION

As noted above, current implementations of endoscopes have limitations with respect to their usage with other instruments during procedures. Rigid endoscopes cannot be bent to effectively visualize a body cavity of the patient, and flexible endoscopes cannot be effectively stabilized or easily used in combination with another medical instrument. In many cases, it may difficult for the endoscope to visualize the grasping or removing of tissues, and in some hard to reach areas, such a procedure may be done blindly, resulting in incomplete tissue removal. Additionally, it may be cumbersome for the medical practitioner to simultaneously manipulate and position the endoscope and instrument.

To this end, implementations of the disclosure are directed to an improved flexible-rigid hybrid design for an endoscope and simplified mechanisms for removably coupling and decoupling the endoscope to a variety of different instruments. Further implementations described herein are directed to novel designs for instruments that may be coupled to the flexible-rigid endoscope described herein. Such instruments may include laryngeal and sinus forceps, a laryngeal syringe gun, an endoscopic Eustachian tube balloon dilator, an endoscopic tracheal dilator, and an endoscopic trans-oral esophageal balloon dilator.

As will be further appreciated from implementations described below, the endoscope design described herein may provide a variety of advantages to both physicians and patients. For example, by providing a quick, simplified, and reliable mechanism for removably coupling the endoscope to an instrument, the endoscope design described herein may save the physician and patient time. Additionally, the endoscope design described herein may be adapted to be removably coupled to a variety of different instrument types, which may provide additional cost savings and convenience. Further, the design described herein may allow for the physician to use an endoscope with a variety of different instruments in a one-handed manner to facilitate a patient procedure. In some cases, this may eliminate the requirement of having a second medical person to help with the procedure, and may permit more office-based surgeries, which may reduce the cost of various procedures.

Further still, the endoscope design described herein may improve patient comfort by eliminating the need to separately insert an endoscope and instrument in body orifices (e.g., nose or throat) at the same time, and by reducing the overall profile of the inserted instrument and endoscope. Moreover, the endoscope design described herein may improve surgical access, visualization, and instrumentation within conventionally hard to reach anatomic places such as the nasopharynx, frontal sinus, anterior maxillary sinus, tongue base, etc. These and other benefits that may be realized by implementations of the technology described herein may be further appreciated from the below description.

Figure 2:
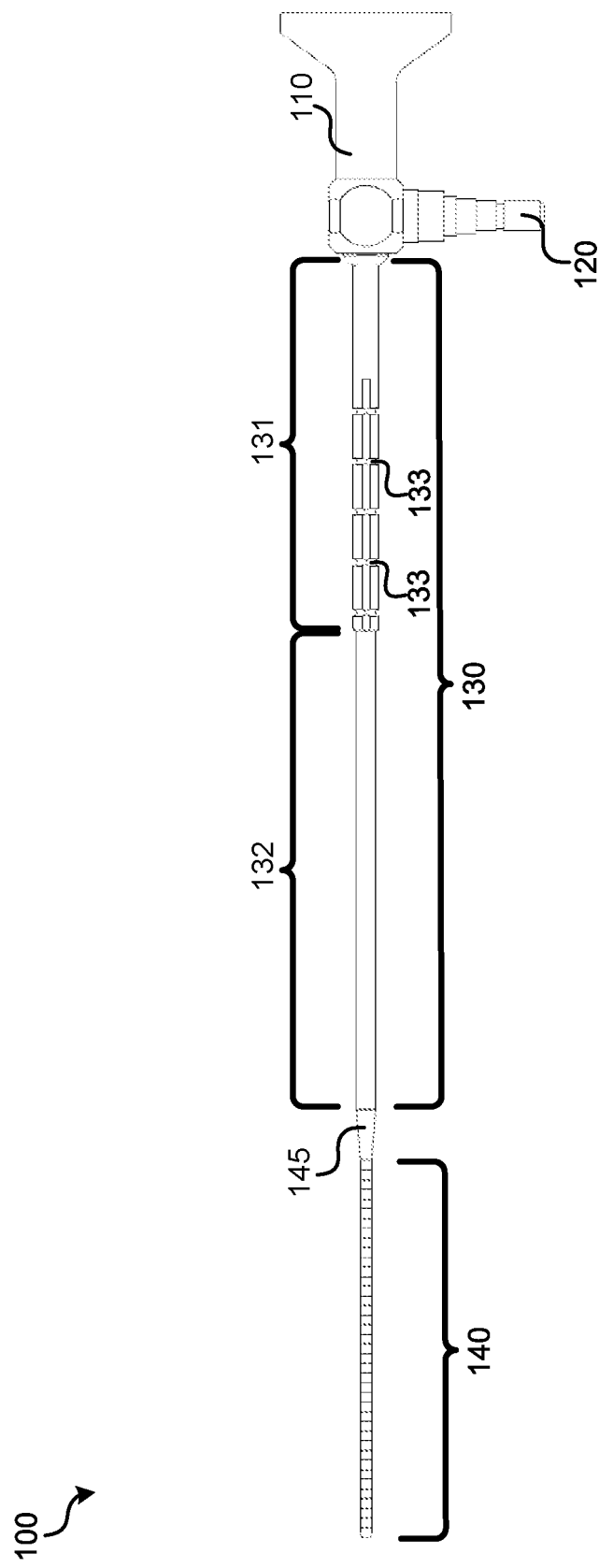
FIG. 2 shows a side view of the flexible-rigid hybrid endoscope of FIG. 1.

FIGS. 1-2 illustrate implementations of a flexible-rigid hybrid endoscope 100 in accordance with the disclosure. As illustrated by FIG. 1, an endoscope 100 may include an eyepiece 110, a connection 120 for a light source, a rigid proximal end 130, a flexible distal end 140, and an objective lens 150 disposed at the end of distal end 140. During operation of endoscope 100, a light source (e.g., a light cable) coupled to connection 120 may emit light that is carried in a distal direction by one or more optical cables (not shown) for emission at a distal end (e.g., end 140) of endoscope 100. For example, the emitted light may illuminate an internal cavity of a patient. Light reflected by the internal cavity of the patient may be collected by objective lens 150 and carried in a proximal direction by one or more optical cables (not shown) to eyepiece 110 and/or a camera to generate an image of the internal cavity. The optical cable(s) used to carry light for emission at the distal end of endoscope 100 and/or the optical cable(s) used to carry light collected from objective lens 150 for image generation at the proximal end of endoscope 100 may be encapsulated or otherwise encased by ends 130 and 140.

In the example of FIG. 1, light is carried back to eye piece 110, which may include controls for adjusting image magnification and/or focus. The eye piece may be coupled to a video camera unit (e.g., a unit including a CCD sensor) that may connect to a display monitor for displaying the generated video. For example, the eye piece of the endoscope may couple to a video camera unit using a suitable adapter. In some implementations, the video camera unit may include a wireless transmitter (e.g., a WIFI transmitter) for wirelessly transmitting any captured video to an external display device. For example, the video camera unit may transmit video to a mobile device for display, a desktop display device, or other suitable display device. In some implementations, a video camera unit may entirely replace eye piece 110. In such implementations, the video camera unit may include controls for adjusting image magnification, orientation, and/or focus. For example, the endoscope may include a rigid or flexible tube that houses a lens system or CCD sensor in lieu of the optical fibers or eyepiece.

In some implementations, one or more light sources may be integrated into endoscope 100 (e.g., in place of connection 120). For instance, the integrated light sources may be configured to emit different wavelengths of light (e.g., red, green, and blue). In some implementations, endoscope 100 may include an integrated power source such as a battery.

Endoscope 100 is rigid at proximal end 130 and flexible at distal end 140. The rigid structure of proximal end 130 may provide stability and facilitated coupling of the endoscope to an instrument. Materials to provide rigidity may include stainless steel, magnetized metals, plastic, ceramic, etc. The flexibility of the distal end 140 may allow for the distal endoscope to bend and conform to the curvatures and angulations of various instrument implementations and anatomical sites. At the junction between the ends is a tapered transition 145, which may be firm and flexible. Transition 145 may help minimize strain and prevent breakage of optical fibers in endoscope 100. In implementations, the tapered transition 145 may be a segment of proximal end 130 or distal end 140.

The length and caliper of the endoscope may vary according to the anatomic site, desired application, and instrument to which it attaches. In particular implementations, the total endoscope length, from eyepiece 110 to the end of distal end 140 may be between 20 and 40 cm. The combined length of ends 130 and 140 that extends from the eyepiece 110 to the distal end may vary depending on the medical application, but for at least some applications may measure between 15 and 35 cm. In particular applications, proximal rigid end 130 may measure between 10 and 20 cm in length and flexible distal end 140 may measure between 4 and 15 cm in length. In one particular implementation, the length of the flexible end 140, including transition 145, is about 8.5 cm and the length of the rigid end 130 is about 15.5 cm. In implementations, proximal rigid end 130 may have a thickness (e.g., diameter) ranging between 0.8 cm and 1.5 cm, and flexible distal end 140 may have a thickness (e.g., diameter) ranging between 1 mm and 4 mm. In particular implementations, tapered transition 145 may measure between 0.5 cm and 1.5 cm in length.

In the example of endoscope 100, rigid proximal end 130 comprises two segments, a rigid proximal attachment segment 131 to removably couple endoscope 100 to an instrument, and a rigid distal segment 132 that transitions to distal end 140 at transition 145. In the example of FIGS. 1-2, proximal attachment segment 131 has a square cross section and longitudinally spaced slots 133 in its surface that may be used to adjust the position (and thus the length) of the endoscope when it is removably coupled to an instrument. For example, if consecutive slots 133 are separated by a distance of 1 cm, then the position endoscope 100 along an attached instrument may be adjusted in intervals of 1 cm. Segment 131 additionally includes grooves 134 that longitudinally run along a surface of segment 131. The combination of grooves 134 and slots 133 may allow a user to configure and secure the endoscope in various circumferential and lengthwise positions when attached to various instrument types and configurations. In some implementations, consecutive slots 133 may be separated by a distance between 0.1 cm and 3.0 cm. In particular implementations, consecutive slots may be separated by a distance between 0.5 cm and 2.0 cm.

Figure 3:
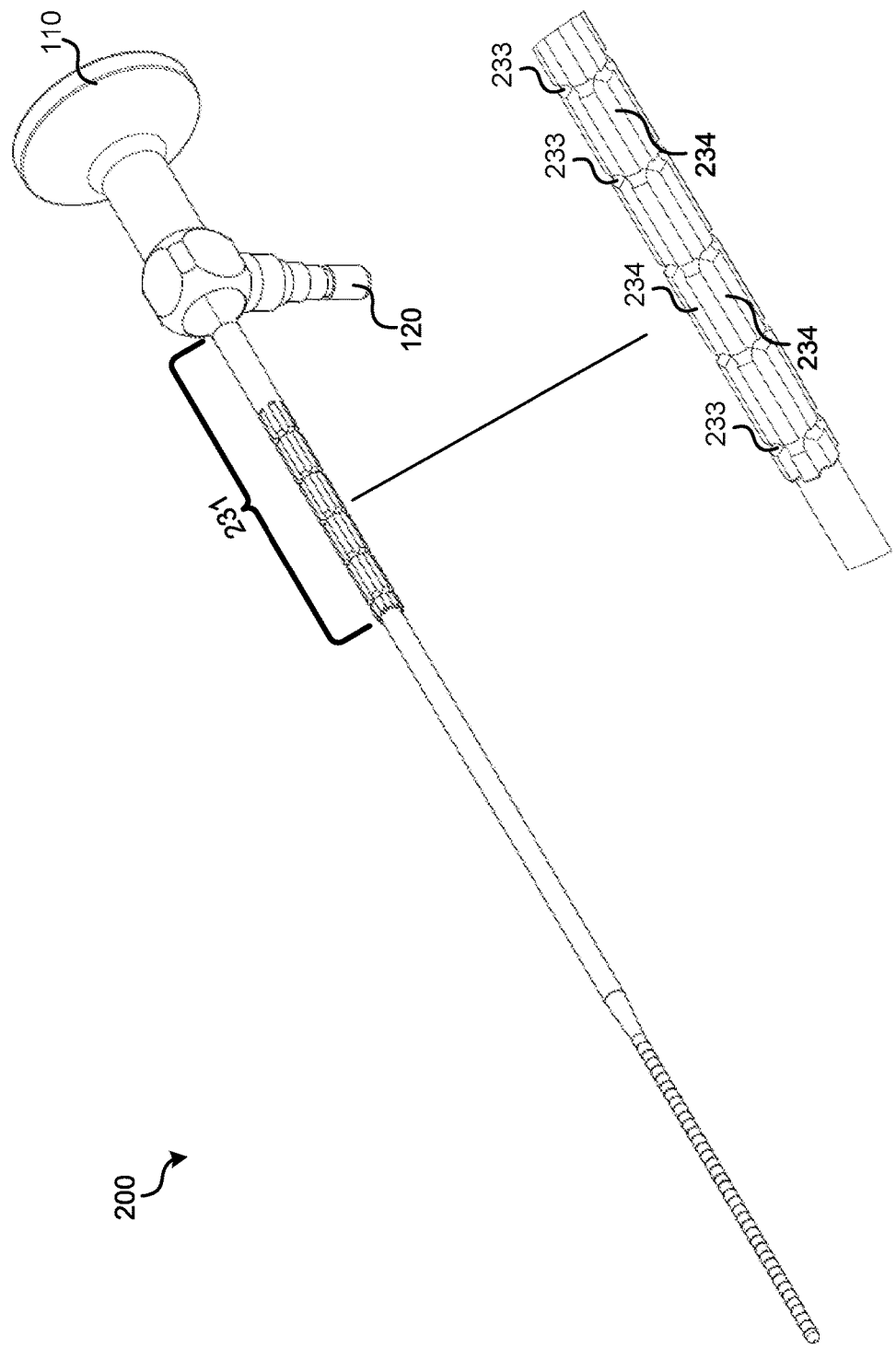
FIG. 3 shows a perspective view of another flexible-rigid hybrid endoscope including a proximal attachment that is circular, in accordance with implementations of the disclosure.

In implementations, the attachment segment may comprise 1 to 12 slots and 1 to 12 grooves. In particular implementations, the attachment segment may comprise 4 to 8 grooves equidistantly spaced around the circumference of the attachment segment. In the example of FIGS. 1-2, attachment segment 131 of endoscope 100 comprises five slots and four grooves equidistantly spaced around the circumference of the attachment segment. FIG. 3 illustrates another example endoscope 200 having a circular attachment segment 231 comprising five spaced slots 233 and six grooves 234 that longitudinally run along a surface of segment 231.

Figure 4:
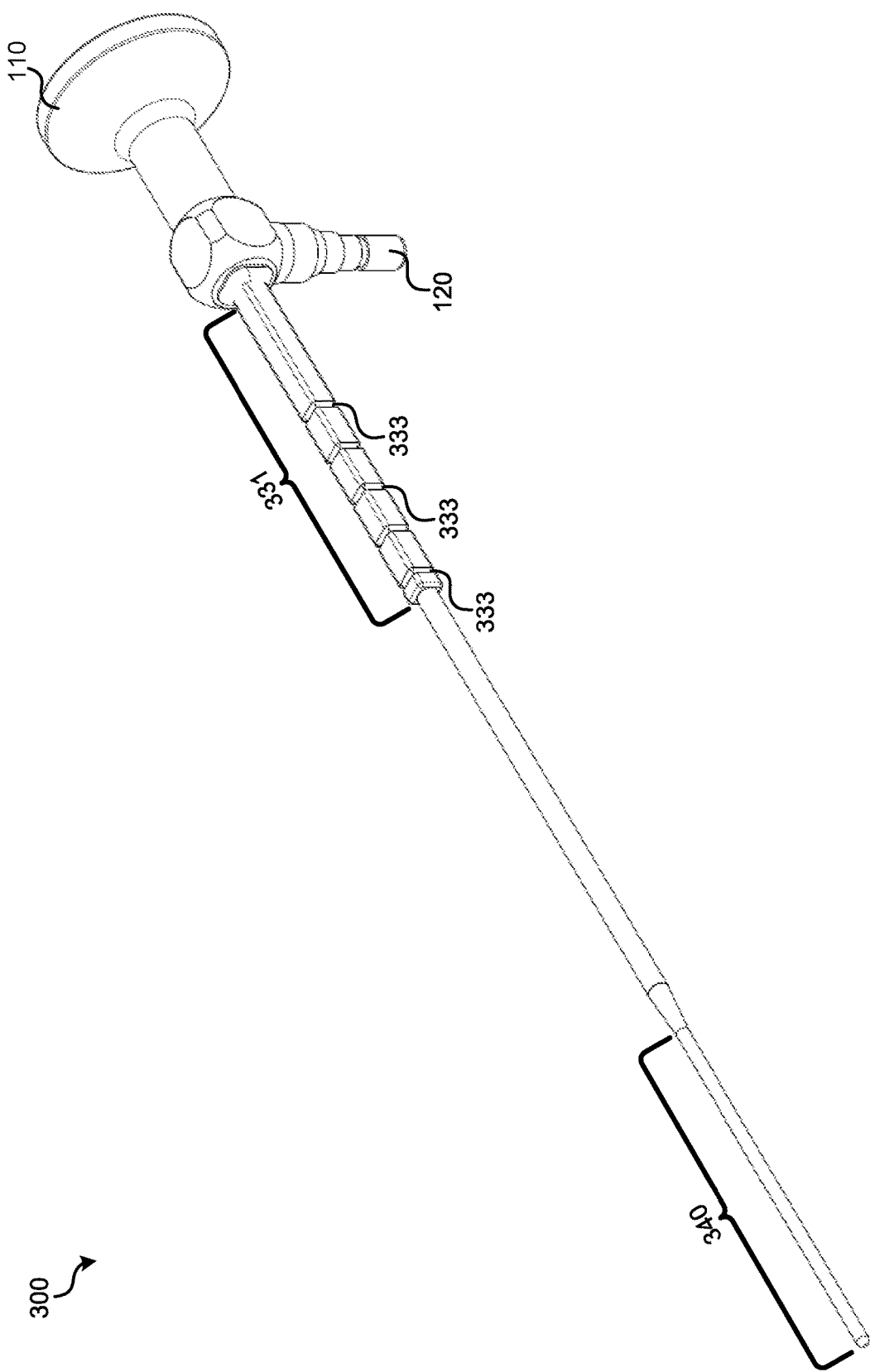
FIG. 4 shows a perspective view of a flexible-rigid hybrid endoscope including a proximal attachment segment that is rectangular, in accordance with implementations of the disclosure.
Figure 5:
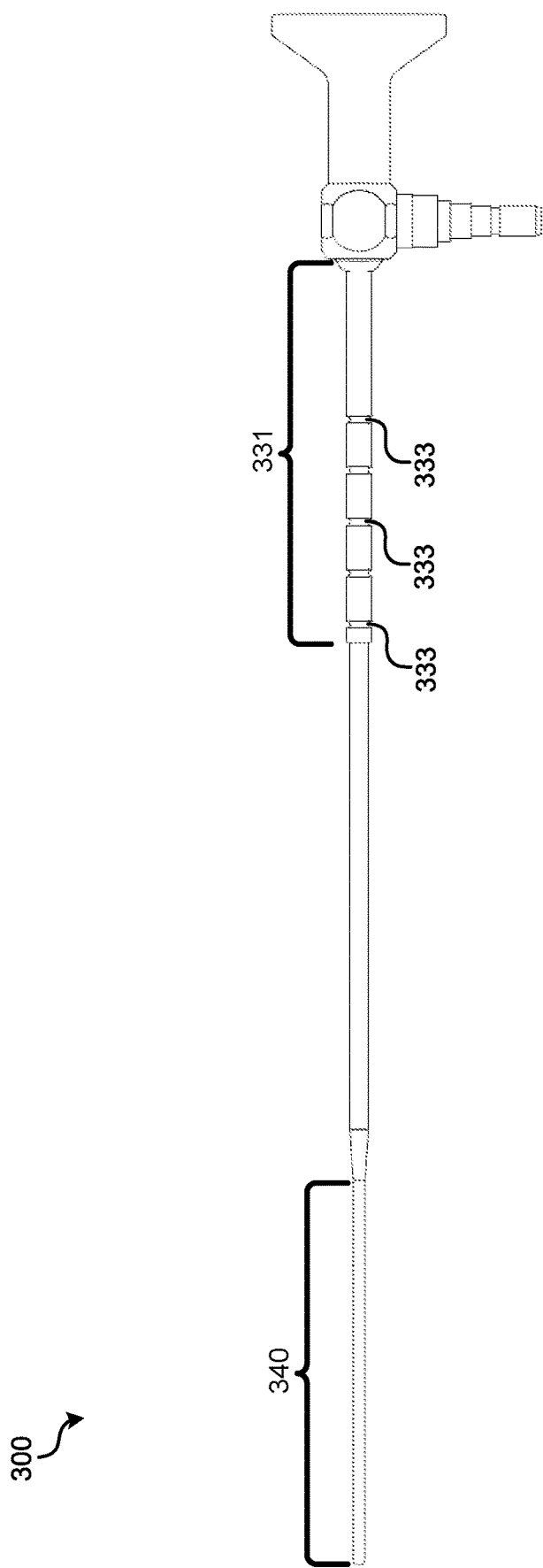
FIG. 5 shows a side view of the flexible-rigid hybrid endoscope of FIG. 4.
Figure 6:
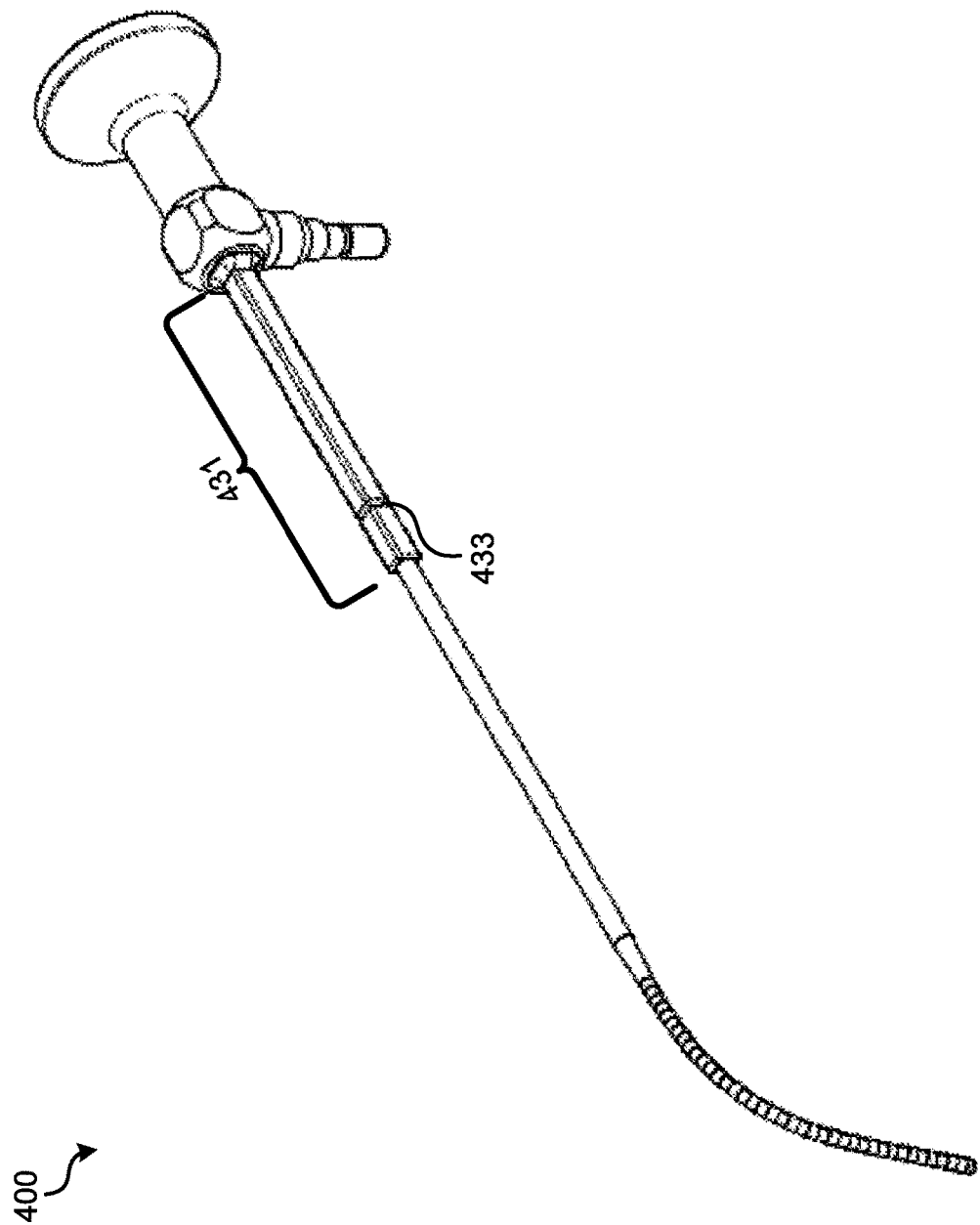
FIG. 6 shows a perspective view of another flexible-rigid hybrid endoscope including a proximal attachment segment that is square, in accordance with implementations of the disclosure.
Figure 7:
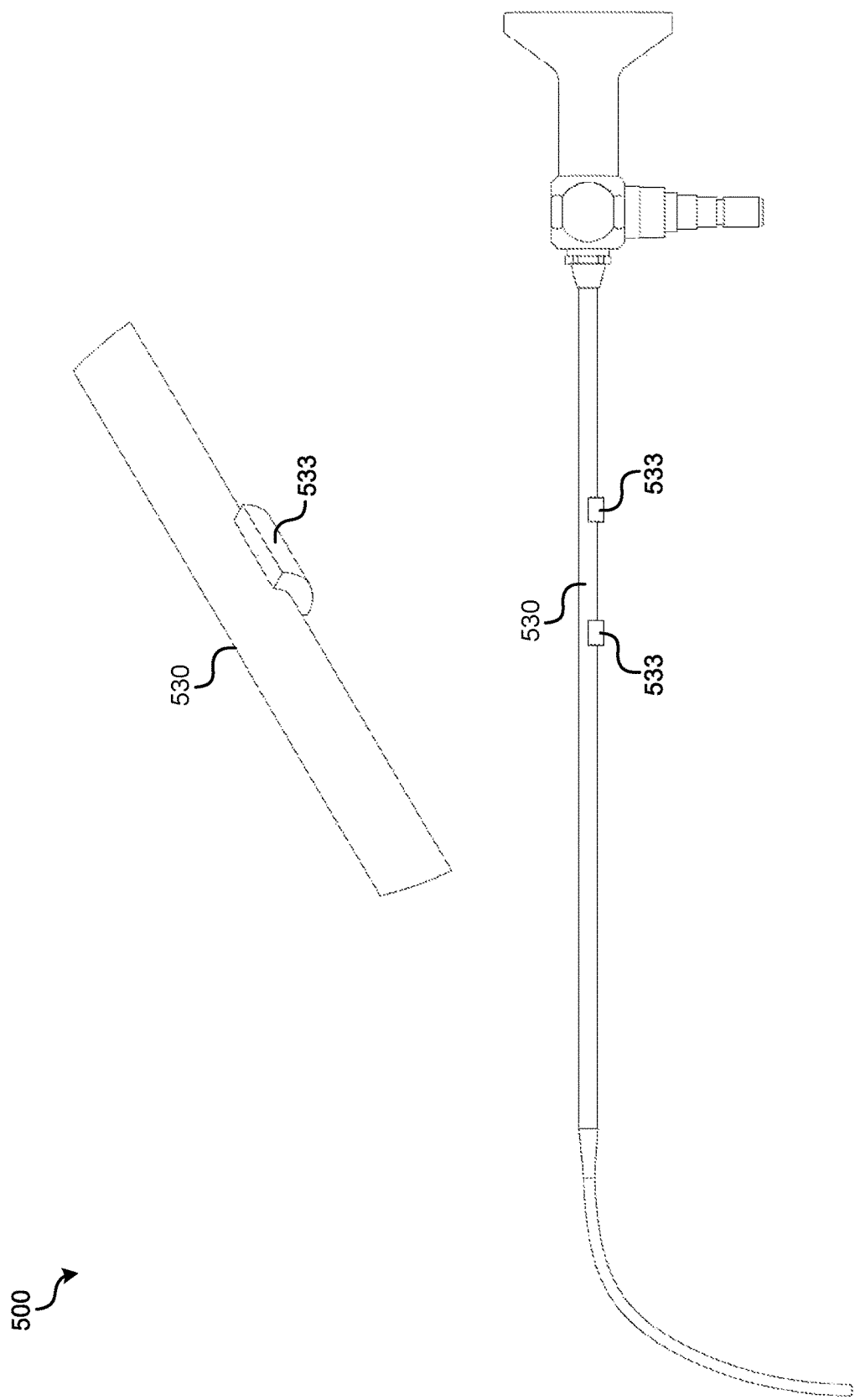
FIG. 7 shows a perspective view of another flexible-rigid hybrid endoscope in accordance with implementations of the disclosure.

Flexible distal end 140 is configured to couple to a distal end of an instrument that is inserted into a cavity (e.g., nose or throat) of a patient. As will be further described below with illustrations, distal end 140 may be suitably flexible to bend and follow the contour of a medical instrument. In the example of endoscope 100, flexible distal end 140 comprises magnetic metal bands 141 spaced along the length of its surface. Magnetic bands 141 may be used to magnetically couple and secure distal end 140 to a distal end of an instrument. Magnetic bands 141 may also add additional reinforcement to distal end 140 to protect any internal optical fibers or components against strain and damage. The magnetic bands may be disposed on distal end 140 such to maintain its flexibility and a maximal bending radius. The bands may be made of a suitable ferromagnetic material such as iron, nickel, cobalt, or an alloy thereof. In other implementations, the surface of distal end 140 may be coated or otherwise covered in a magnetic material that is continuous along the length of end 140. The magnetic material may be suitably flexible and bendable to prevent damage during use. In yet other implementations, distal end 140 may not comprise any magnetic material, but rather metallic bands that couple to magnetic material contained on or within the instrument to which it is attached. Distal end 140 may also be coupled to a distal end of an instrument using some other attachment mechanism, further described below. FIGS. 4-5 illustrate one such example distal end 340 of an endoscope 300 that does not include a magnetic material.

In various implementations, a protective external flexible sheathing (not shown) may cover flexible distal end 140. The sheathing may be sterilized prior to a medical procedure, as is required for use. In implementations where flexible distal end 140 comprises a magnetic material along its surface (e.g., magnetic bands 141), the sheathing may cover the magnetic material, and the magnetic field created by the magnetic material may be sufficiently strong through the sheathing to couple and secure distal end 140 to a distal end of an instrument. In some implementations, the sheathing itself may be a magnetic flexible sheathing configured to magnetically couple the endoscope to a tool portion of an instrument.

Figure 69:
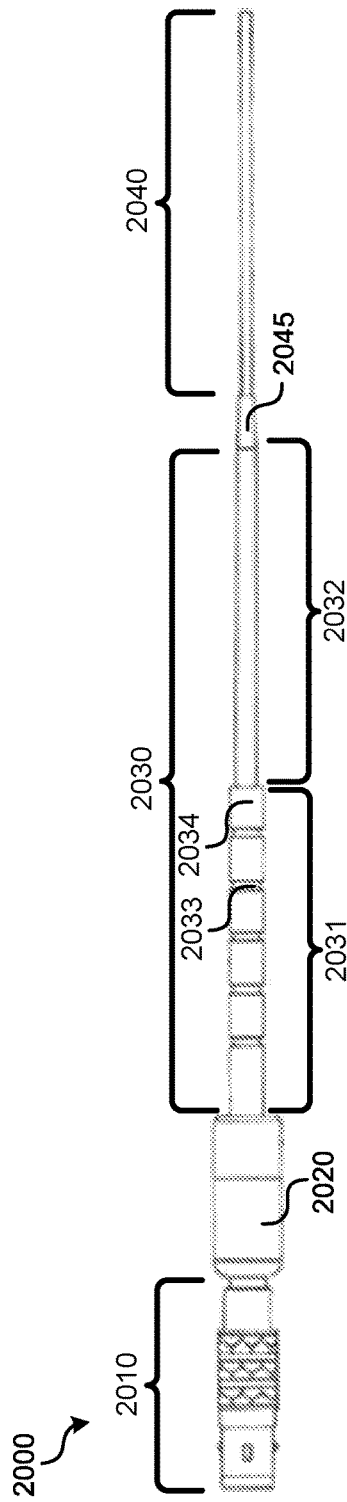
FIG. 69 shows a side view of a charged coupled device flexible-rigid hybrid endoscope, in accordance with implementations.

FIG. 69 shows a side view of a charged coupled device (CCD) flexible-rigid hybrid endoscope 2000, in accordance with implementations. Endoscope 2000 includes a rigid proximal end 2030, and flexible distal end 2040. Rigid proximal end 2030 includes a rigid proximal attachment segment 2031 to removably couple endoscope 2000 to an instrument, and a rigid distal segment 2032 that transitions to flexible distal end 2040 at transition 2045. Rigid proximal attachment segment 2031 includes a square cross section and longitudinally spaced slots 2033 in its surface that may be used to adjust the position (and thus the length) of the endoscope when it is removably coupled to an instrument. Segment 2031 additionally includes grooves 2034 that longitudinally run along a surface of segment 2031.

Figure 70:
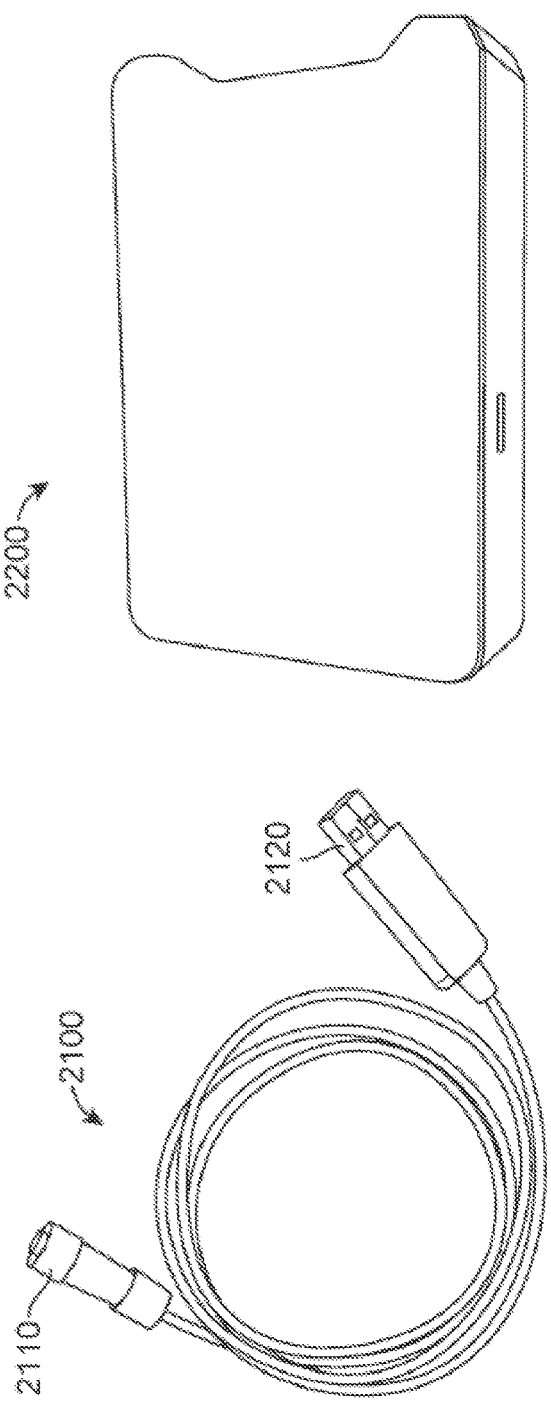
FIG. 70 shows a cable that may be detachably coupled to the endoscope of FIG. 69 and a portable control box that may be communicatively coupled to the endoscope using the detachable cable, in accordance with implementations.

At its proximal end, endoscope 2030 implements a housing 2020 that may incorporate an illumination device (e.g., a LED module), and connector 2010 that may be removably coupled to endoscope 2030 to couple it to a control box. By way of example, FIG. 70 shows a portable control box 2200 that may couple to connector 2010 of endoscope 2000 using connector cable 2100. In the illustrated example, connector 2010 is a female ODU cable, the end 2110 of connector cable 2100 is a male ODU cable to couple to connector 2010, and the end 2120 of connector cable 2100 is a male USB cable to couple to control box 2200. However, it should be appreciated that various suitable connector types (e.g., suitable to transfer high resolution image data in real-time) may be used to couple endoscope 2000 to control box 2200. For example USB 3.x connectors, USB TYPE-C connectors, THUNDERBOLT connectors, HDMI 1.x or 2.x connectors, etc. may be used. In implementations, the length of connector cable 2100 may be tailored based on factors such as ergonomics, the relative positions of control box 2200 and endoscope 2000, etc. For example, connector cable 2100 may be 1 meter long, 2 meters long, 3 meters long, 5 meters long, etc.

In this example, control box 2200 may house one or more of a battery pack to provide power to endoscope 2000, a control board, a network interface (e.g., WIFI board), an image sensor (e.g., CCD or CMOS chip), and other components that may be used to operate endoscope 2000. For example, while an LED light source is contained within the endoscope housing 2020, all the other components may be housed in the control box 2200. The control box may communicatively couple to mobile devices such as smartphones, laptops, or tablets (e.g., to transmit live video).

By virtue of this configuration that removably couples endoscope 2000 to control box 2200 using a cable 2100, the ergonomics of endoscope 2000 may be optimized or improved. For example, during a procedure, a physician may clip the portable control box 2200 on a belt or place control box 2200 in a pocket or other convenient location. This design may also lighten the endoscope, and detachment of the cable allows the scope and cable to be sterilized separately. Such a design may be practical for ERs, third world countries, NASA, EMTs, and in ENT offices and surgical ORs. This is in contrast to present, bulky WIFI endoscopes where components such as the battery pack, control board, and camera are housed or attached to the endoscope itself. These present endoscopes may be too heavy and cumbersome for surgical operations.

In alternative implementations, the cable 2100 may connect to a non-WiFi, hard-wired control box that could be placed on a surgical video tower unit.

By virtue of locating certain components (e.g., power source to power the endoscope, control board to control the endoscope, network interface, etc.) in the portable control box, the maximum thickness of the endoscope may be minimized. For example, in some implementations, the endoscope of the portable endoscope system may have a maximum thickness of 1 cm to 4 cm. In other implementations, the maximum thickness of the endoscope may by less than 1 cm or greater than 4 cm.

Although the portable endoscope system of FIGS. 69-70 is depicted as having certain mechanisms for attaching the endoscope to an instrument, it should be appreciated that the portable endoscope system described herein may be implemented without any mechanism for attaching it to an instrument or using some other mechanism for attaching it to an instrument. Moreover, it should be appreciated that although the portable endoscope system of FIGS. 69-70 is described with reference to a flexible-rigid hybrid endoscope having a rigid proximal end and a flexible distal end, the portable endoscope system may be implemented using a rigid endoscope having both a rigid proximal end and a rigid distal end, a flexible endoscope having a flexible proximal end and a flexible distal end, or any other suitable endoscope.

Figure 71:
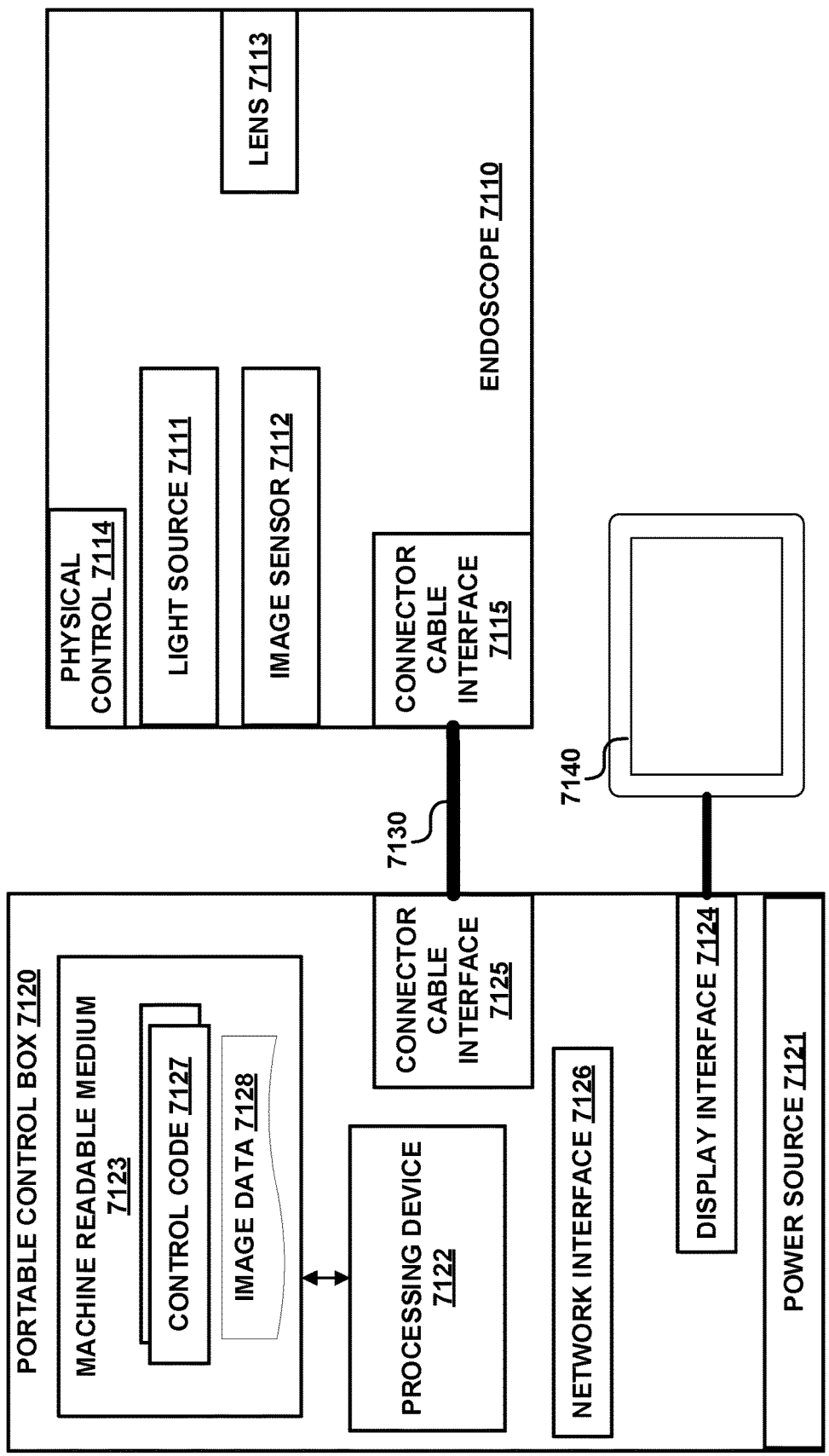
FIG. 71 is a block diagram illustrating an example architecture of a portable endoscope system, in accordance with implementations of the disclosure.

FIG. 71 is a block diagram illustrating an example architecture of a portable endoscope system 7100, in accordance with implementations of the disclosure. As depicted, the portable endoscope system 7100 comprises an endoscope 7110, a portable control box 7120, a connector cable 7130 connecting endoscope 7110 and control box 7120, and a display 7140 communicatively coupled to control box 7120. Although portable control box 7120 and display 7140 are depicted as separate components, display 7140 may be integrated into control box 7120 (e.g., in one of the side surfaces of the control box 7120).

Connector cable 7130 may provide power-line communications (PLC) between the portable control box 7120 and endoscope 7110. By virtue of this implementation, the same cable that is used to supply power from the portable control box 7120 to the endoscope 7110 may also provide data communications between the portable control box 7120 and the endoscope 7110. For example, the same connector cable may be used to transmit image sensor data collected by the endoscope 7110 to the control box 7120, to transmit control signals from the portable control box 7120 to the endoscope 7110, and/or to transmit other communications signals between the endoscope 7110 and control box 7120. In alternative implementations, separate cables may be used for supplying power and providing data communications.

Endoscope 7110 comprises a light source 7111 (e.g., LED) for illuminating a subject, an image sensor 7112, a lens 7113, a physical control 7114, and a connector cable interface 7115.

Light source 7111, image sensor 7112, and lens 7113 may be components of an imaging system of endoscope 7110. For example, light that is emitted by light source 7111 may be carried in a distal direction by one or more optical cables (not shown) for emission at a distal end of endoscope 7110 (e.g., to illuminate an internal cavity of a patient). Light reflected by the internal cavity of the patient may be collected by lens 7113 and carried in a proximal direction by one or more optical cables (not shown) to image sensor 7112 to generate image data (e.g., upon collection of light at photosites of the image sensor 7112 to generate charge that is used to generate digital image data). The generated image data may be transmitted to portable control box 7120 via a connector cable 7130 coupled to cable interface 7115.

Physical control 7114 is configured to adjust an orientation of an image (e.g., image of video feed of patient's cavity) that is displayed on display 7140 via control box 7120. By actuating physical control 7114, a user of endoscope 7110 may change the orientation of the image displayed on display 7140. By virtue of this implementation, the orientation of the image (e.g., video feed of patient's cavity) may be adjusted regardless of the physical orientation of the endoscope 7110. For example, if endoscope 7110 is turned on its side, causing the image of an inside of a patient's nose to appear sideways, the physician may operate control 7114 to right the orientation of the image (e.g., by rotating the displayed image 90 degrees). In this manner, the physician may more easily interpret the displayed image, thereby improving the efficiency of an endoscopic procedure.

To facilitate access by a physician or other user, control 7114 may be positioned on a proximal end of the body of endoscope 7110. For example, it may be situated on the body of endoscope 7110 such that when the proximal end of the endoscope is gripped by the physician, the control 7114 may be adjusted by the physician's thumb or other finger. Such a configuration may improve ergonomics and the ease of using the control 7114 to control the displayed image. Control 7114 may use touch-based components (e.g., use capacitive sensing of the user's finger(s)), tactile components, movable components, or some combination thereof. An actuatable portion of control 7114 may be implemented using a dial, a wheel, a thumbstick, a joystick, a ring, a push button, a directional pad, some other actuatable mechanism, or some combination thereof.

In some implementations, control 7114 may be configured to control the orientation of a displayed video feed in stepwise increments. For example, control 7114 may be configured to rotate the displayed image in increments of 1 degree, 5 degrees, 15 degrees, 30 degrees, 45 degrees, 90 degrees, or some other increment. In the case of a dial, for instance, each turn of the dial may correspond to a predetermined increment (e.g., in degrees of rotation). In some implementations, a predetermined increment value corresponding to an actuation of control 7114 (e.g., dial turn) may be adjusted (e.g., via a physical or software-based user interface of control box 7120) to adjust the sensitivity or otherwise customize the control 7114 for a particular user.

In some implementations, control 7114 may also be configured to control the zoom of the displayed image. Image zoom control may be performed independently of or in conjunction with image orientation control. For example, different actuatable components of control 7114 may be used to control image orientation and image zoom. By way of example, consider a control 7114 that is implemented using a thumbstick. Orientation of the displayed image may be controlled by rotating the thumbstick, and zoom may be controlled by pressing or releasing the thumbstick.

In some implementations, the zoom control may be a digital zoom control that digitally zooms the displayed image. For example, the size of displayed pixels of the image may be enlarged or reduced. In other implementations, the zoom control may be an optical zoom control that optically zooms the displayed image. For example, in some implementations, endoscope 7110 may include a zoom lens (not shown) that may be translated to increase or decrease the focal length of its imaging system, thereby adjusting the size of the image projected on image sensor 7112. In some implementations, a combination of digital and optical zoom control may be used.

The control 7114 may include a sensor (not shown) that generates a data signal in response to detecting actuation of a component of control 7114. The data signal may be transmitted over a connector cable 7130 that is coupled to connector cable interface 7115. The data signal may carry data indicating how control 7114 was actuated such that the orientation and/or zoom of the displayed image may be adjusted.

In some implementations, endoscope 7110 may include a position sensor (not shown) that may generate electronic signals representative of the position or motion of endoscope 7110. These electronic input signals may be received and processed by circuitry of endoscope 7110 or circuitry of portable control box 7120 to determine an orientation of endoscope 7110 during use. The determined orientation of endoscope 7110 from the position sensor may assist with determining an orientation or adjusting an orientation of an image displayed on display 7140. This position sensor may include one or more gyroscopes, accelerometers, and/or magnetometers.

Connector cable interface 7115 may be configured to connect to a connector of connector cable 7130. It may include a male or female port. Interface 7115 may be configured to receive power supplied by portable control box 7120 and provide data communications with portable control box 7120.

Portable control box 7120 comprises a power source 7121, a processing device 7122, a machine readable medium 7123, a display interface 7124, a connector cable interface 7125, and a network interface 7126. One or more components of portable control box 7120 may be housed by a housing.

Power source 7121 may be configured to supply power to the components of control box 7120. It may also be configured to supply power to endoscope 7110 (e.g., over connector cable 7130 connected to connector cable interface 7125). It may be implemented as a mobile power source. For example, it may be implemented as a rechargeable battery (e.g., lithium-ion battery) that may be charged using an AC/DC power supply.

Machine readable medium 7123 stores control instructions or code 7127 that may be executed by processing device 7122 to operate control box 7120. For example, execution of control code 7127 may cause control box 7120 to process image data received from endoscope 7120 over connector cable 7130, transmit image data to be displayed to a display 7140 using display interface 7124 (e.g., USB, HDMI, etc.), and/or perform various control functions in conjunction with operating the portable endoscope system 7100, including sending control signals to endoscope 7110. Machine readable medium 7123 may also store image data 7128 received from the endoscope 7110. In some implementations, processing device 7122 and machine readable medium 7123 may be components of a control board of portable control box 7120.

In conjunction with processing image data, portable control box 7120 may control a resolution and/or frame rate of the video feed presented on display 7140. Additionally, any data generated by control 7114 and received at control box 7120 may be used to determine a final orientation and/or zoom of a displayed image. In some implementations, an image orientation state variable may be maintained during execution of control code 7126. For example, the state variable may indicate an angle of rotation of the image from an unrotated position. In some implementations, the displayed image may be cropped and/or zoomed to account for the orientation of the image. For example, the image may be cropped depending on parameters such as the angle of image rotation (e.g., relative to no rotation), the pixel resolution of the image sensor 7112, the display resolution of display 7140, and other parameters.

Connector cable interface 7125 may be configured to connect to a connector of connector cable 7130. It may include a male or female port. Interface 7125 may be configured to connect to connector cable 7130 to supply power to endoscope 7110 and provide data communications with endoscope 7110.

Network interface 7126 may enable data communications between portable control box 7120 and an external device over a communication network. For example, network interface 7126 may include a wireless interface such as WiFi or Bluetooth, a wired interface such as Ethernet, or some combination thereof. In some implementations, network interface 7126 be utilized to transmit image data to display 7140. In such implementations, display interface 7124 may not be included.

In some implementations, display 7140 may be a display of a head mounted display (HMD). For example, the HMD may implemented using smart glasses, a visor, googles, or some other suitable HMD. The HMD may be worn by a user of the endoscope 7110, and it may provide a see-through display (e.g., video or optical see-through) that permits the user to both: i) observe in real-time, on the display, an image generated by the endoscope; and ii) observe "through" the display the user's surrounding environment such as the endoscope, instruments attached to the endoscope (if any), the positioning of the endoscope instrument relative to the subject, etc. The HMD may couple to control box 7120 via a cable connector or via a wireless communication protocol. In some implementations, display 7140 may be a display of a mobile device such as a smartphone, tablet, or laptop that communicatively couples to control box 7120 via a wired or wireless communication protocol.

Attachment Mechanisms for Flexible-Rigid Hybrid Endoscope

As alluded to above, the flexible-rigid hybrid endoscope described herein may removably couple to a variety of different medical instrument types using two primary areas of attachment: a rigid proximal end and a flexible distal end. For example, a rigid proximal attachment segment 131, 231, 331, 431, 530 may removably couple to a handle portion of an instrument. Additionally, depending on the instrument and tool type, a flexible distal end 140, 340 may removably couple to and follow the contour of a distal aspect or end of an instrument such that the objective lens of the flexible distal end is positioned proximal to a tool of the instrument (e.g., instrument component that enters patient's cavity to perform procedure). In this manner, the objective lens may provide proper visualization of the instrument's tool and the patient's cavity while performing a procedure on the patient.

Figure 8:
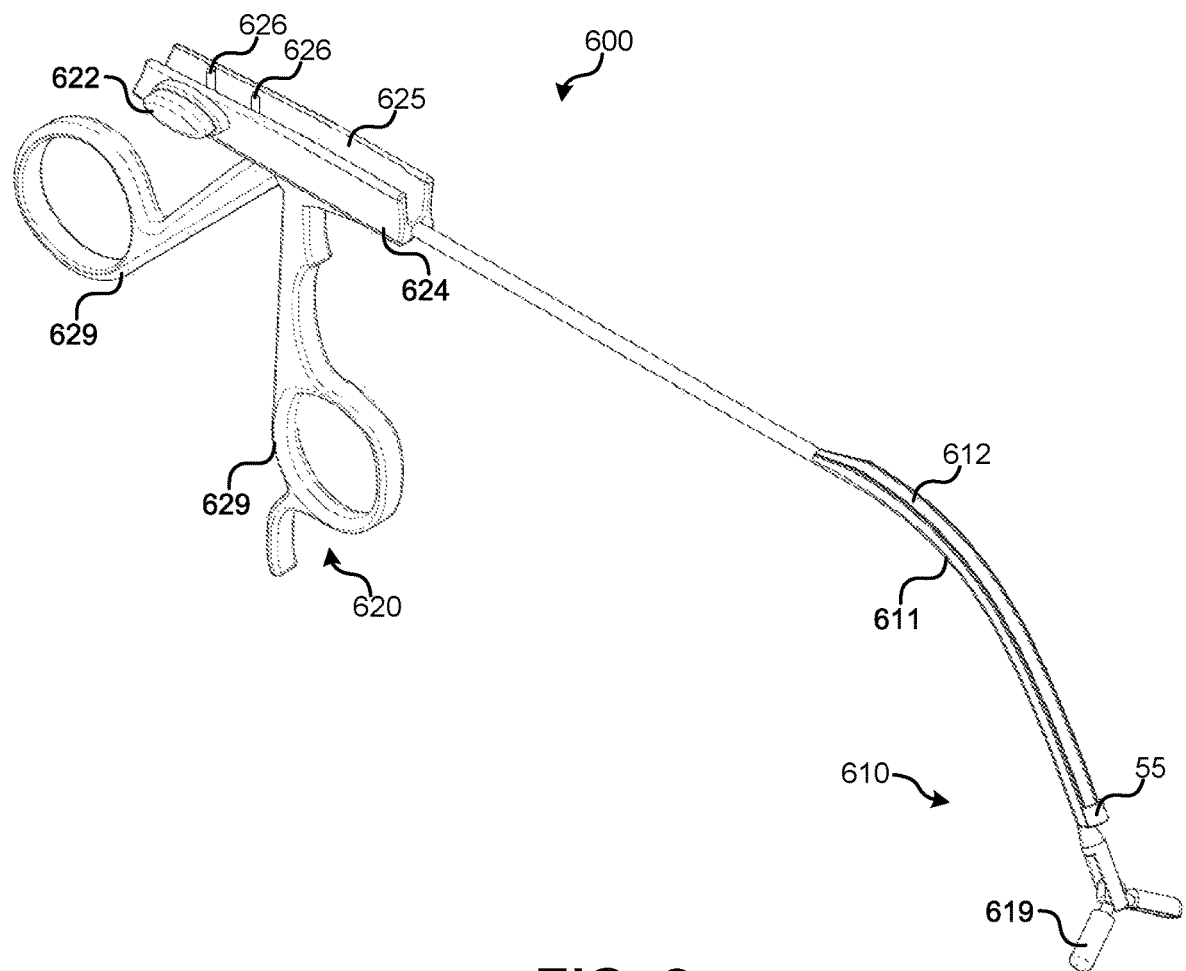
FIG. 8 shows a perspective view of a laryngeal forceps instrument, including a top down ratchet attachment mechanism, that an endoscope may couple to in accordance with implementations of the disclosure.
Figure 9:
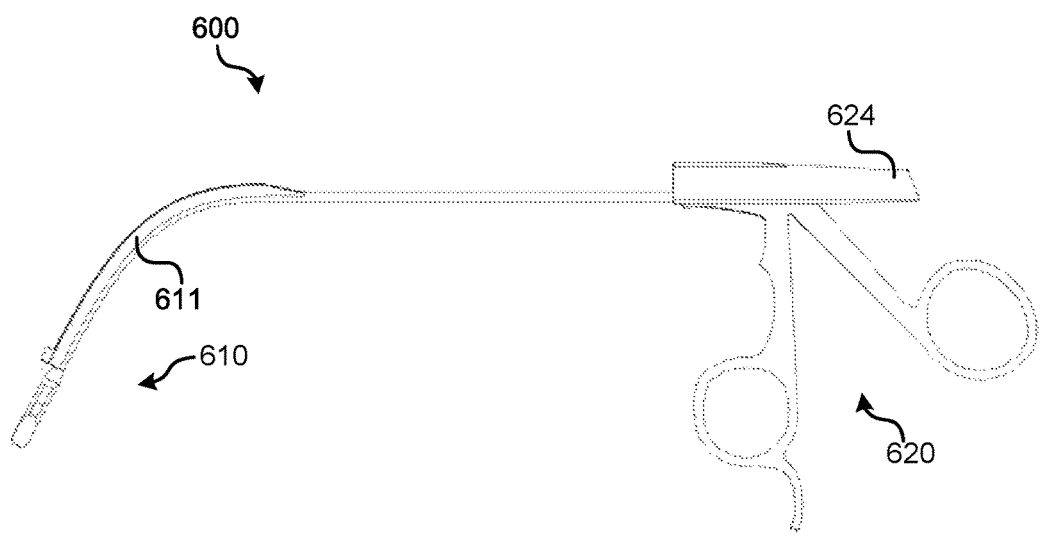
FIG. 9 shows a side view of the laryngeal forceps instrument of FIG. 8.
Figure 10:
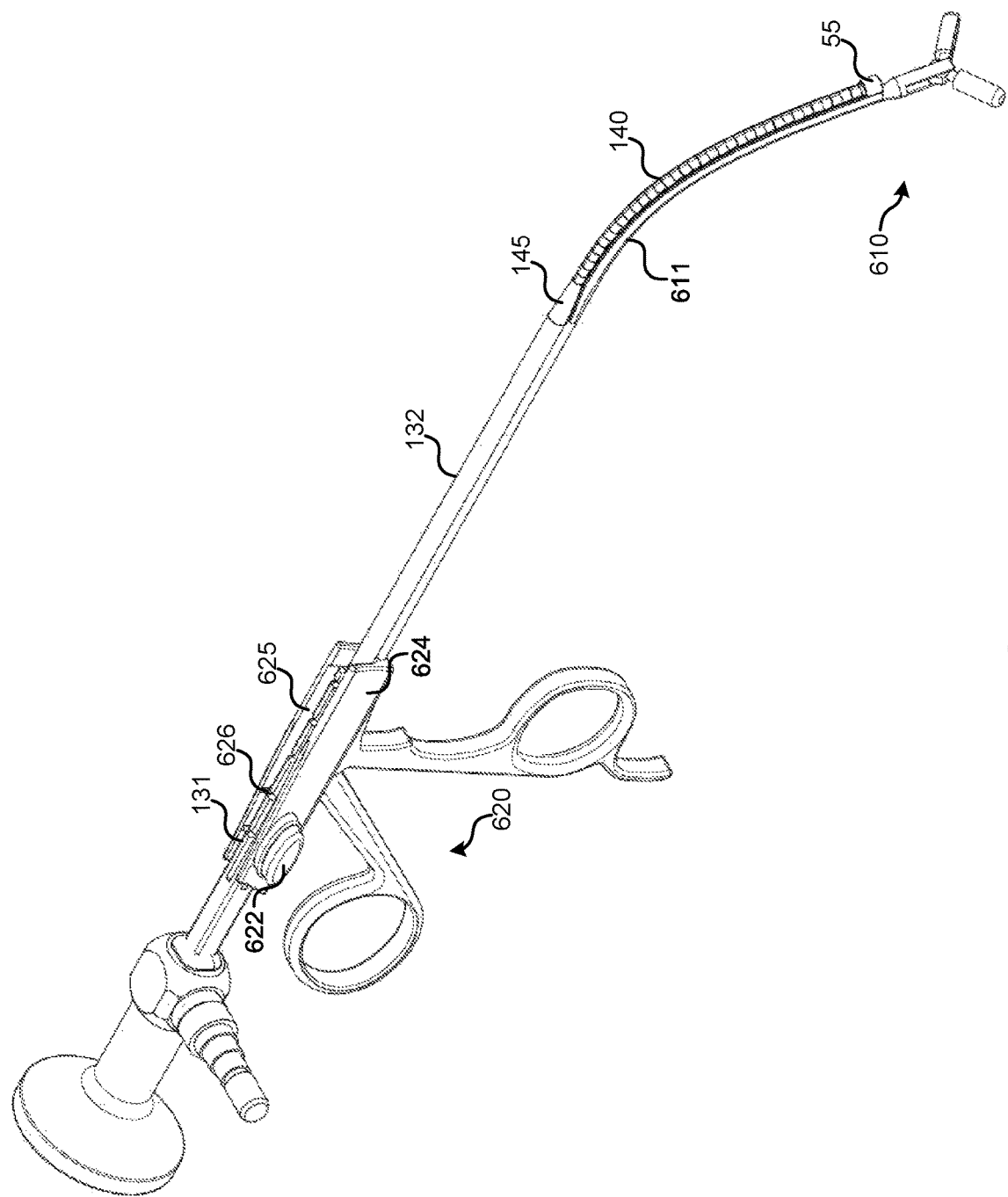
FIG. 10 shows a perspective view of the laryngeal forceps instrument of FIG. 8, including a coupled endoscope.
Figure 11:
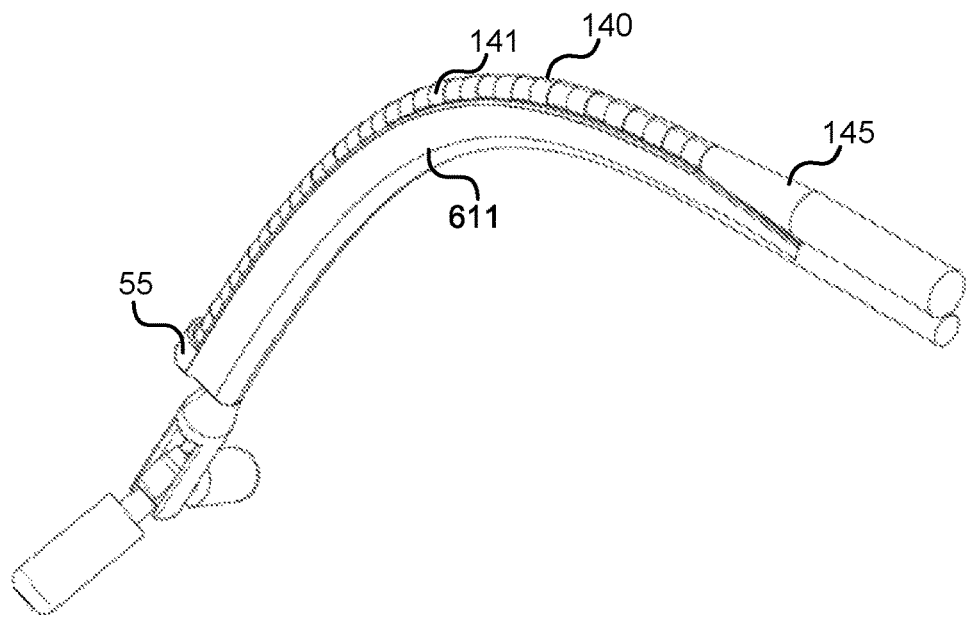
FIG. 11 shows a perspective view of a flexible distal end of an endoscope magnetically coupled to a tool portion of laryngeal forceps.
Figure 12:
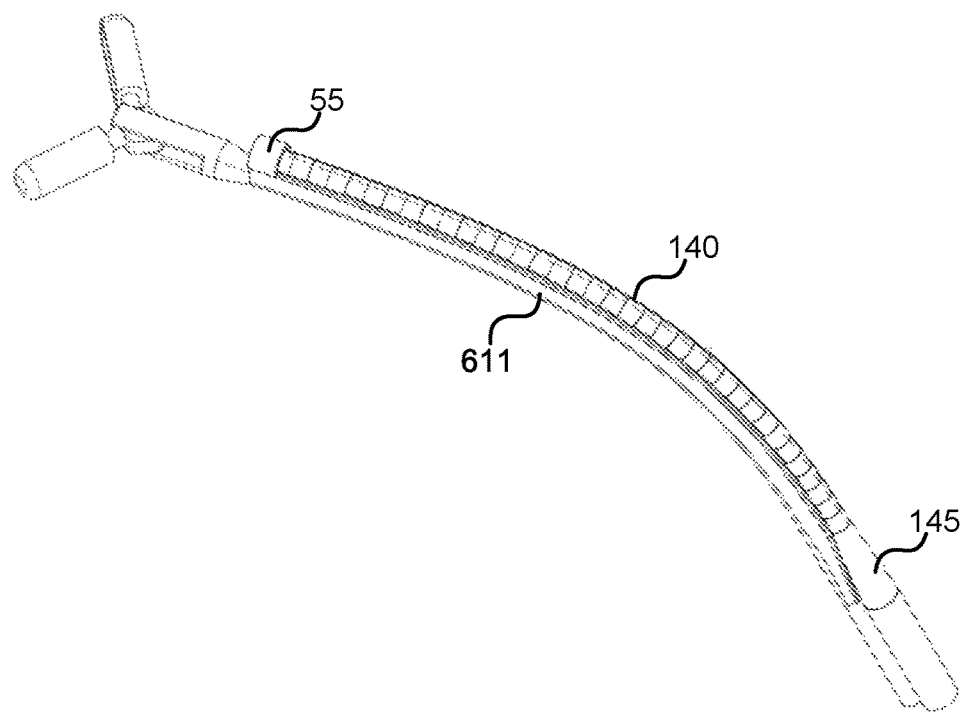
FIG. 12 shows a perspective view of a flexible distal end of an endoscope magnetically coupled to a tool portion of laryngeal forceps.
Figure 13:
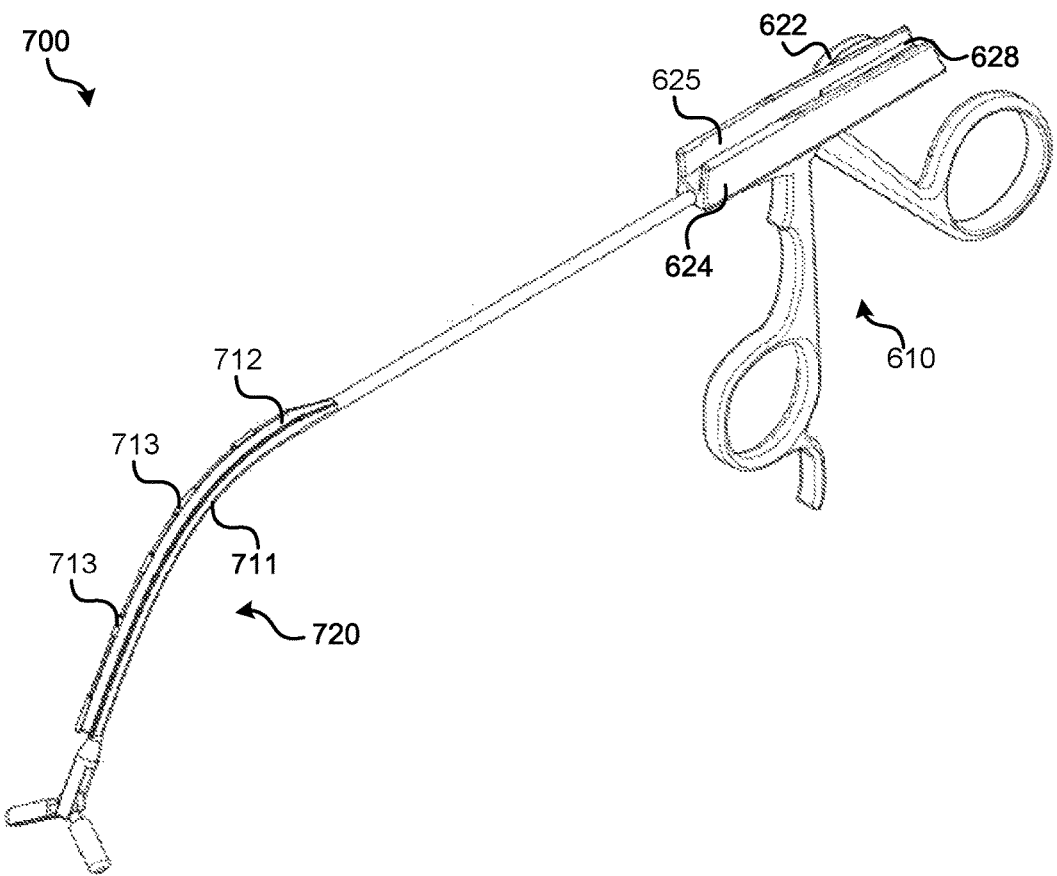
FIG. 13 shows a perspective view of a laryngeal forceps instrument, the laryngeal forceps instrument including a curved open channel with one or more clips that a flexible distal end of an endoscope may couple to, in accordance with implementations.
Figure 14:
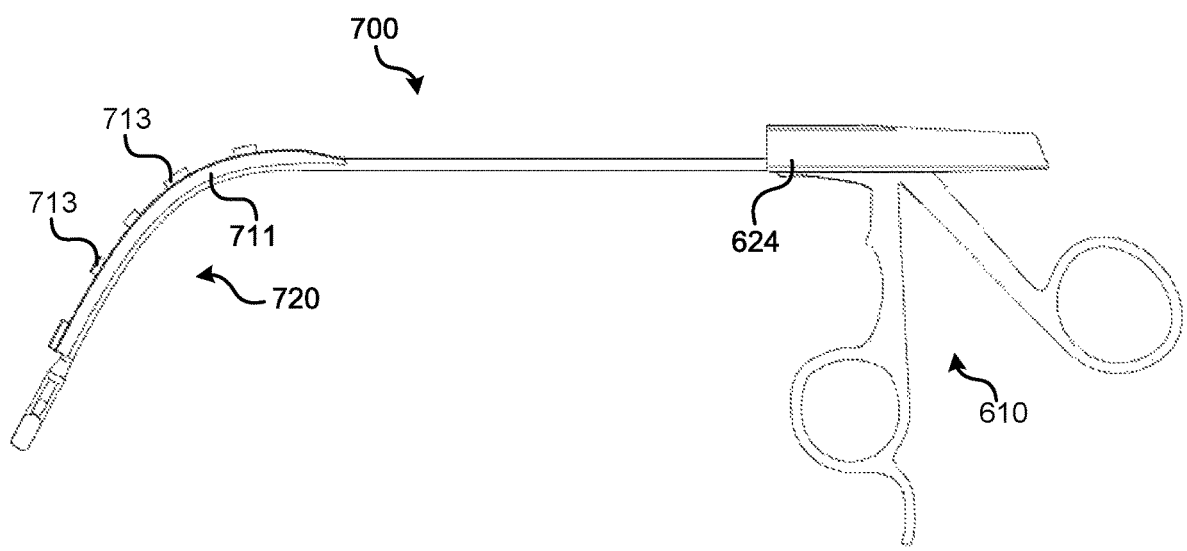
FIG. 14 shows a side view of the laryngeal forceps instrument of FIG. 13.
Figure 15:
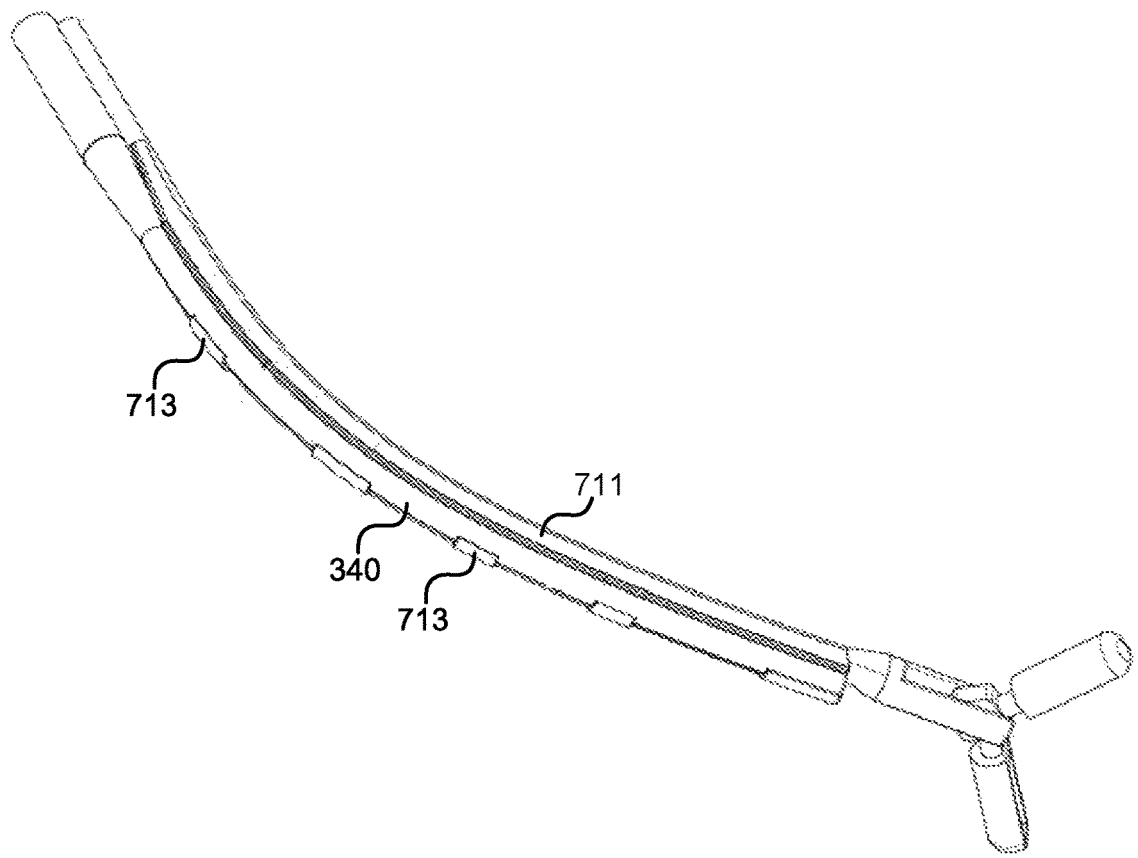
FIG. 15 shows a perspective view of a flexible distal end of an endoscope coupled to a tool portion of laryngeal forceps, the tool portion including an open channel with one or more clips for coupling the flexible distal end.
Figure 16:
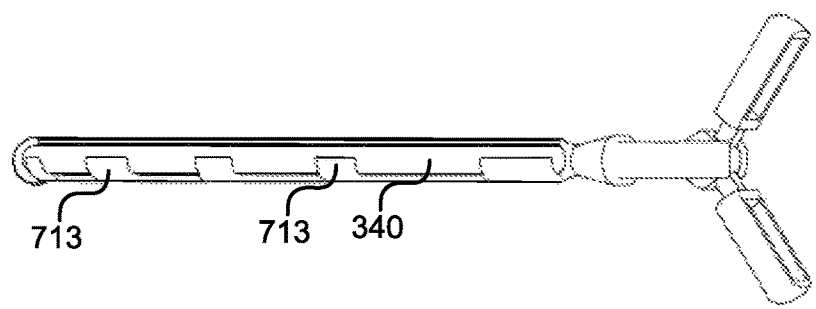
FIG. 16 shows a perspective view of a flexible distal end of an endoscope coupled to a tool portion of laryngeal forceps, the tool portion including an open channel with one or more clips for coupling the flexible distal end.
Figure 17:
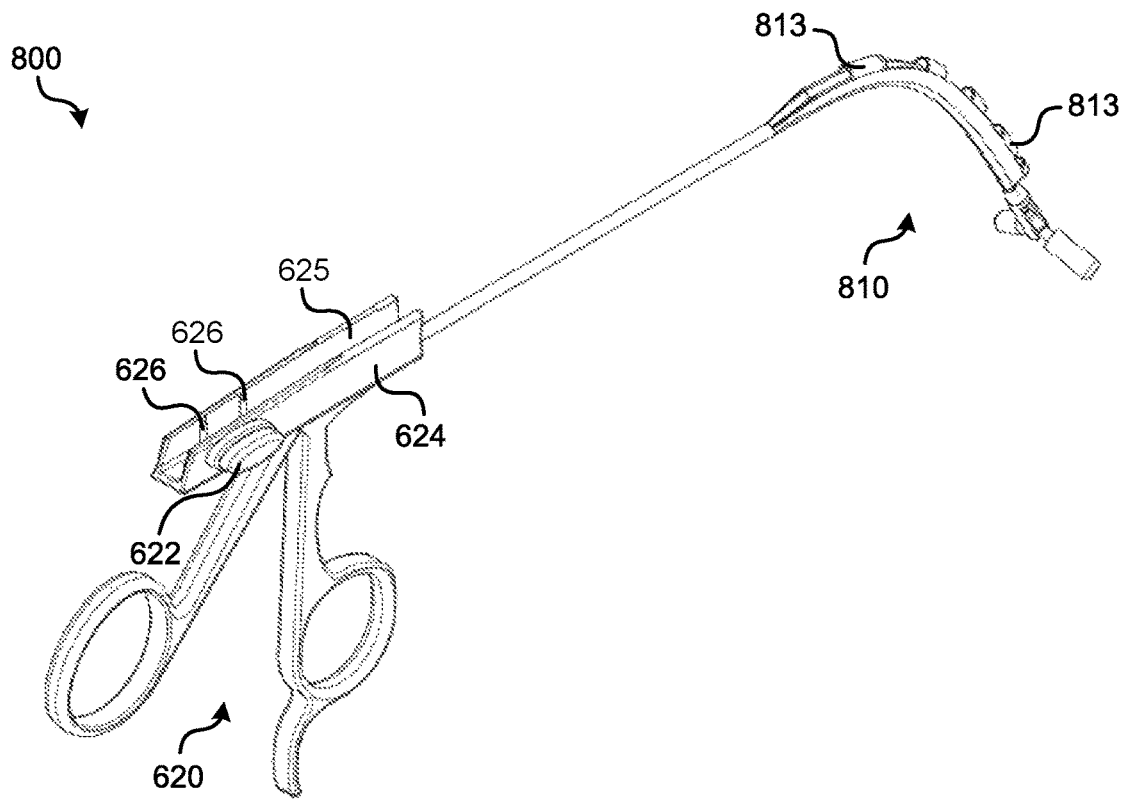
FIG. 17 shows a perspective view of a laryngeal forceps instrument, the laryngeal forceps instrument including a curved open channel with one or more elongated tubes that a flexible distal end of an endoscope may couple to, in accordance with implementations.
Figure 18:
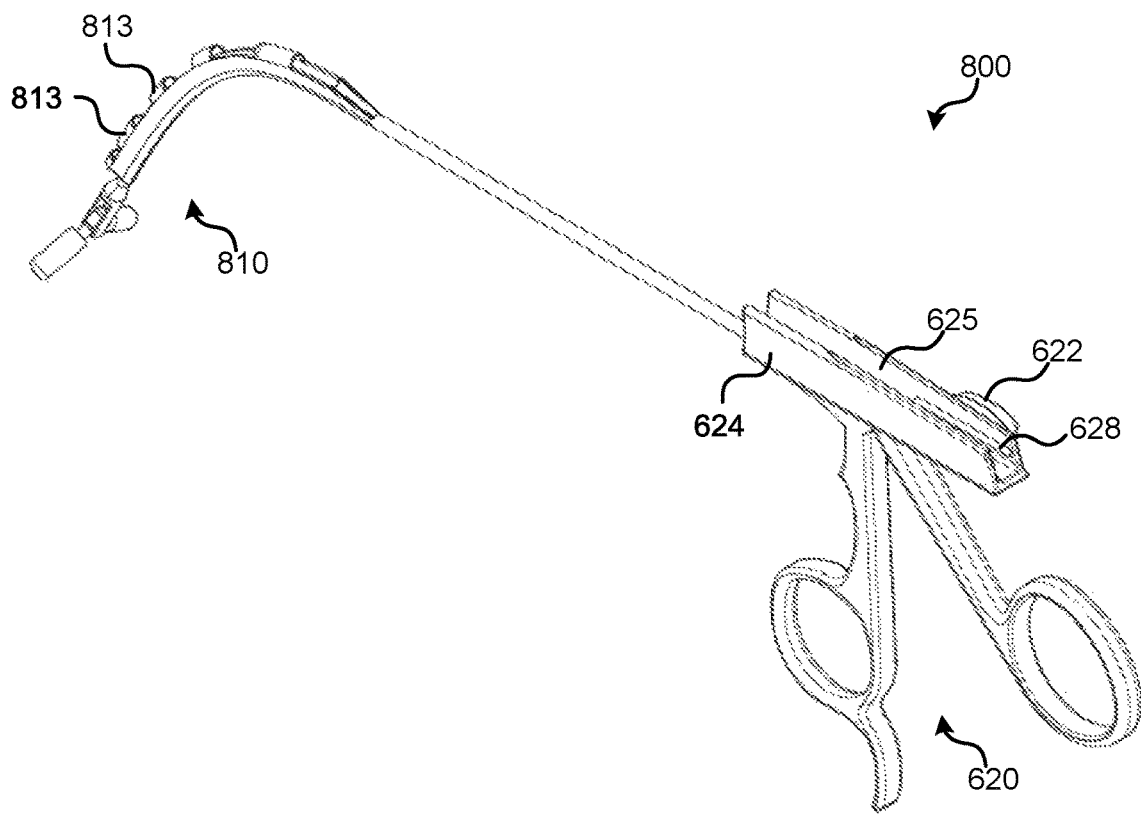
FIG. 18 shows another perspective view of the laryngeal forceps instrument of FIG. 17.
Figure 19:
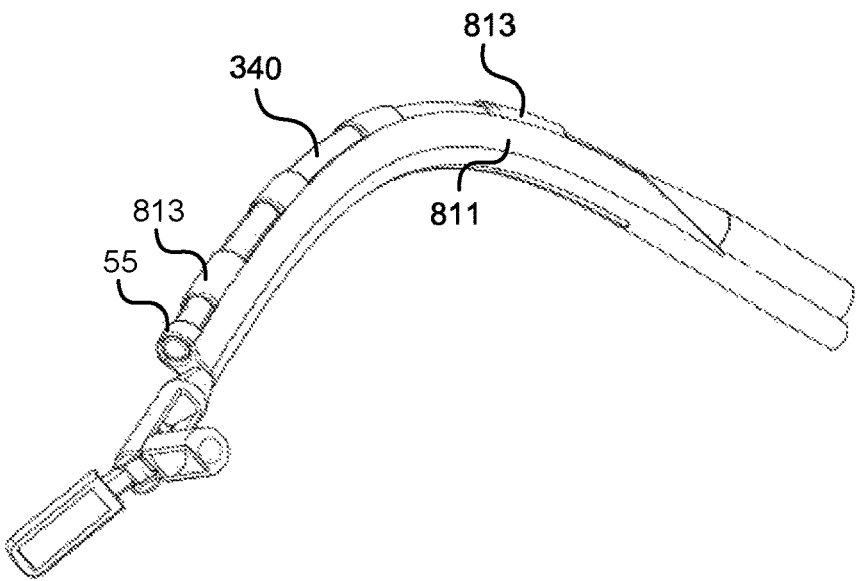
FIG. 19 shows a perspective view of a flexible distal end of an endoscope coupled to a tool portion of laryngeal forceps, the tool portion including an open channel with one or more elongated tubes for coupling the flexible distal end.
Figure 20:
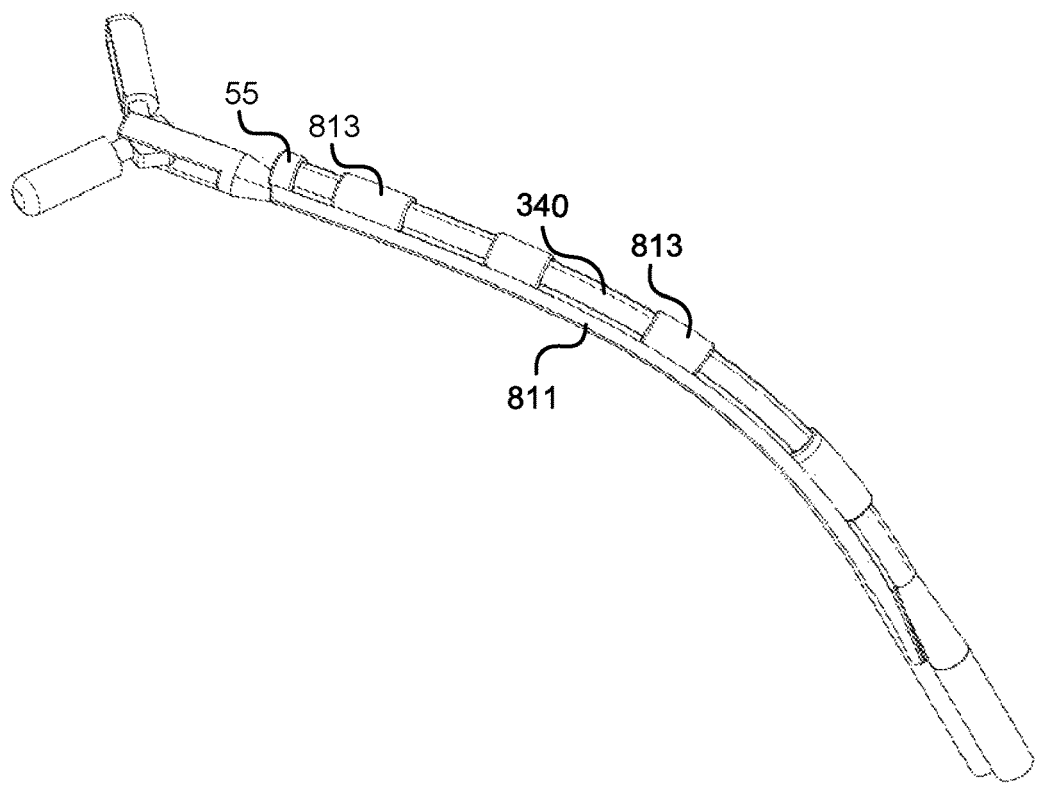
FIG. 20 shows a perspective view of a flexible distal end of an endoscope coupled to a tool portion of laryngeal forceps, the tool portion including an open channel with one or more elongated tubes for coupling the flexible distal end.
Figure 61:
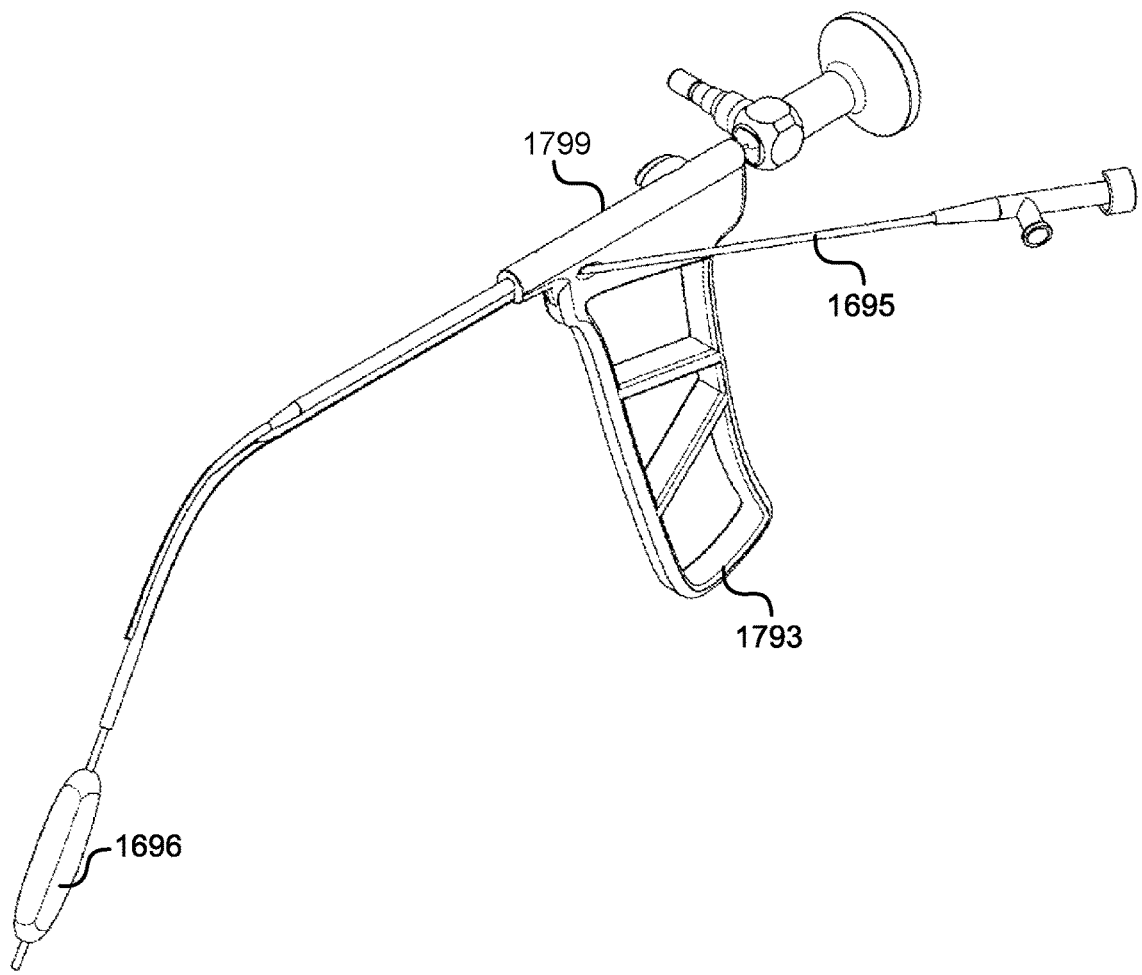
FIG. 61 shows another perspective view of the endoscopic trans-oral esophageal balloon dilator with coupled endoscope of FIG. 60.

Such attachment mechanisms that may be configured to provide a quick, secure, and/or simple mechanism for removably coupling the endoscope to the instrument are further described below with reference to FIGS. 8-61. It should be noted that the disclosure is not limited to the specific attachment mechanisms described and illustrated herein, and that other mechanisms for removably coupling the flexible-rigid endoscope to an instrument are contemplated. It should also be noted that although some attachment mechanisms will primarily be described in the context of a specific endoscope (e.g., endoscope 100), the attachment mechanisms may apply to other flexible-rigid endoscopes described herein, or variants thereof, including rigid endoscopes or flexible endoscopes, assuming they are compatible with the attachment mechanism. For example, some of the attachment mechanisms described herein for the rigid proximal end of the endoscope (e.g., top down ratchet mechanism, insert ratchet mechanism, etc.) may be implemented in a rigid endoscope having both a rigid proximal and a rigid distal end.

Further, it should be noted that the different attachment mechanisms described herein are not mutually exclusive, and to the extent they are compatible, they may be used together. For example, in some cases multiple attachment mechanisms may be used to attach a rigid proximal end of an endoscope to a handle portion of an instrument, and/or multiple attachment mechanisms may be used to attach a flexible distal end of an endoscope to a tool portion of an instrument.

Magnetic Attachment Mechanism

In one implementation, illustrated by FIGS. 1-6, and 8, a magnetic attachment mechanism may be used to removably couple, in a top down manner, a rigid proximal attachment segment 131, 231, 331, 431, 530 of an endoscope 100 to the open channel 625 segment of the tool housing 624. In such implementations, segment 625 (e.g., the surface of the open channel) may be magnetized and/or the rigid proximal attachment segment of the flexible-hybrid scope may be magnetized. This type of magnetic implementation could be used alone or in combination with other specific attachment mechanisms described and illustrated herein.

Top Down Ratchet Mechanism

In some implementations, illustrated by FIGS. 8-10, 13-14, 17-18, 21, 41, 48-52, and 58-59, a top-loading ratchet mechanism may be used to secure a rigid proximal attachment segment of an endoscope to a handle portion of an instrument. For example, as illustrated by FIGS. 8-10, 13-14, and 17-18, a handle portion 620 of an instrument 600 may comprise an instrument housing 624 having an elongated open channel 625 to removably couple an endoscope 100 in a top-down manner by pushing down rigid proximal attachment segment 131 into the elongated open channel 625 of housing 624.

The interior surface of the instrument housing 625 may include vertically spaced ridges 626 that may be spaced at intervals corresponding to the spacing between consecutive slots 133 of rigid proximal attachment segment 131 (e.g., about 1 cm). During attachment, a button 622 situated on an outside of housing 624 may be pressed to retract a horizontal oriented bar 628 situated on an interior side surface of open channel 625. After retracting bar 628, ridges 626 may be aligned with and inserted into slots 133. Aligning the interior vertical ridges with the longitudinally spaced slots in this manner secures the endoscope and prevents anterior-posterior movement. Once endoscope 100 is inserted (i.e., ridges inserted into slots), button 622 may be released to secure bar 128 into one of the longitudinal grooves 134 of attachment segment to prevent the endoscope from moving superiorly outside of channel 625. To reposition endoscope 100 (e.g., to turn it or move it in a posterior/anterior direction along the instrument), button 622 may be pressed, and endoscope 100 may be lifted up and then pushed down such that new slots 133 and/or grooves 134 are secured to ridges 626 and/or bar 628.

Advantageously, the top-loading ratchet mechanism described herein provides a quick and simple means for securing an endoscope to an instrument. Coupling, uncoupling, and/or repositioning an endoscope within the instrument is simply a matter of pressing the button 622, and lifting (if repositioning) and pushing down the endoscope 100 such that ridges 626 are inserted into a particular set of slots 133.

In particular implementations, the top-loading ratchet mechanism described herein may be implemented as a levered top down ratchet mechanism. Particular implementations of such a mechanism are illustrated by FIGS. 21, 41, 58-59, and 63-67. With particular reference to FIGS. 63-67, a flexible-rigid hybrid endoscope 1800 may be removably coupled to a levered down top-loading ratchet mechanism 1810 that may be situated on a handle portion of an instrument (not shown).

Figure 66:
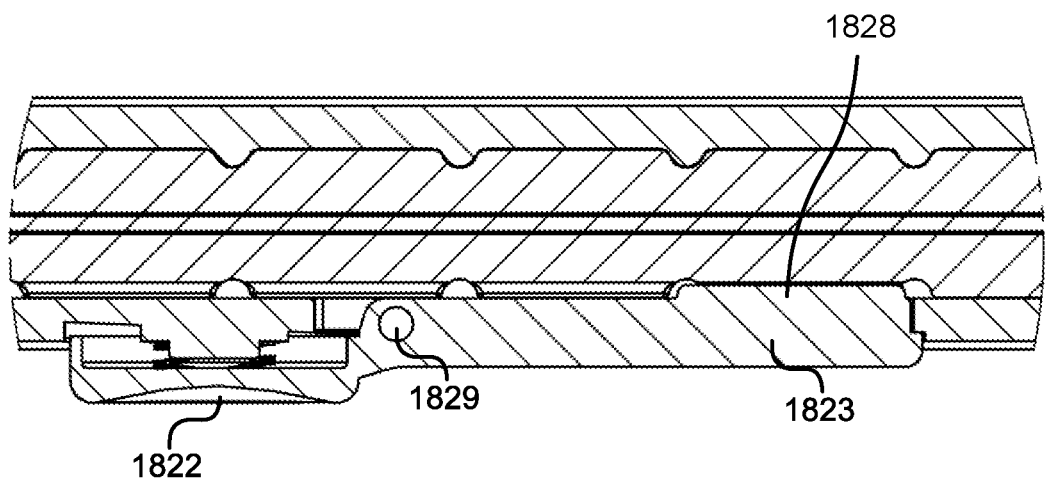
FIG. 66 shows a schematic side view of the levered top down ratchet mechanism of FIG. 64 in a closed position.
Figure 67:
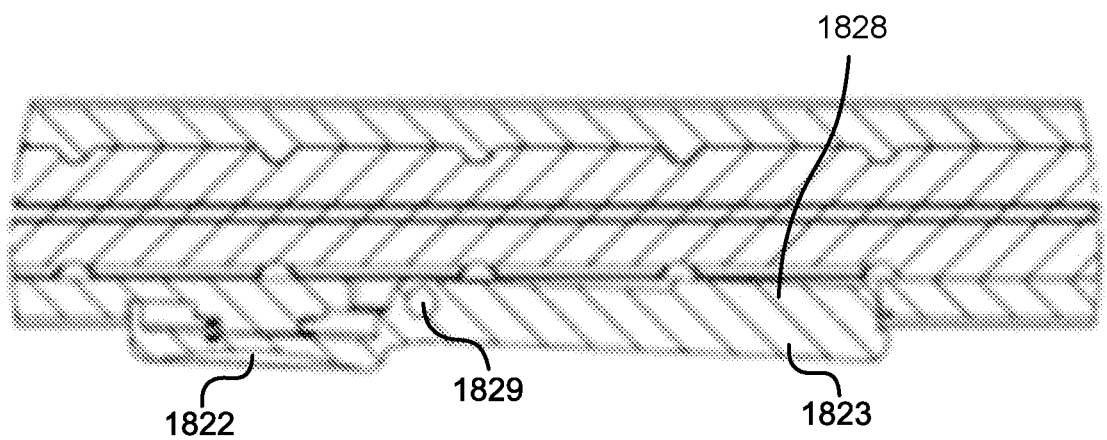
FIG. 67 shows a schematic side view of the levered top down ratchet mechanism of FIG. 64 in an open position.
Figure 68:
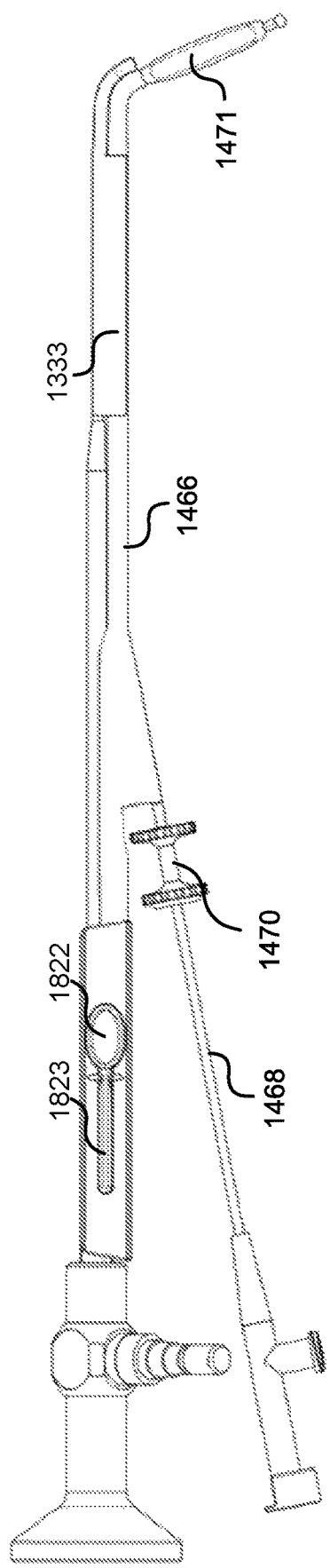
FIG. 68 shows a side view of another endoscopic Eustachian tube balloon dilator with a coupled endoscope and balloon catheter, in accordance with implementations of the disclosure.

The top-loading ratchet mechanism 1810 may include an instrument housing 1824 having an elongated open channel 1825 to removably couple endoscope 1800 in a top-down manner by pushing down a rigid proximal attachment segment into the elongated open channel 1825 of housing 1824. The interior surface of the instrument housing 1824 may include vertically spaced ridges 1826 that may be spaced at intervals corresponding to the spacing between consecutive slots 1833 of the rigid proximal attachment segment. In this particular implementation, actuation of a button 1822 situated on an outside of housing 1822 causes a portion 1828 of lever 1823 situated in the interior of housing 1824 to be retracted from the interior. For example, FIG. 66 illustrates the lever 1823 when it is in a closed or unretracted position, and FIG. 67 illustrates the lever 1823 when it is in an open or retracted position. As illustrated by FIGS. 66-67, lever 1823 may be hinged on a pin 1829 that enables this retraction when button 1822 is actuated.

Figure 21:
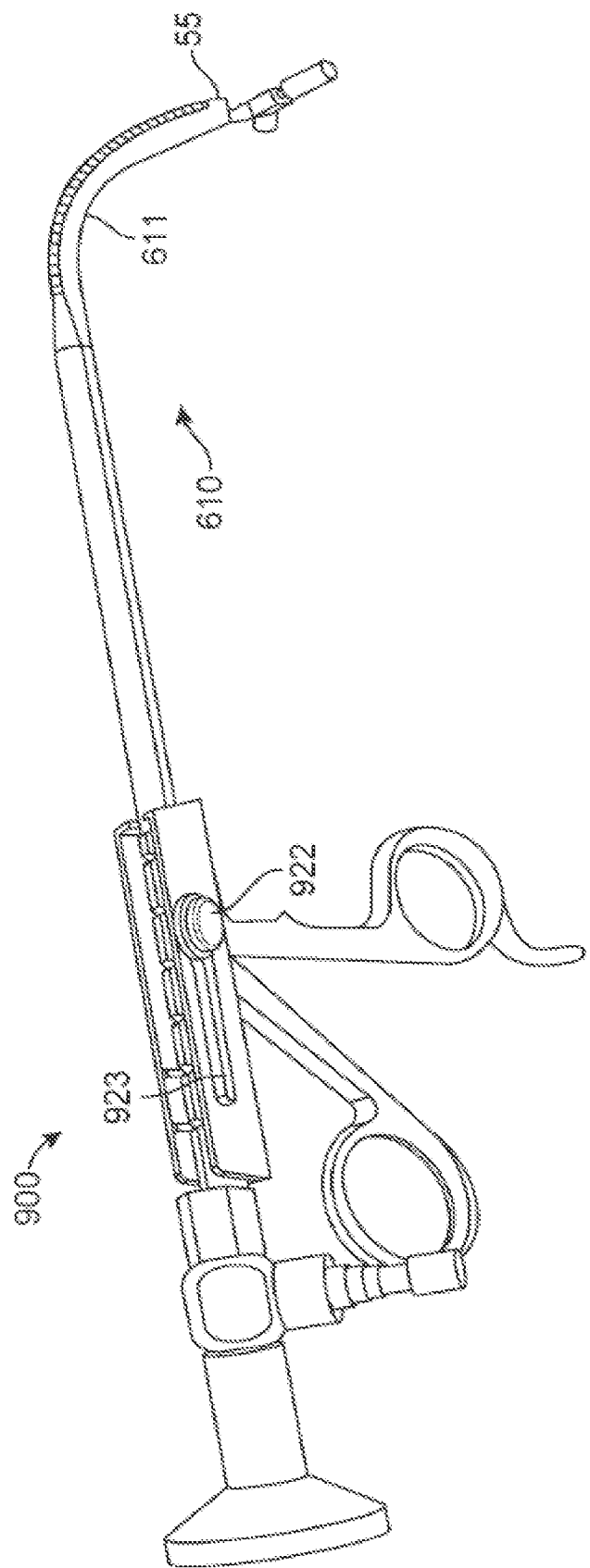
FIG. 21 shows a perspective view of a laryngeal forceps instrument, including a top down ratchet attachment mechanism that an endoscope is coupled to, in accordance with implementations of the disclosure.
Figure 22:
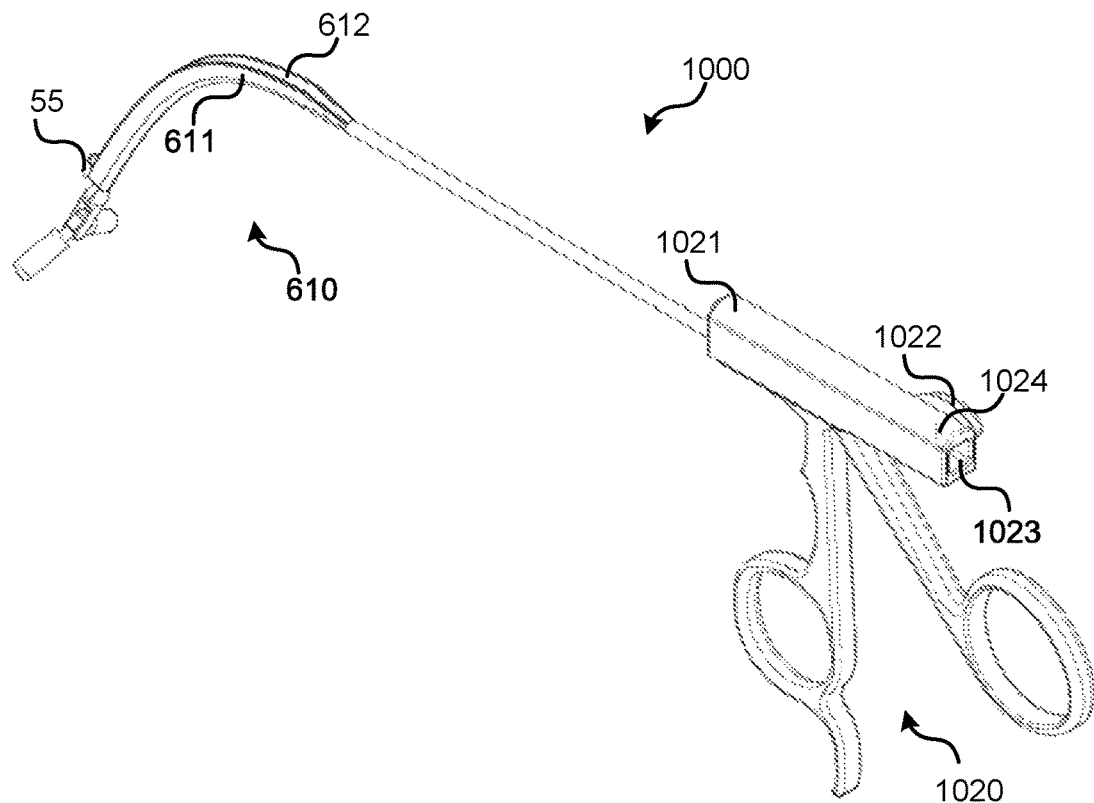
FIG. 22 shows a perspective view of a laryngeal forceps instrument, including an insert ratchet attachment mechanism, that an endoscope may couple to, in accordance with implementations of the disclosure.
Figure 23:
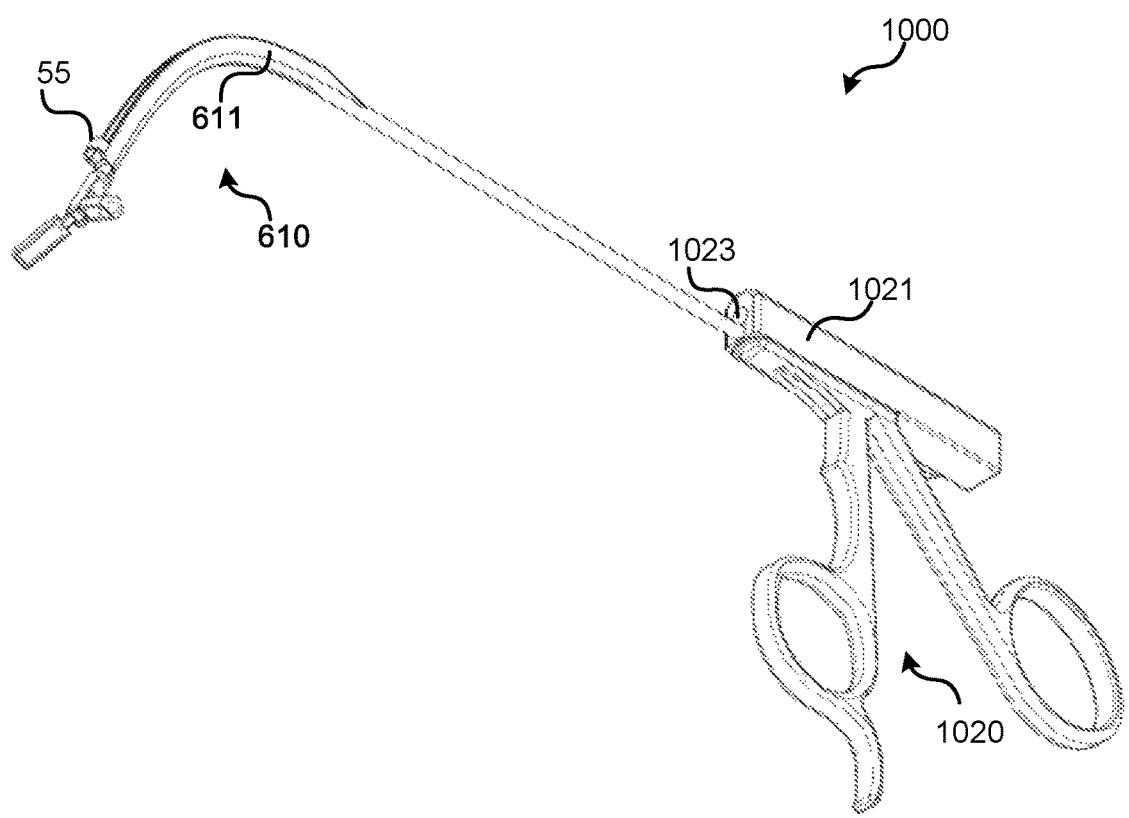
FIG. 23 shows another perspective view of the laryngeal forceps instrument of FIG. 22.
Figure 24:
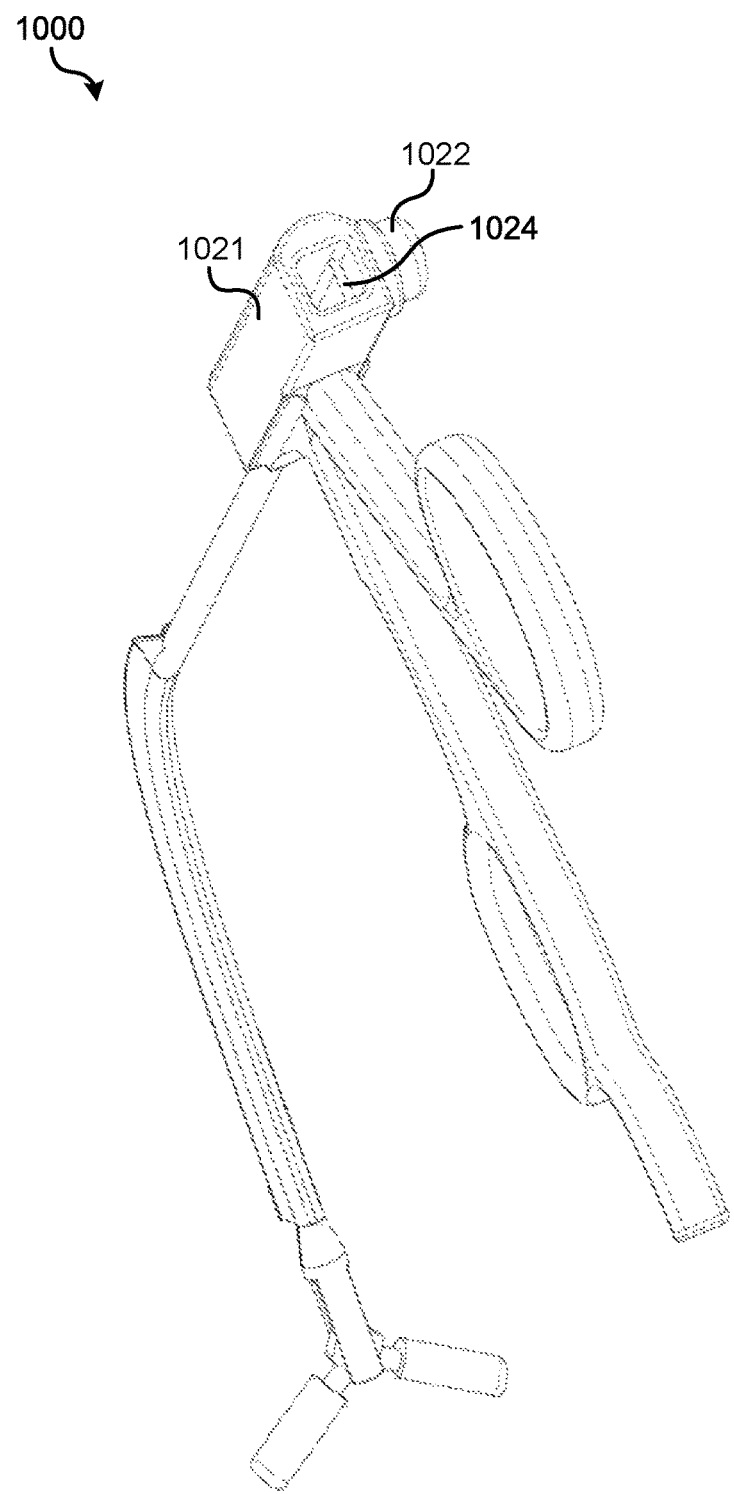
FIG. 24 shows a rear perspective view of the laryngeal forceps instrument of FIG. 22.
Figure 25:
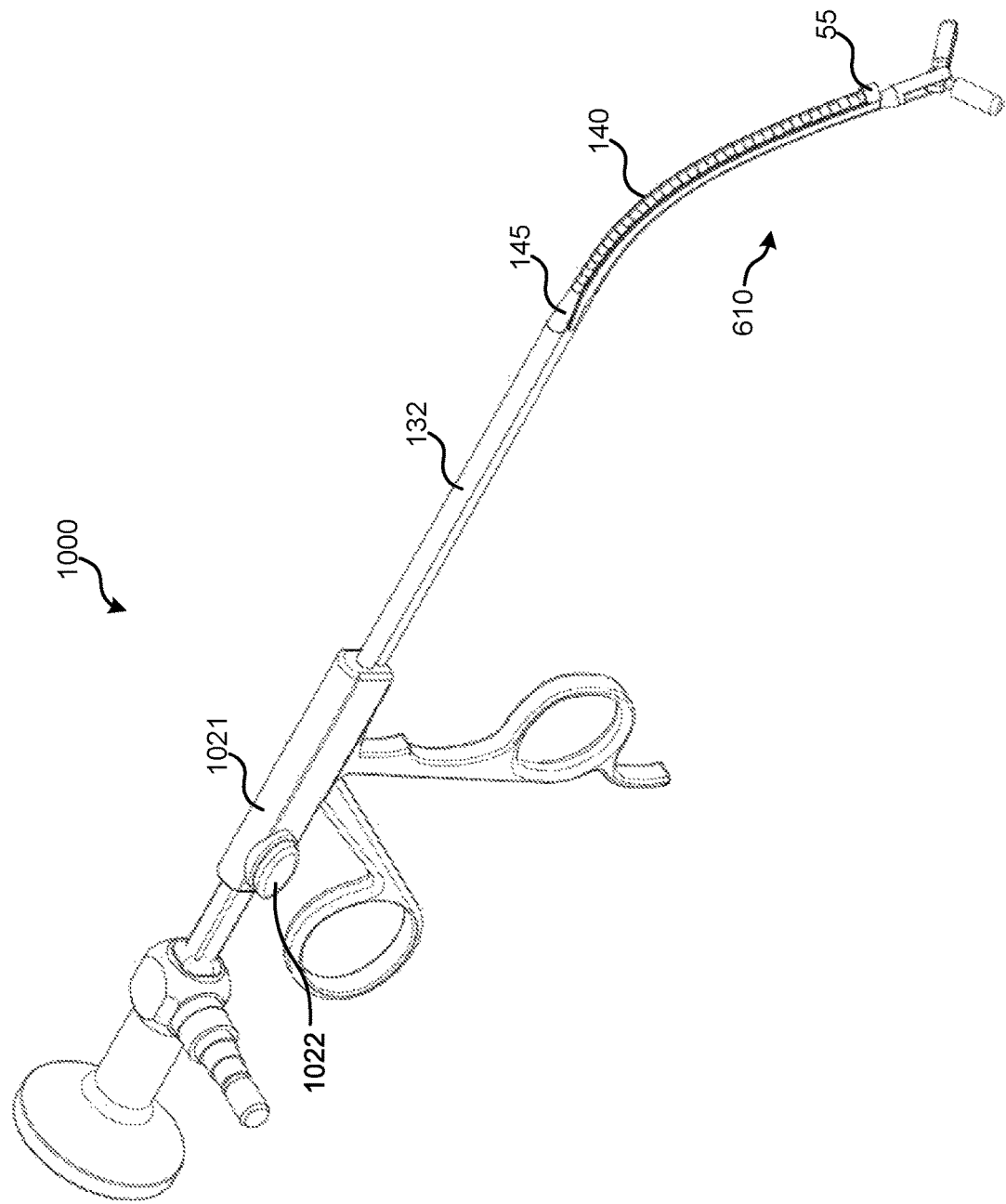
FIG. 25 shows a perspective view of the laryngeal forceps instrument of FIG. 22, including a coupled endoscope.

FIG. 21 illustrates another example implementation of an instrument 900 including a levered top-loading ratchet mechanism incorporated into a handle portion 920 of the instrument. In this example, pressing button 922 may release a lever 923 secured in a longitudinal groove of the endoscope.

In alternative implementations, the top down ratchet mechanism may be implemented by replacing the slots of the rigid proximal attachment segment of the endoscope with ridges and the ridges of the instrument's housing with slots.

In alternative implementations, other attachment mechanisms may be used to removably attach a rigid proximal segment of an endoscope to a handle portion of an instrument in a top down manner. For example, the rigid proximal segment may be attached by clamps, threaded turns, press fitting, snap fitting, friction fitting, magnetically coupling, attachment by secondary device and/or other suitable means for securely retaining the endoscope.

Insert Ratchet Mechanism

In some implementations, illustrated by FIGS. 22-28, 32-35, 37-38, 42-45, and 60-61, an insert ratchet mechanism may be used to secure a rigid proximal attachment segment of an endoscope to an instrument. For example, as illustrated by FIGS. 22-28, a handle portion 1020 of an instrument may comprise a housing 1021 located above an actuating portion of the handle portion. Housing 1021 may include a channel 1023 including opening and exit apertures. During attachment, an endoscope 100 may be inserted through the channel 1023. During insertion, longitudinally spaced slots (e.g., slots 133, 233, 333, etc.) located on the sides of the endoscope (e.g., square or rounded scope) may line up with a retractable interior protuberance 1024 (e.g., a spring loaded protuberance) actuated by the external housing button 1022. When the retractable interior protuberance 1024 is inserted in one of the longitudinally spaced slots, the endoscope may be secured in place.

Insert Twist Mechanism

In some implementations, illustrated by FIGS. 7 and 29-31, an insert twist mechanism may be used to secure a rigid proximal attachment segment of an endoscope to an instrument. For example, referring to FIG. 7, a flexible-rigid hybrid endoscope 500 may include a proximal elongated rigid attachment segment 530 that includes a series of one or more projections 533 (e.g. metallic projections). A slotted instrument channel 1223, illustrated by FIGS. 29-31, located in a housing 1221 at the top of the handled or actuating portion 1220 of the instrument may accommodate projections 533 during insertion of the endoscope.

During insertion, projections 533 may be inserted through slot 1225 of the interior channel, and the endoscope may be inserted to a desired length. The endoscope may be locked into place by aligning projections 533 with interior grooves 1224 of channel 1223, and twisting the endoscope to lock it in place, thereby preventing anterior or posterior movement. To remove the endoscope, the user may rotate the endoscope to align its exterior projections 533 with slot 1225, and pull the endoscope out of the channel. In this particular example twist-lock implementation, rotation may be enabled through an arc of about 120 degrees to permit rotation of the scope during a procedure (e.g., to realign the light cord and camera).

Mechanisms for Attaching Flexible Distal End of Endoscope

Multiple mechanisms for attaching a flexible distal end 140, 340, of a hybrid endoscope to a distal end of an instrument (e.g., a tool end) are described herein. It should be noted that these example mechanisms are not necessarily mutually exclusive, and that depending on the type of instrument used and the application of the instrument, different attachment mechanisms may need to be used. Additionally, it should be appreciated that the flexible distal end of the hybrid endoscope described herein may be attached using other attachment mechanisms than the example implementations further described below.

As alluded to above, in one implementation, illustrated by FIGS. 8-12, 21, and 25-31, a magnetic attachment mechanism may be used to removably couple a flexible distal end 140 of an endoscope to a distal/tool portion of an instrument. For example, a tool portion 610 or 1110 of an instrument may include an instrument shaft or segment 611 or 1111 including a curved, open channel 612 or 1112 for mounting the distal end of the endoscope. In these examples, the surface of channel 612 or 1112 may magnetically couple to bands 141 of distal end 140. In such implementations, segment 611 or 1111 (e.g., the surface of the open channel) may be magnetized and/or bands 141 of the instrument may be magnetized.

In another implementation, illustrated by FIGS. 13-16, a tool portion 710 of the instrument may include an instrument shaft or segment 711 including a curved open channel 712 for mounting the flexible distal end of the endoscope, and one or more clips 713 (e.g. metallic clips) longitudinally spaced along the channel that are for semi-circumferentially holding the distal end of the endoscope in place. This implementation may be combined with the magnetic attachment implementation to provide additional stability to and prevent movement of the flexible distal end of the endoscope. This implementation may also be advantageous in cases where the flexible distal end of the endoscope is not configured to magnetically attach to a distal end of the instrument. Metallic bands may be intermittently spaced along the flexible distal endoscope in order to provide protection to the delicate endoscope fibers when securing the endoscope to instrument clips or other attachment implementations.

In another implementation, illustrated by FIGS. 17-20, a tool portion 810 of the instrument may include an instrument shaft or segment 811 including a curved open channel 812 for mounting the flexible distal end of the endoscope, and one or more elongated tubes 813 longitudinally spaced along the channel that are for circumferentially holding the distal end of the endoscope in place. This implementation may be combined with the magnetic attachment implementation to provide additional stability to and prevent movement of the flexible distal end of the endoscope. This implementation may also be advantageous in cases where the flexible distal end of the endoscope is not configured to magnetically attach to a distal end of the instrument.

In another implementation, illustrated by FIGS. 34-36 and 41, the flexible end of the endoscope may be advanced through a series of loops 129 (e.g. metal loops) attached to a distal tool portion of the instrument (e.g., a needle).

Figure 37:
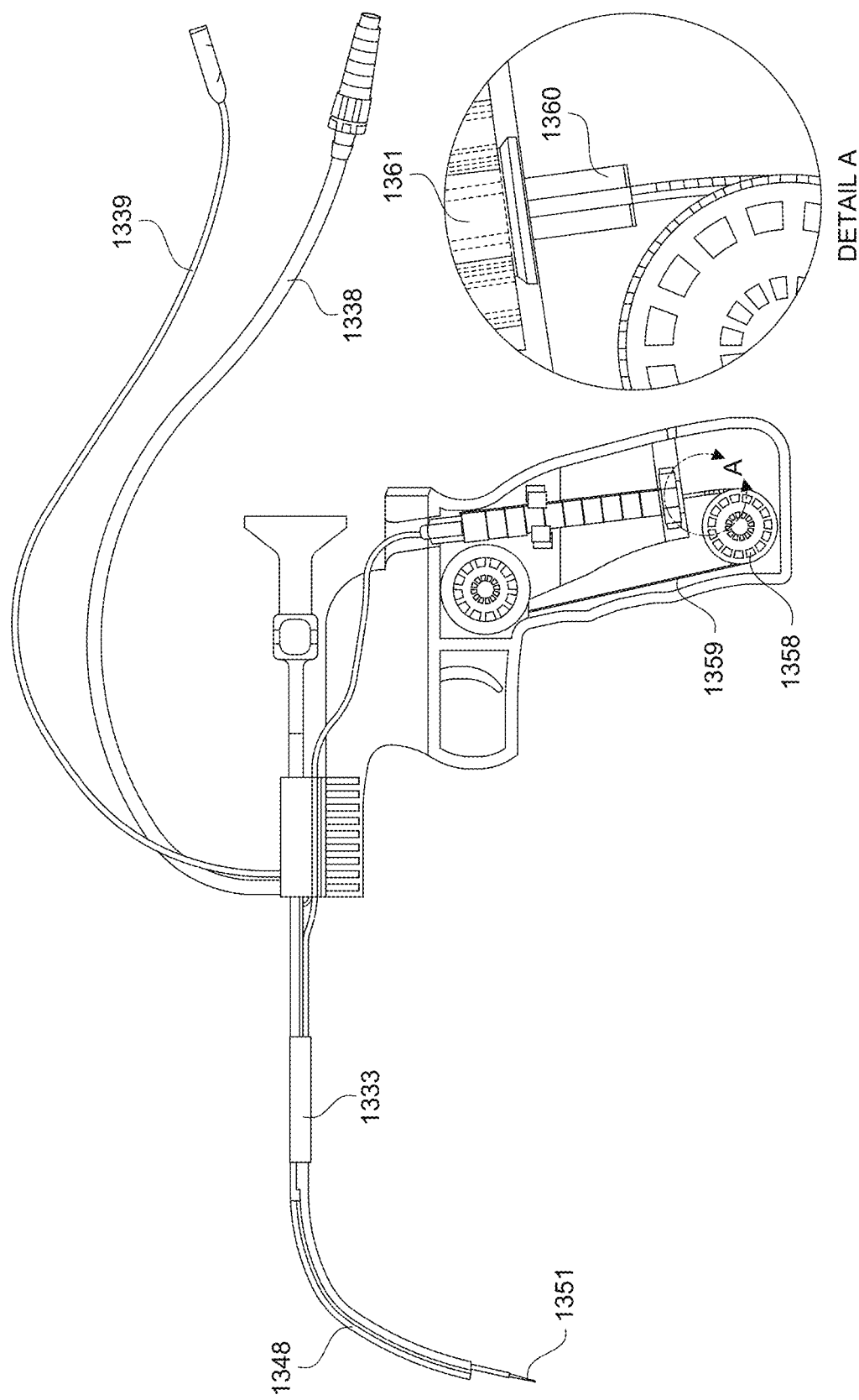
FIG. 37 shows a side view of an injection syringe gun with a coupled endoscope and suction and irrigation lines, in accordance with implementations of the disclosure.
Figure 38:
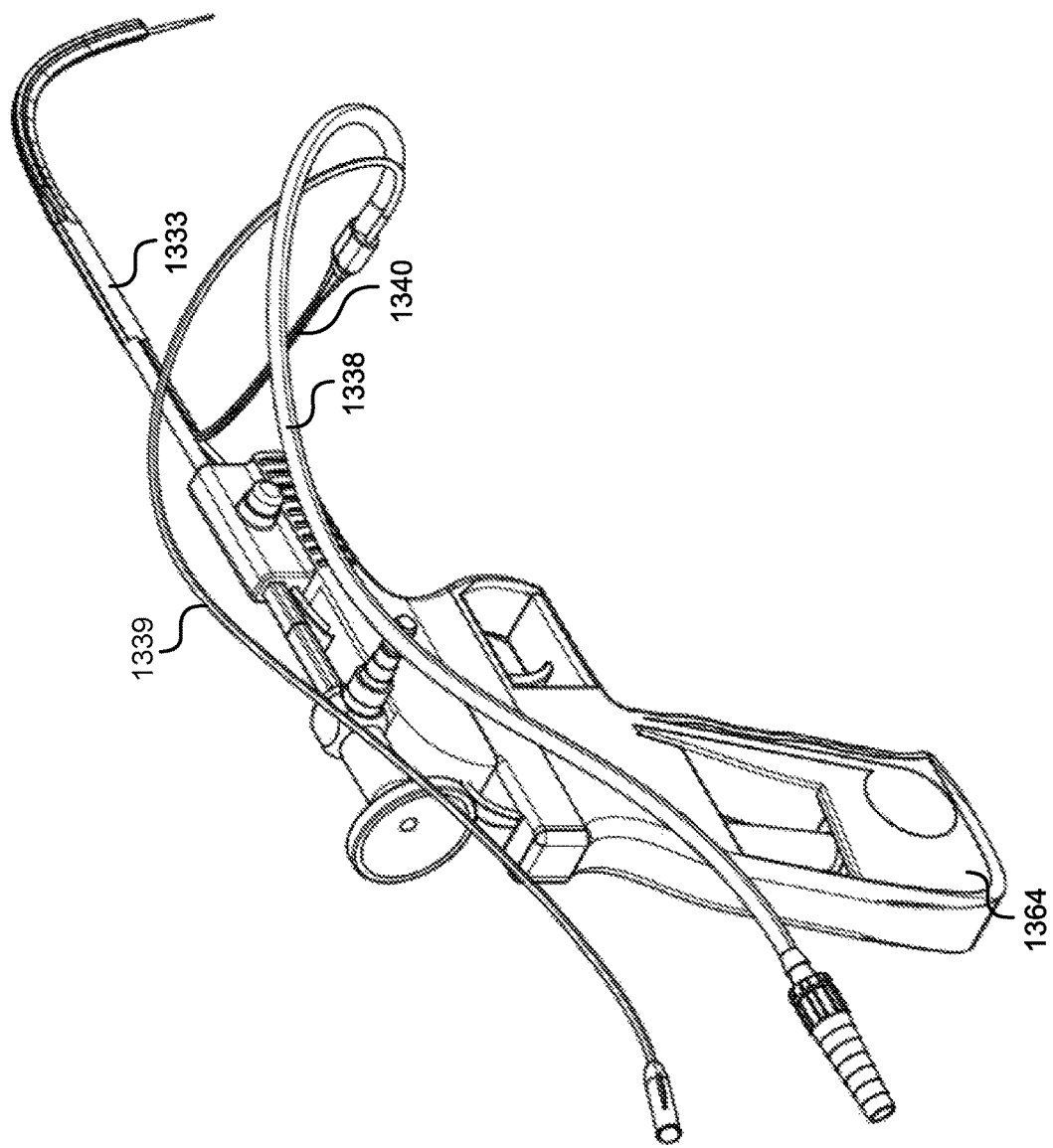
FIG. 38 shows a perspective view of the injection syringe gun of FIG. 37.
Figure 40:
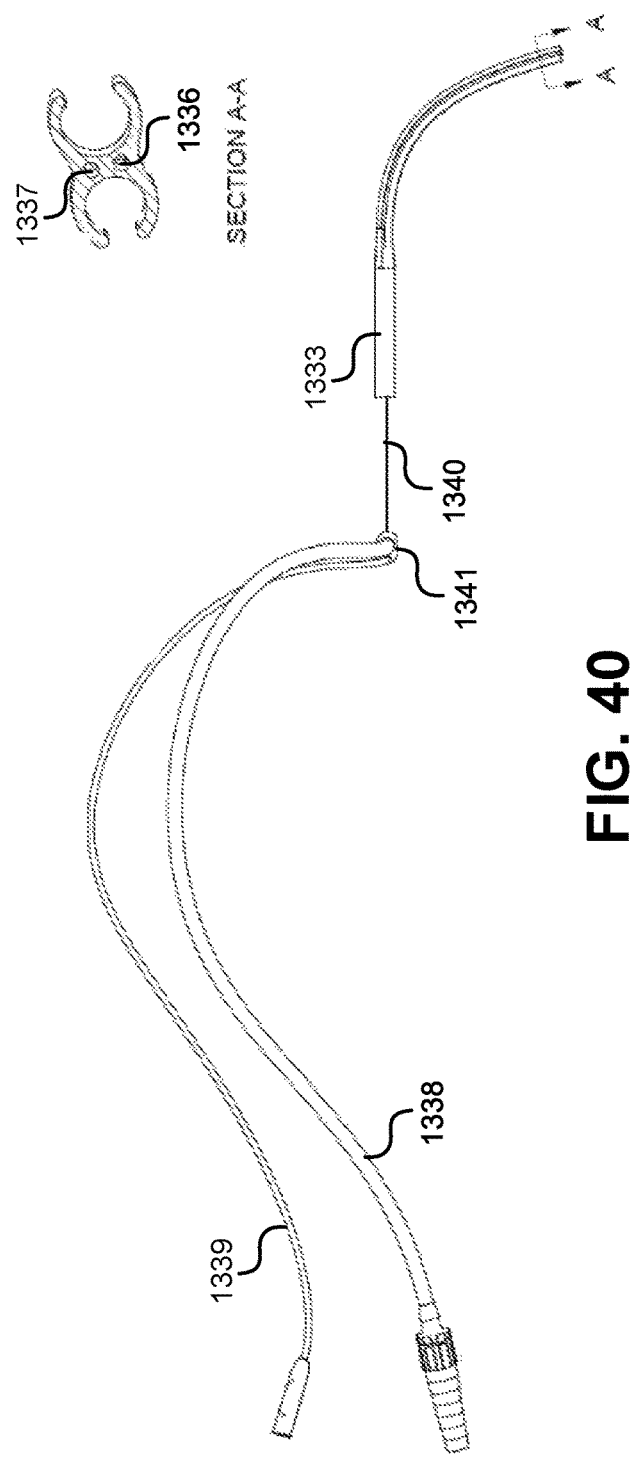
FIG. 40 shows a suction line and irrigation line assembly that may be coupled to a distal end of an instrument and endoscope in accordance with implementations of the disclosure.
Figure 41:
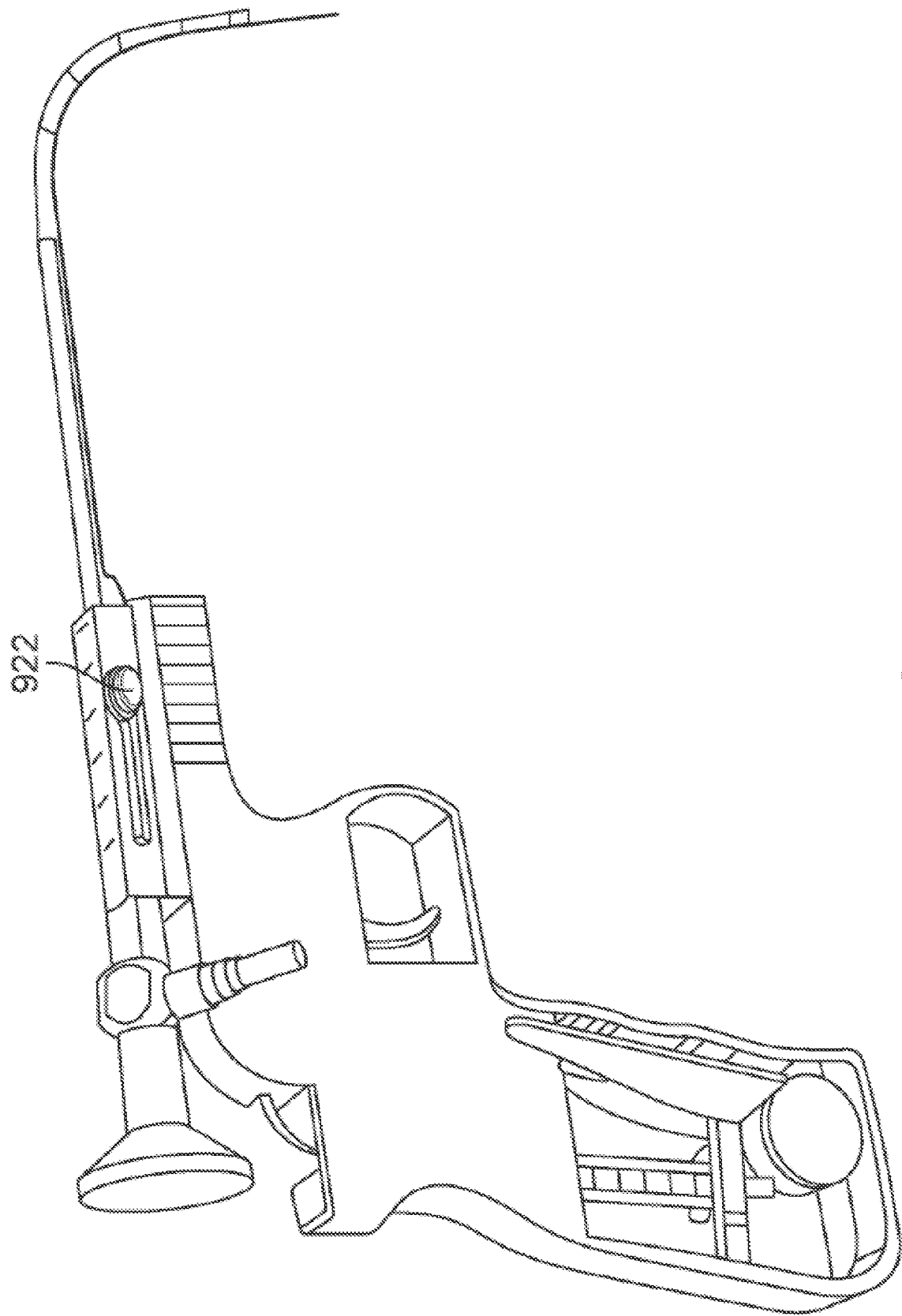
FIG. 41 shows a perspective view of another injection syringe gun, including a coupled endoscope, in accordance with implementations of the disclosure.
Figure 42:
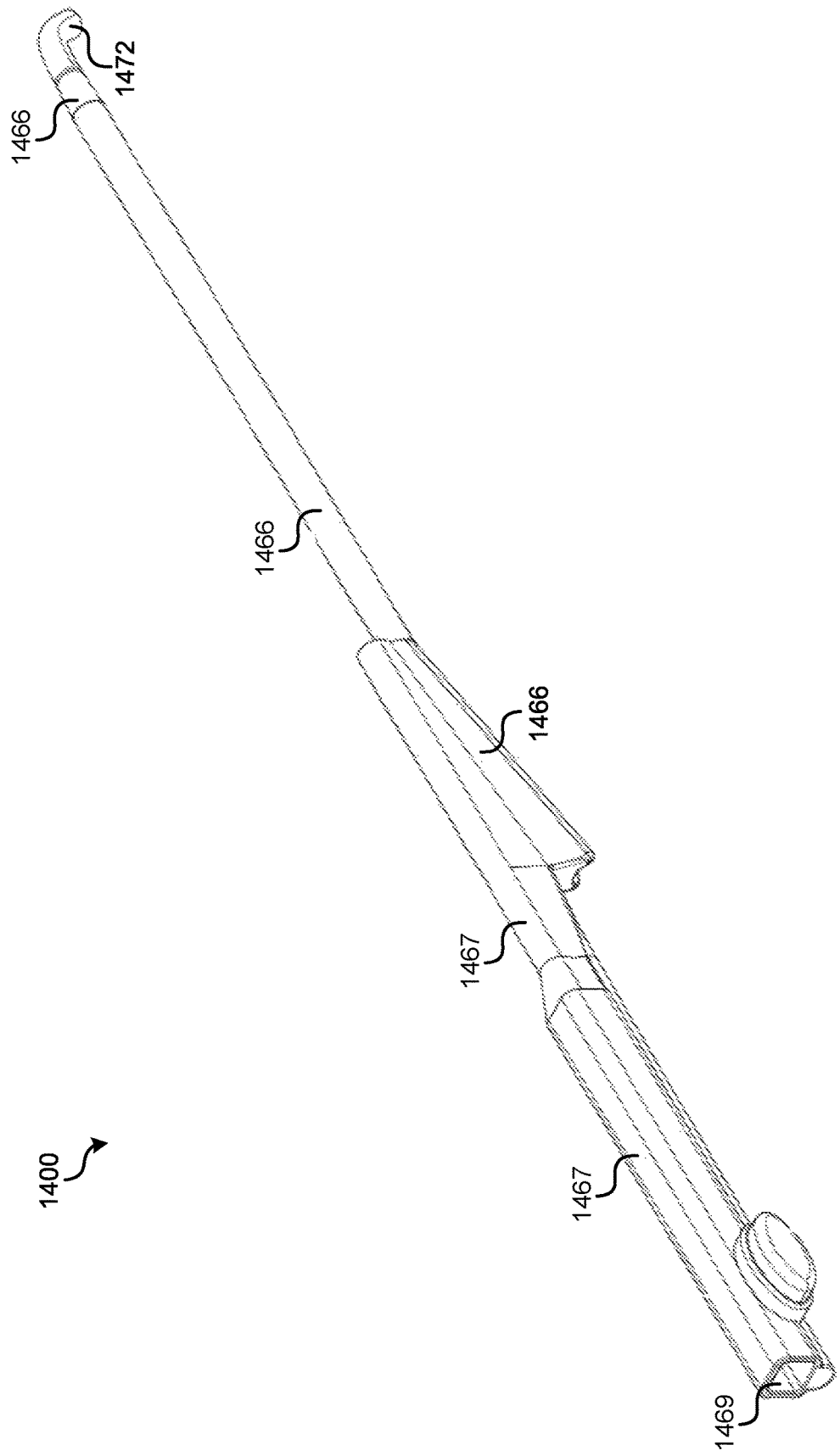
FIG. 42 shows a perspective view of an endoscopic Eustachian tube balloon dilator, including an insert ratchet mechanism for coupling an endoscope, in accordance with implementations of the disclosure.
Figure 43:
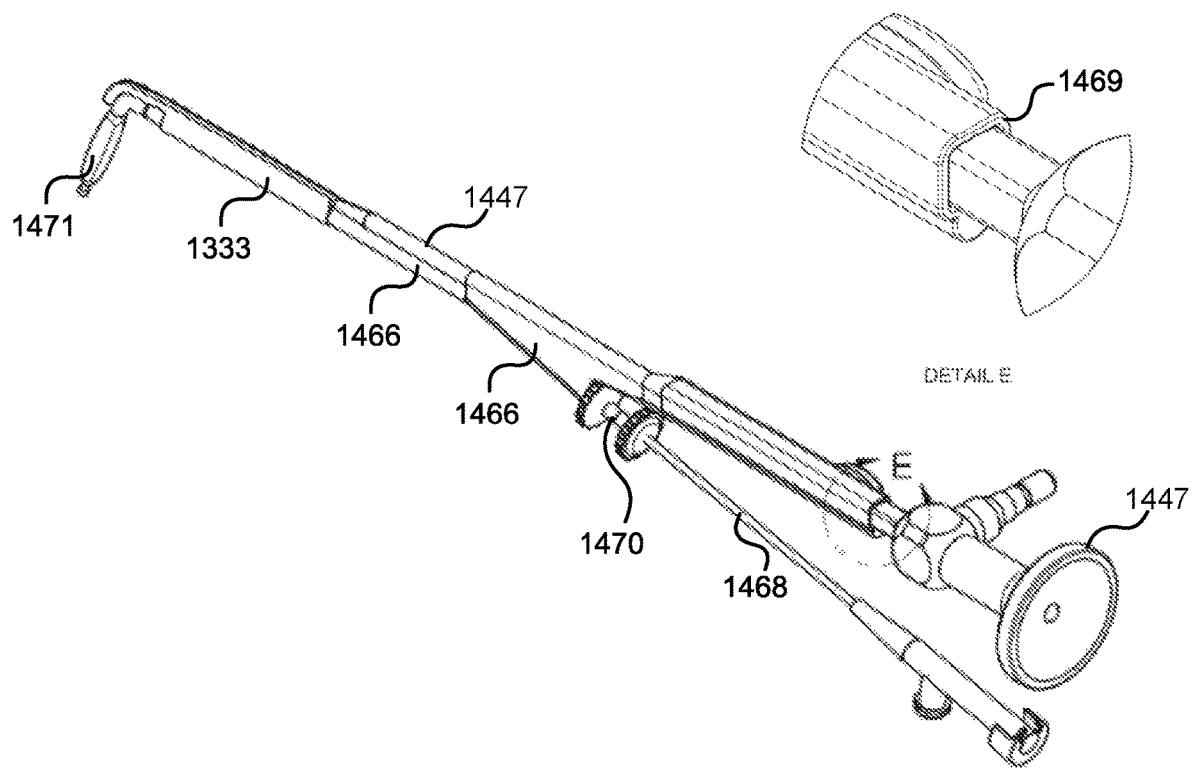
FIG. 43 shows a perspective view of the endoscopic Eustachian tube balloon dilator of FIG. 42 with a coupled endoscope and balloon catheter, in accordance with implementations of the disclosure.
Figure 44:
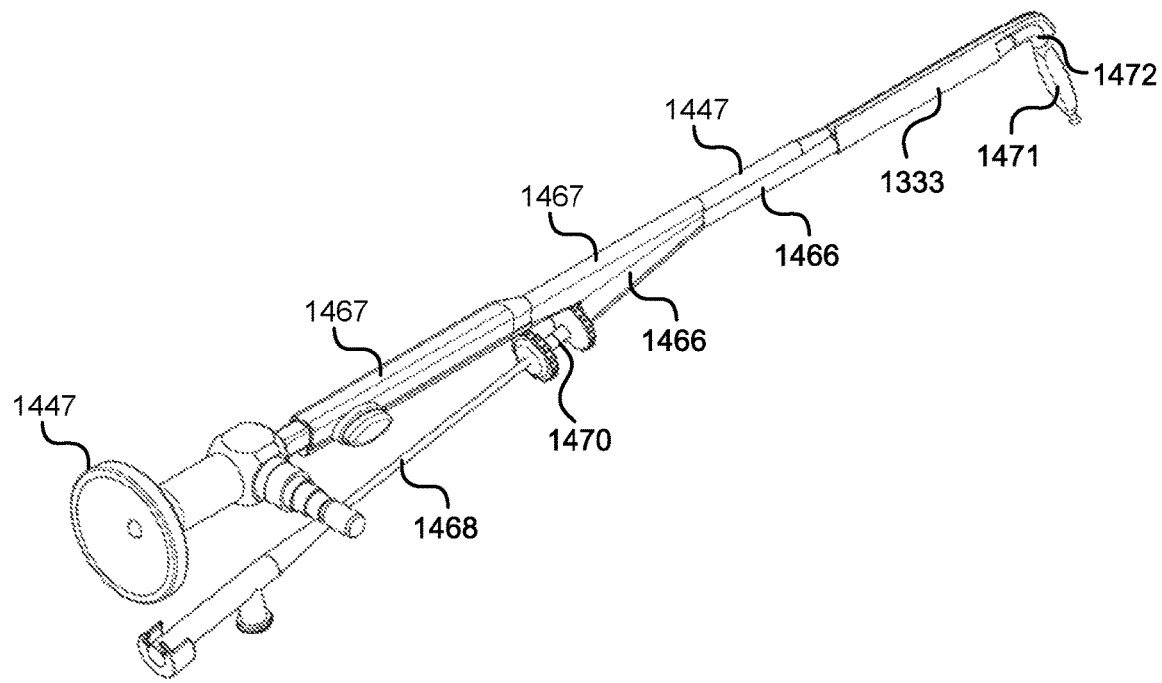
FIG. 44 shows a perspective view of the endoscopic Eustachian tube balloon dilator of FIG. 42 with a coupled endoscope and balloon catheter, in accordance with implementations of the disclosure.
Figure 45:
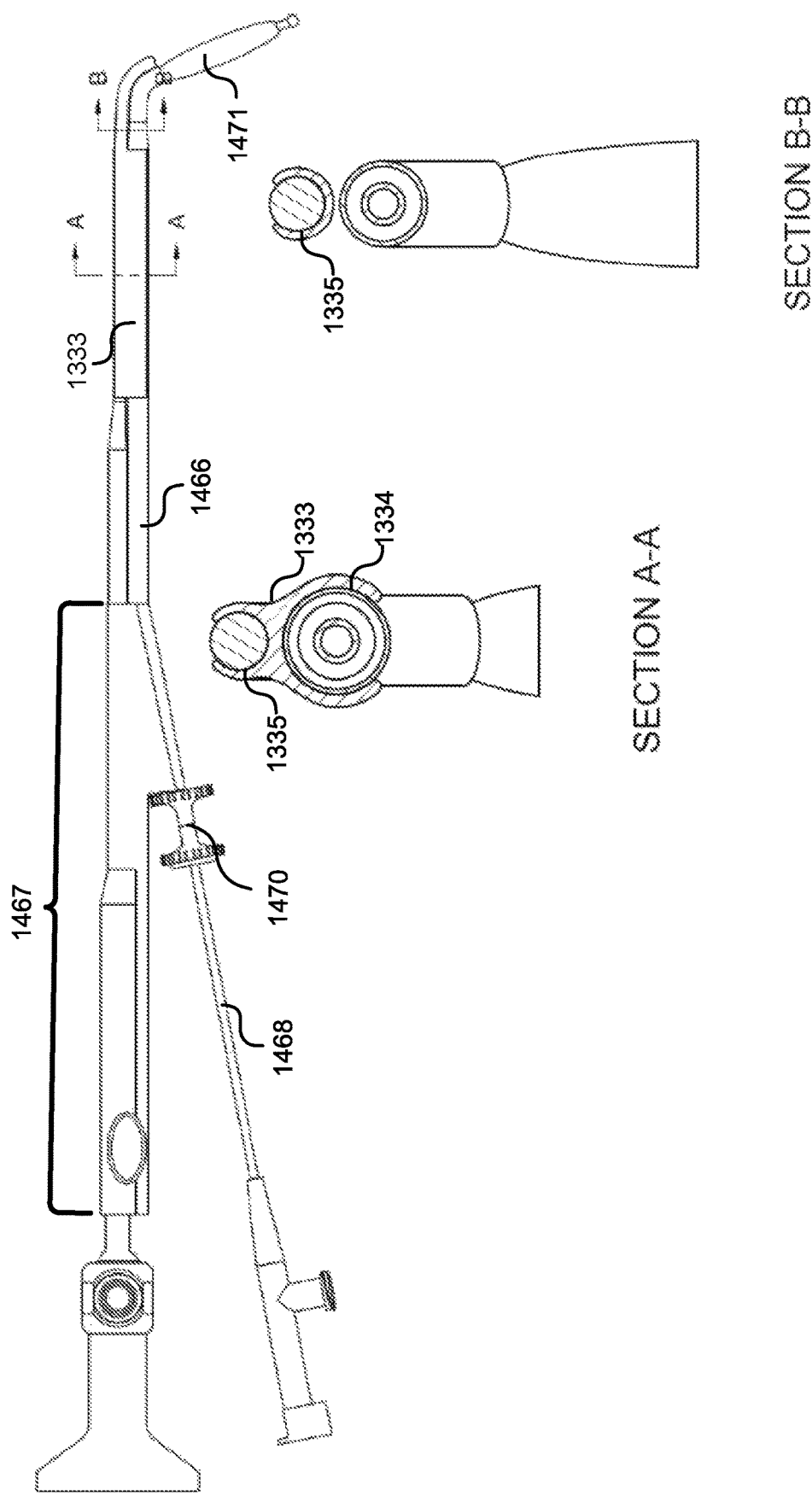
FIG. 45 shows a side view of the endoscopic Eustachian tube balloon dilator of FIG. 42 with a coupled endoscope and balloon catheter, in accordance with implementations of the disclosure.

In another implementation, illustrated by FIGS. 37-38, 40, 43-47, and 62, a removable, firm or flexible, reusable or disposable, insert 1333 may be adaptable and/or customized to each distal instrument shaft length, curvature, and shape. The removable insert may have two channel grooves 1334 and 1335 that may act as elongated clasps that respectively fixate to the instrument shaft below groove 1334 and the flexible (and in some implementations, part of the rigid) aspect of the hybrid endoscope above groove 1335 (or vice versa depending on the instrument design and application). Within the wall of such an insert, there may be incorporated one or more hollow channels through which suction 1336, 57 or irrigation 1337, 56 (FIGS. 40 and 62) could be delivered to the distal endoscope, lens, or instrument tool component. For example, FIGS. 37-38 and 40 depict a suction line 1338 and irrigation line 1339 that may attach proximally to the insert 1333. To minimize excess lines and entanglement, the irrigation and suction lines may converge at junction 1341 into a smaller caliper dual line 1340 that acts as one line extending from the detachable insert to a point away from the handle or proximal portion of the instrument.

Figure 62:
FIG. 62 shows an alternative location of the irrigation and suction ports within the connector of the suction line and irrigation line assembly of FIG. 40.
Figure 63:
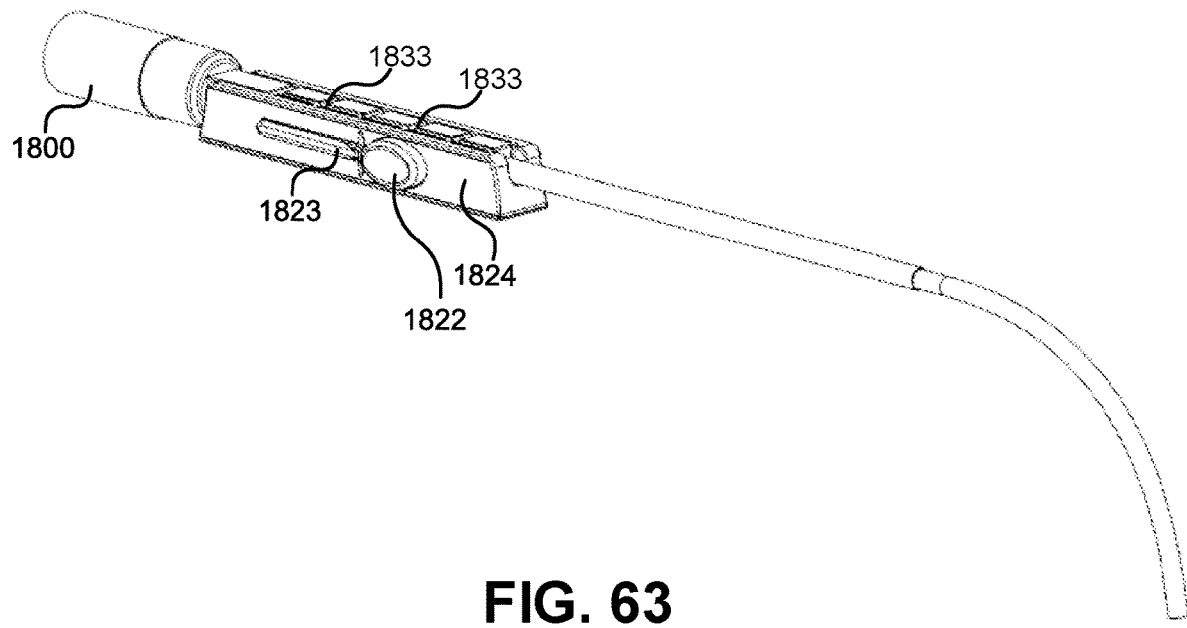
FIG. 63 shows a perspective view of another flexible-rigid hybrid endoscope included a levered top down ratchet mechanism for attaching the endoscope to an instrument, in accordance with implementations.
Figure 64:
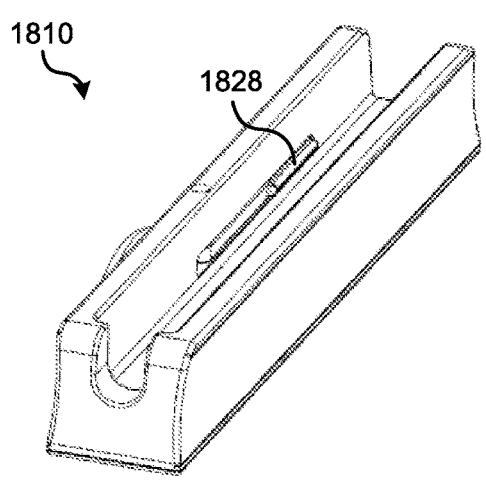
FIG. 64 shows a perspective view of a levered top down ratchet mechanism, in accordance with implementations.
Figure 65:
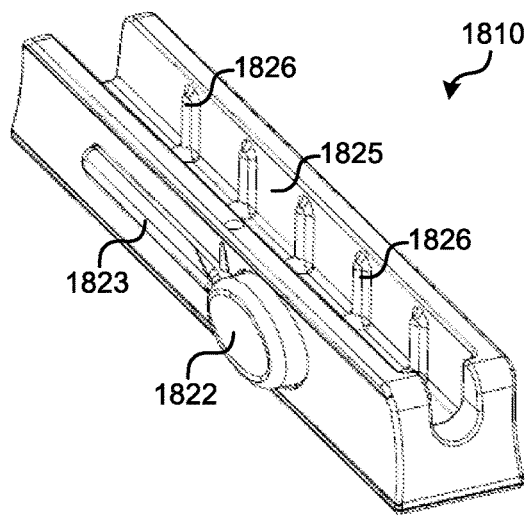
FIG. 65 shows another perspective view of the levered top down ratchet mechanism of FIG. 64.

For each of the attachment mechanisms for the flexible distal end of the endoscope, implementations may include a small hollow ring or cap 55 at the end point along the instrument shaft to help stabilize the flexible endoscope end tip, position the end tip for proper visualization of the patient's internal cavity and the instrument tool, and prevent further endoscope advancement. As illustrated by FIG. 62, suction and/or irrigation ports 56, 57 may be incorporated into the ring/cap mechanism to help clear the scope tip of secretions, blood, or other debris typically encountered during medical procedures.

Instruments

Implementations of the flexible-rigid endoscope described herein may be removably coupled to a variety of different instruments, further described below. The instruments described herein illustrate some examples. The tool portions of instruments to which the endoscopes described herein may be coupled to may include any number of surgical tools such as: graspers, cutters, biting forceps, scissors, balloons, needle injectors, cauteries, lasers, curettes, culture tools, suction tools, microdebriders, snares, staplers, fasteners, etc.

Additionally, it should be noted that in some implementations the instruments described herein may be coupled to other endoscopes besides the novel hybrid rigid-flexible endoscopes described herein. For example, the instruments described herein may be coupled to a rigid endoscope having both a rigid proximal end and a rigid distal end, or a flexible endoscope having both a flexible proximal end and a flexible distal end, to the extent to the endoscope is compatible with the instrument.

Laryngeal Forceps

In some implementations, the flexible-rigid endoscope described herein may be coupled to a laryngeal forceps instrument, implementations of which are illustrated by FIGS. 8-25 and 29-30. During use, a tool portion or shaft of the instrument may be inserted in the patient's mouth through the throat into a laryngeal cavity of the patient. For example, blades 619 of laryngeal forceps 600 may be positioned near tissue that needs to be removed. The positioning of the blades 619 of the forceps 600 directly in front of a lens 150 of an endoscope 100 may enable the physician to properly visualize the blades and laryngeal cavity as they contact the tissue. The physician may then actuate the handles 629 of the forceps 600 while viewing blades 619 as they grasp or cut tissue.

Sinus Forceps

Figure 26:
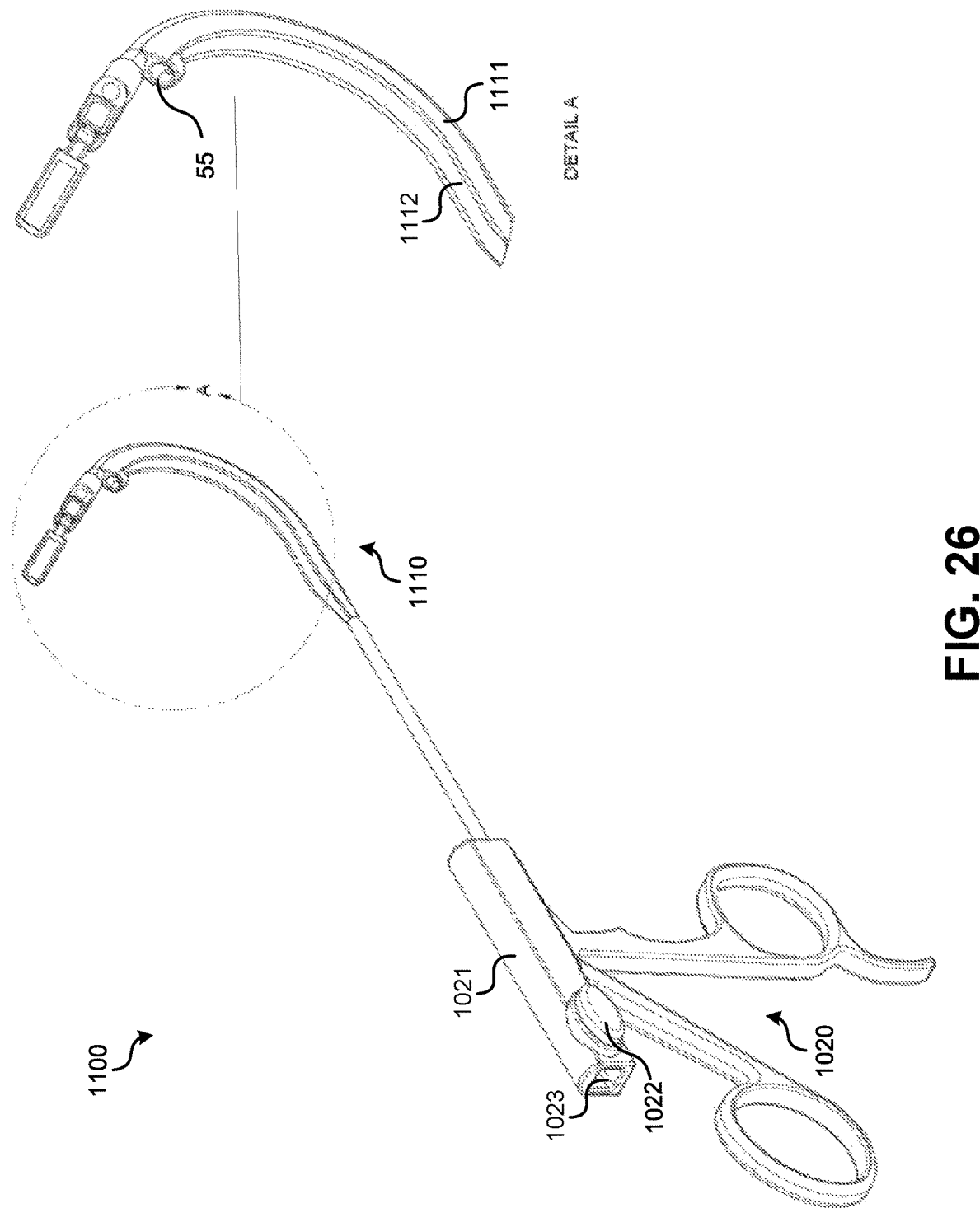
FIG. 26 shows a perspective view of a sinus forceps instrument, including an insert ratchet attachment mechanism, that an endoscope may couple to, in accordance with implementations of the disclosure.
Figure 27:
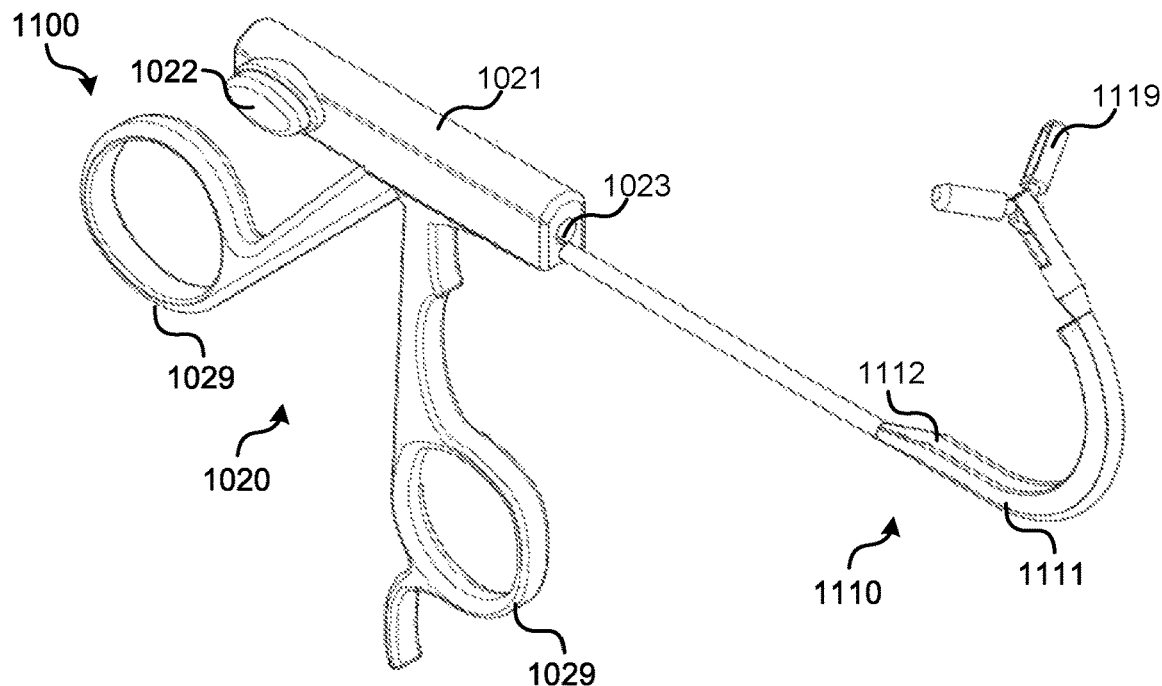
FIG. 27 shows another perspective view of the sinus forceps instrument of FIG. 26.
Figure 28:
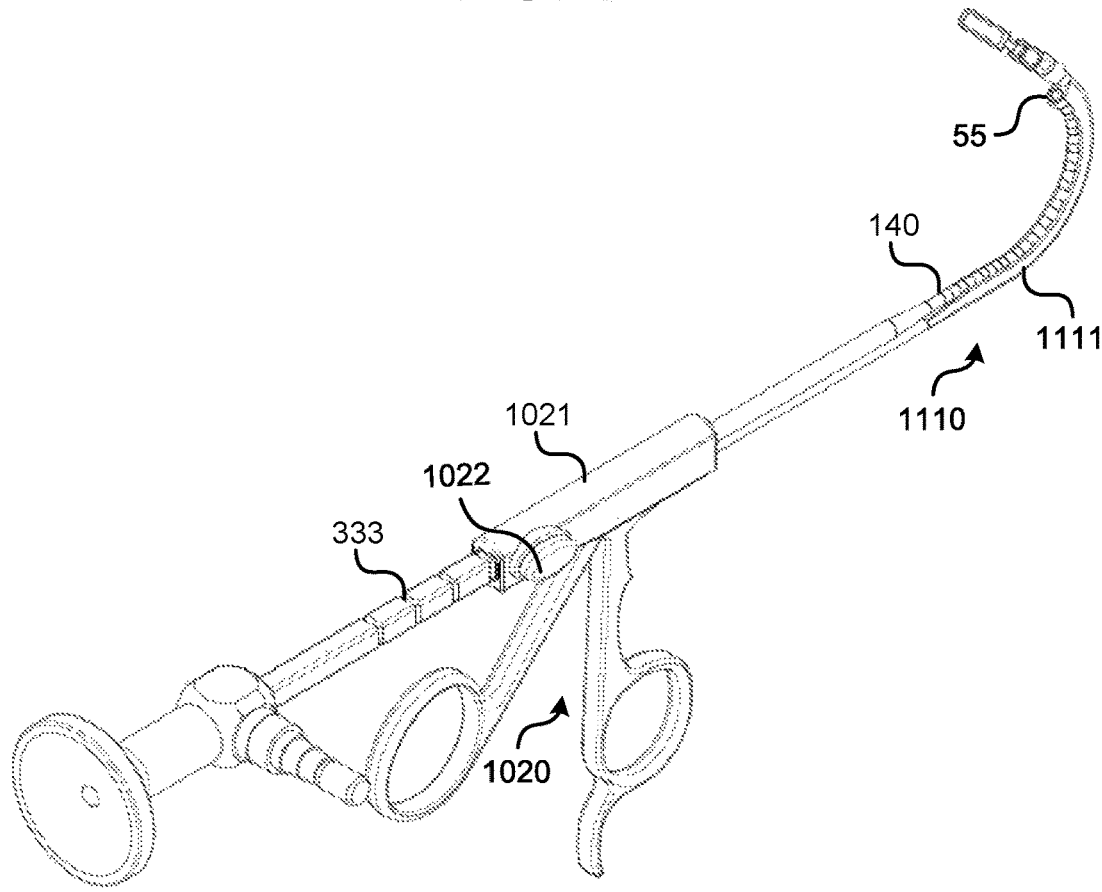
FIG. 28 shows a perspective view of the sinus forceps instrument of FIG. 26, including a coupled endoscope.
Figure 29:
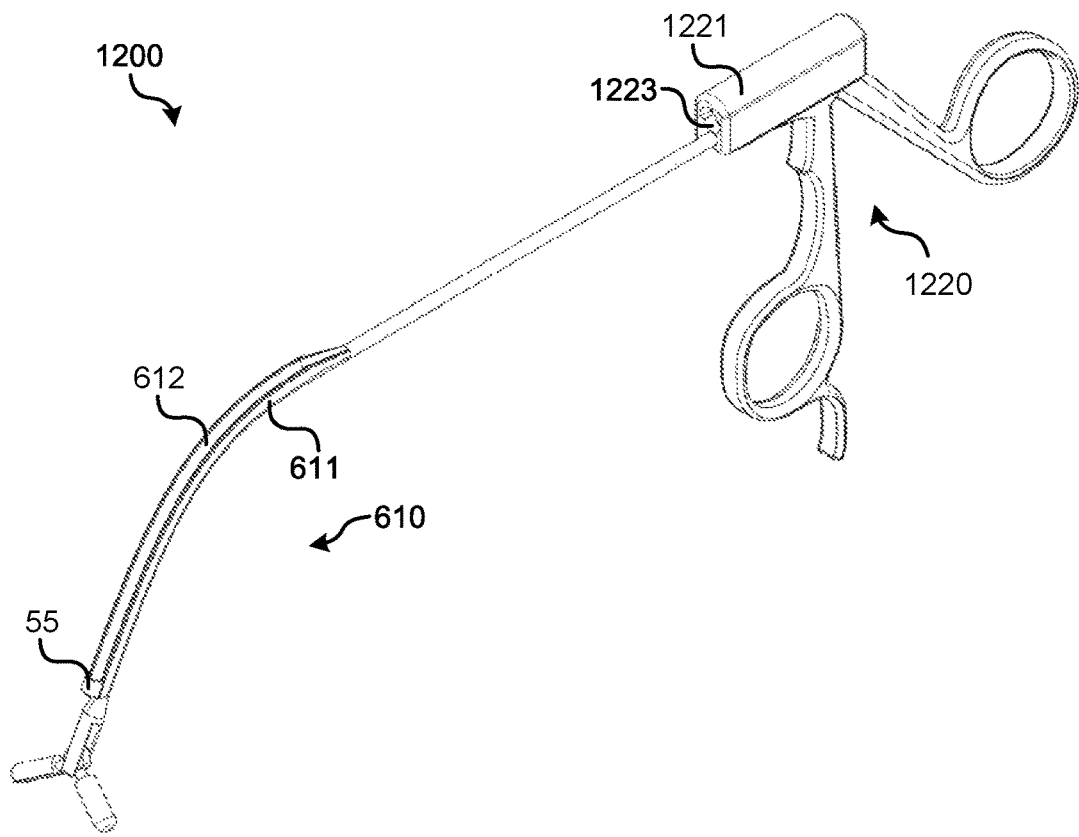
FIG. 29 shows a perspective view of a laryngeal forceps instrument, including an insert twist mechanism, that an endoscope may couple to, in accordance with implementations of the disclosure.
Figure 30:
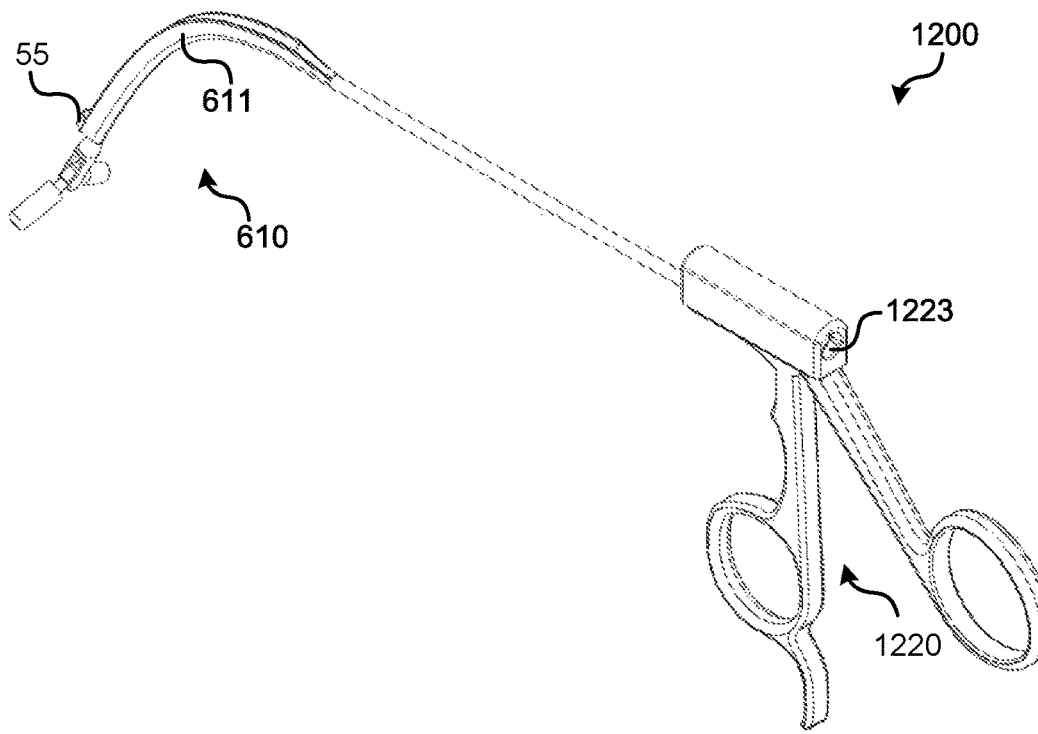
FIG. 30 shows another perspective view of the laryngeal forceps instrument of FIG. 29.
Figure 31:
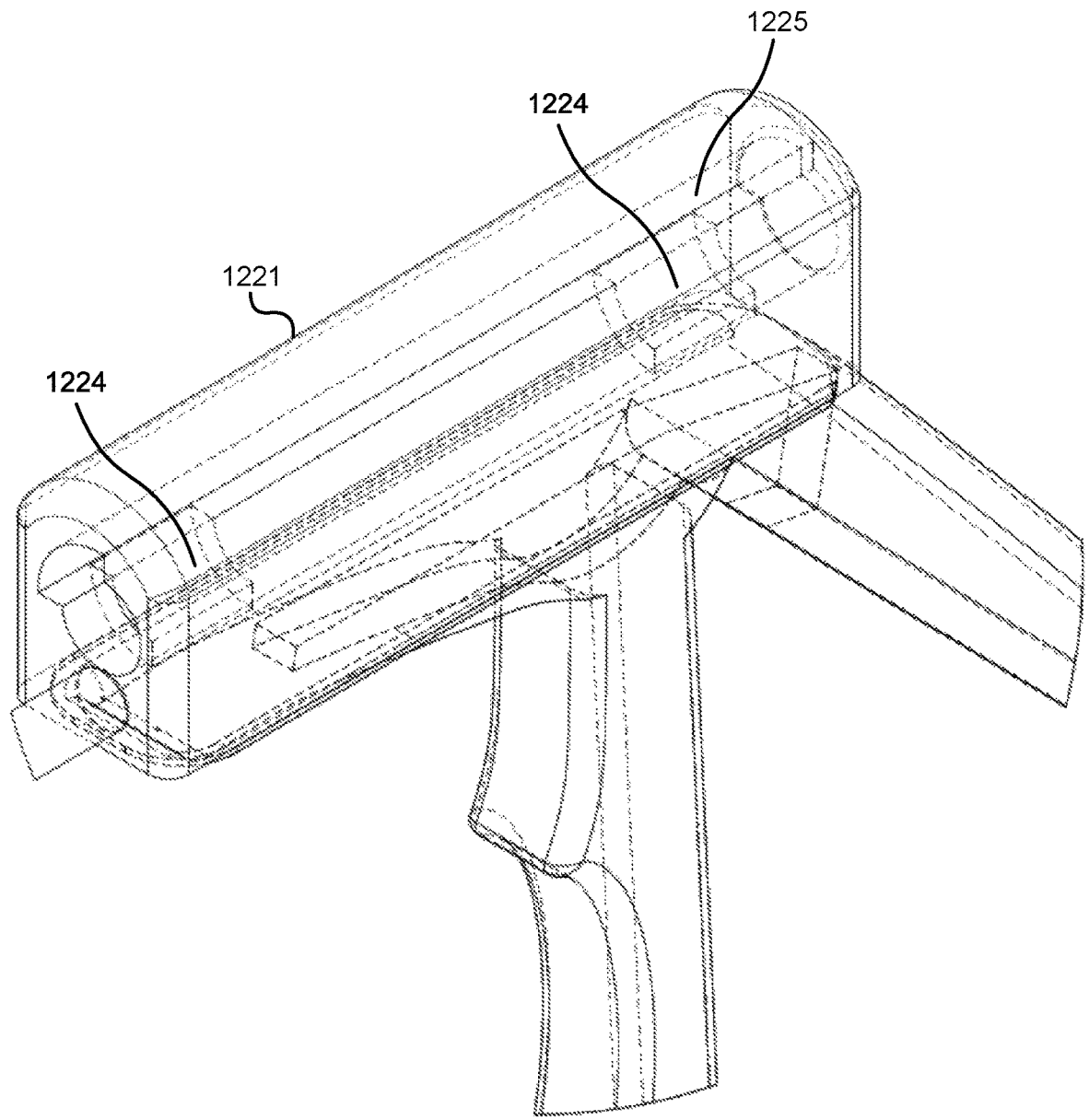
FIG. 31 shows internal components of an insert twist mechanism for coupling an endoscope to an instrument, in accordance with implementations of the disclosure.
Figure 33:
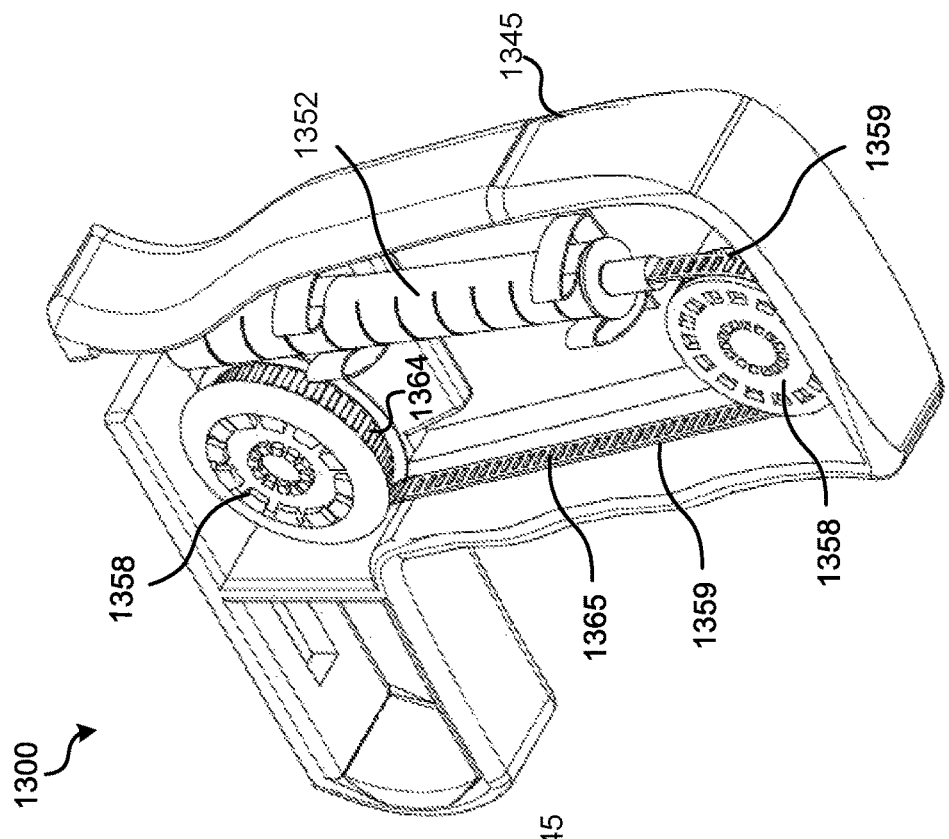
FIG. 33 shows another perspective view of the injection syringe gun of FIG. 32.
Figure 32:
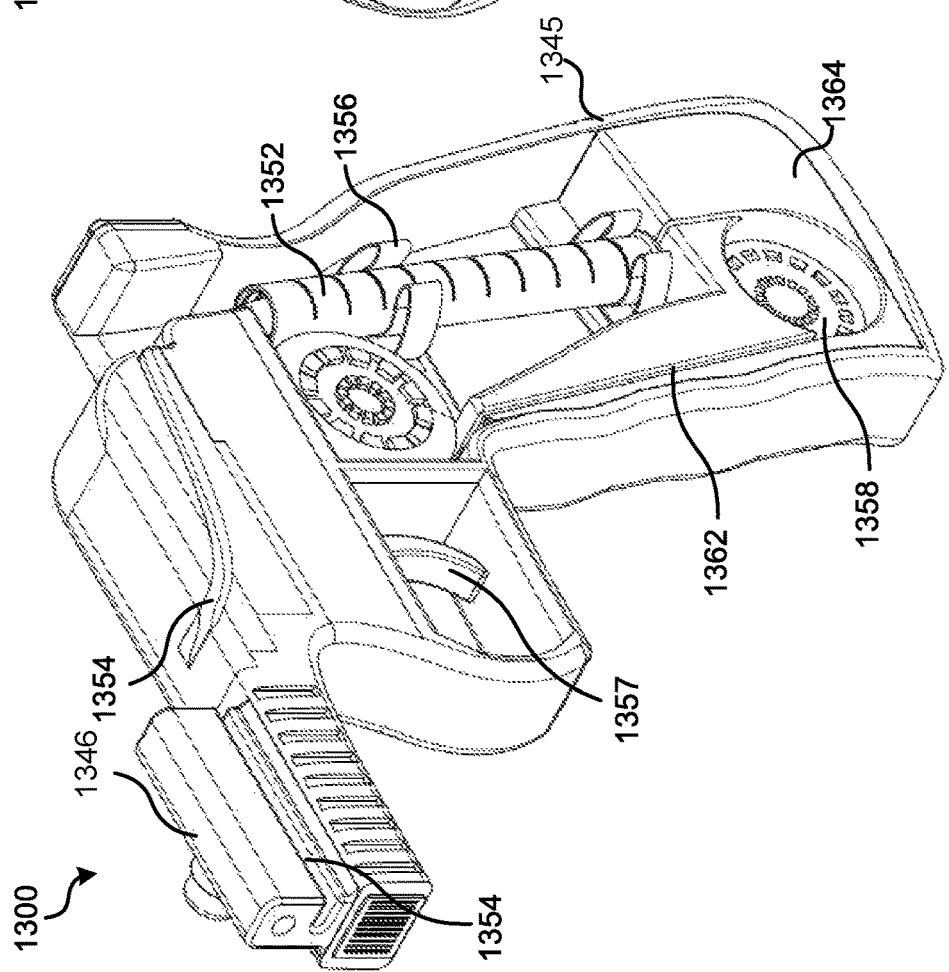
FIG. 32 shows a perspective view of an injection syringe gun, including a mechanism for coupling an endoscope, in accordance with implementations of the disclosure.
Figure 34:
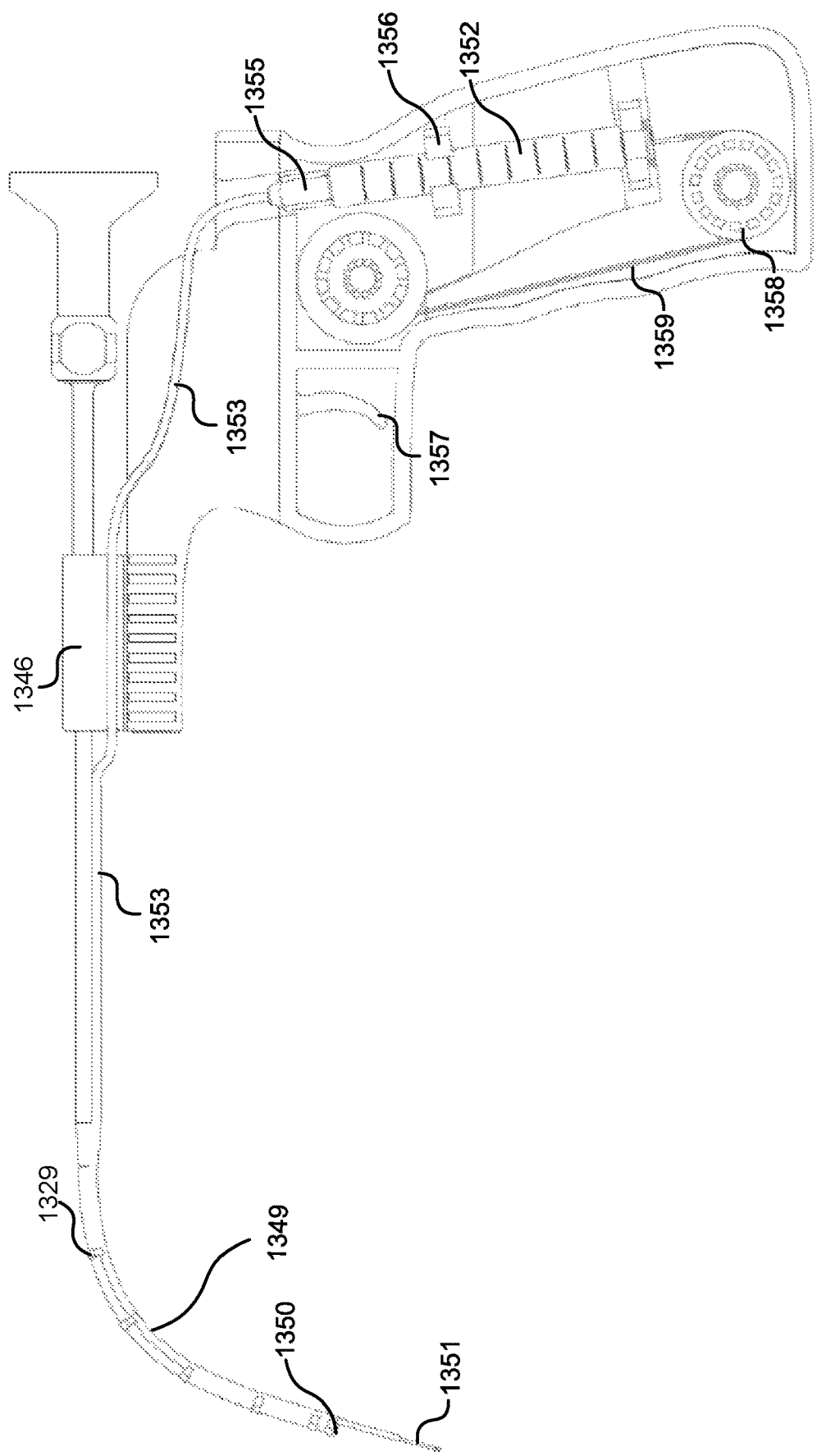
FIG. 34 shows a side view of the injection syringe gun of FIG. 32, including a coupled needle and endoscope, in accordance with implementations of the disclosure.
Figure 35:
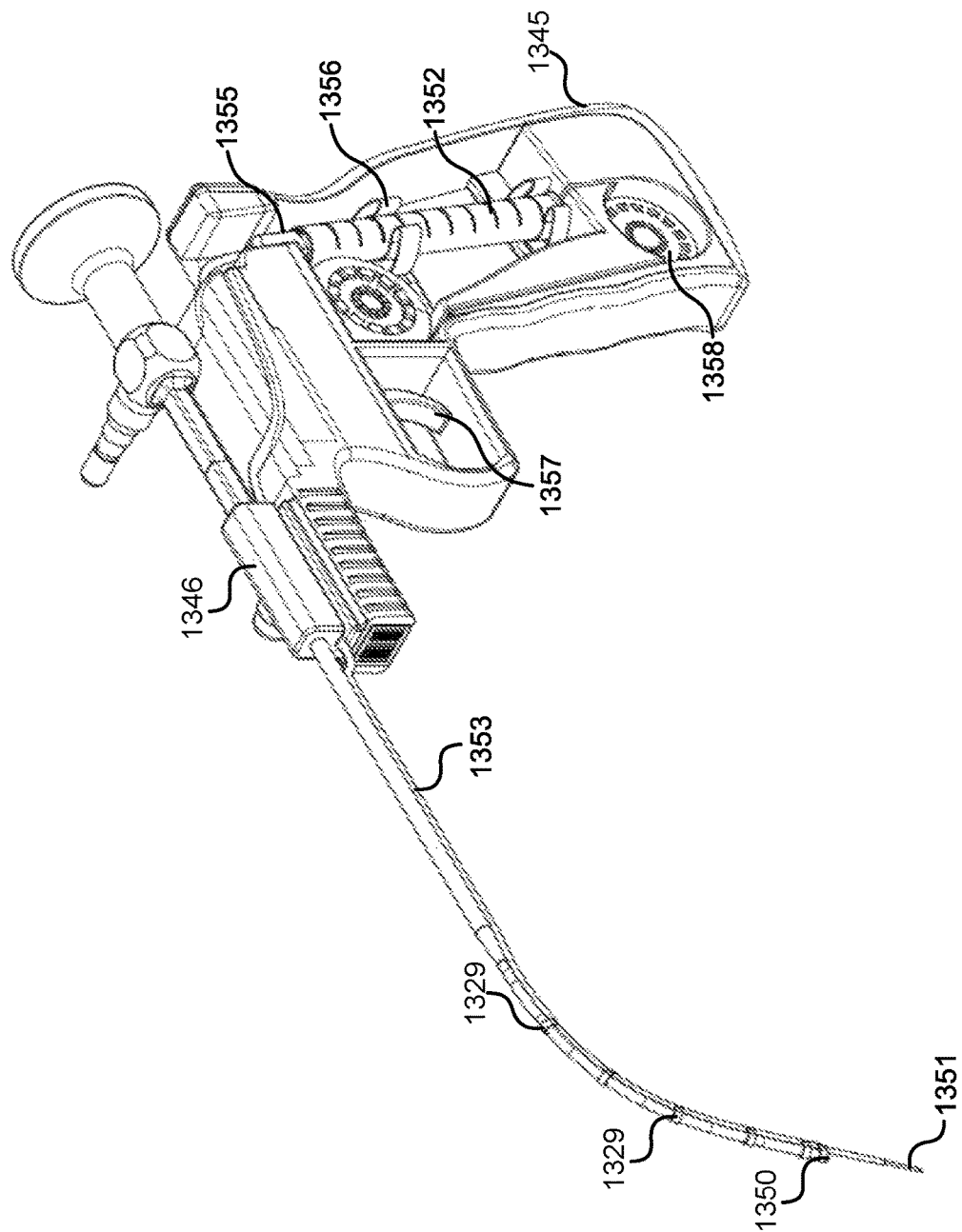
FIG. 35 shows a perspective view of the injection syringe gun of FIG. 32, including a coupled needle and endoscope, in accordance with implementations of the disclosure.

In some implementations, the flexible-rigid endoscope described herein may be coupled to a sinus forceps instrument, implementations of which are illustrated by FIGS. 26-28. During use, a tool portion or shaft of the instrument may be inserted through a nasal passage and into a sinus cavity of a patient. For example, blades 1119 of a forceps 1100 may be positioned near tissue within a maxillary sinus that needs to be removed. The positioning of the blades 1119 of the sinus forceps 1100 directly in front of a lens 150 of an endoscope 100 may enable the physician to properly visualize the blades and sinus cavity as they contact the tissue. The physician may then actuate the handles 1029 of the sinus forceps 1100 while viewing blades 1119 as they grasp or cut tissue.

Laryngeal Syringe Gun

Example implementations of an injection syringe gun 1300 for endoscopic, office-based injection (e.g., vocal cord injection) are illustrated by FIGS. 32-41. As illustrated, an exterior portion of syringe gun 1300 may include a gun handle 1345 for holding the instrument, a trigger mechanism 1357, an endoscope attachment mechanism 1346, and one or more grooves or channels 1354 for routing a needle 1353. An interior portion of syringe gun 1300 may include a syringe 1352, connector 1355, clips 1356 to hold syringe 1352, wheels 1358, band 1359, plunger 1360, and rubber stopper 1361.

Figure 36:
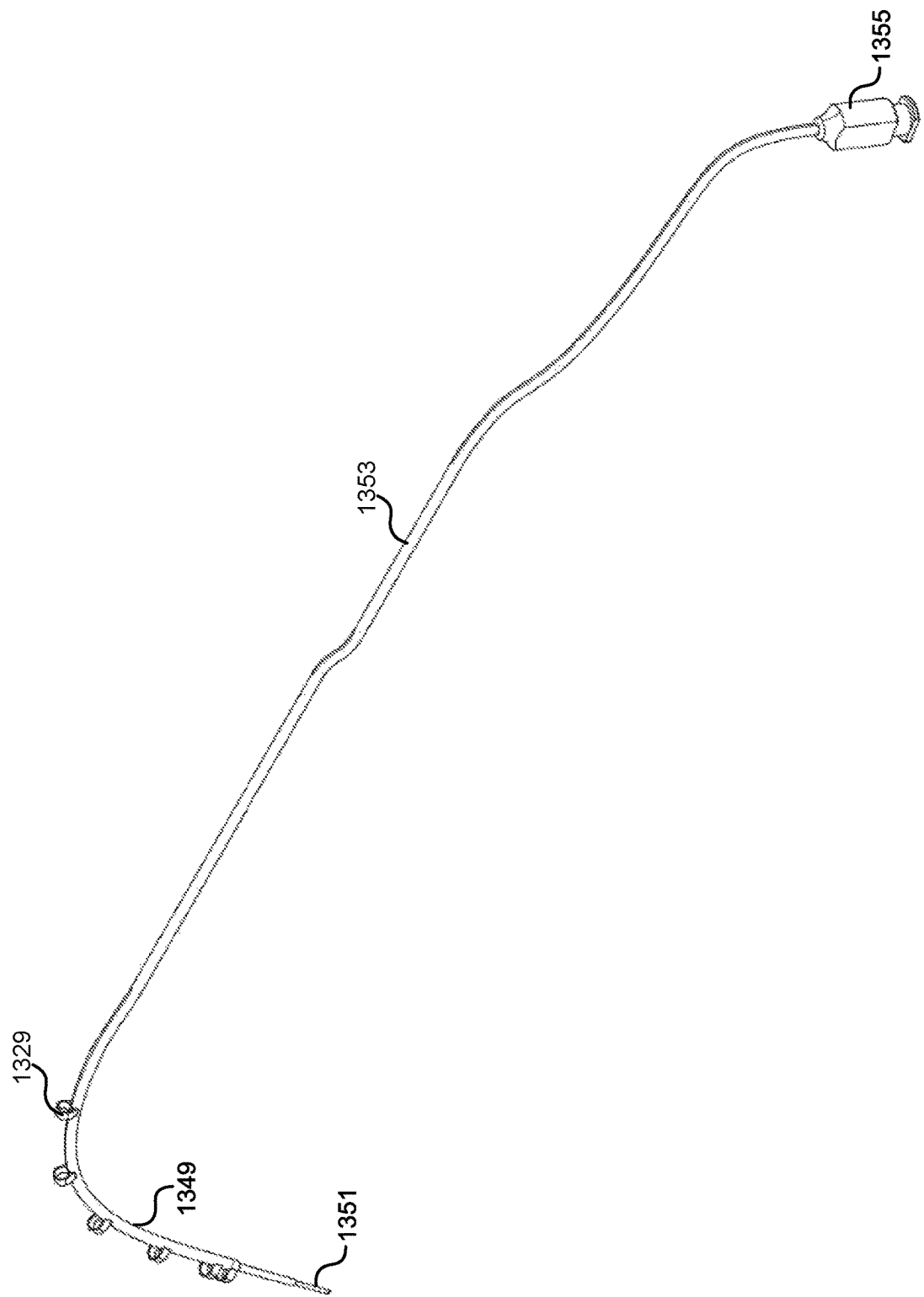
FIG. 36 shows a perspective view of a needle, including rings for securing a distal end of an endoscope that may be used with an injection syringe gun in accordance with implementations of the disclosure.
Figure 39:
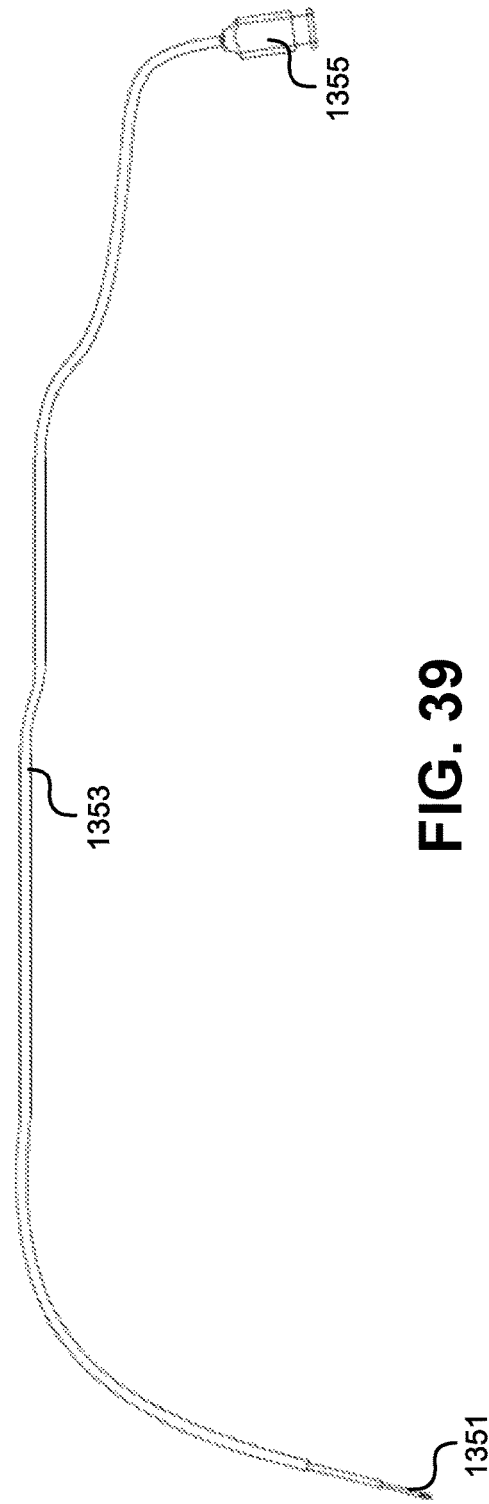
FIG. 39 shows a perspective view of a needle that may be used with an injection syringe gun, in accordance with implementations of the disclosure.

As illustrated by FIGS. 36 and 39, an injection needle 1353 used with syringe gun 1300 may be a pre-bent or malleable needle configured to accommodate the shape and contour of the syringe gun 1300 and flexible distal end of an endoscope. The needle 1353 may be connected to a syringe via connector 1355. During configuration, the syringe 1352 and needle 1353 may be locked into place in syringe gun 1300 by depressing the syringe into a series of clips 1356 and the needle 1353 into a groove 1354 incorporated into a top portion of the syringe gun. Syringe 1352 may be filled with local anesthetic, hydroxyl-appetite paste, or some other liquid or substance injected at the procedure site (e.g., vocal cords) by needle tip 1351.

After the syringe and needle are secured in place, a flexible-rigid hybrid scope may be inserted or otherwise attached to the gun handle at endoscope attachment mechanism 1346. In the illustrated examples of FIGS. 34-35 and 37-38, an endoscope attaches to a top portion gun 1300 to endoscope attachment mechanism 1346 in a manner similar to the insert ratchet mechanism described above. In the illustrated example of FIG. 41, the endoscope attaches to a portion of the gun to an endoscope attachment mechanism in a manner similar to top down ratchet mechanism described above with reference to FIG. 21. Other attachment mechanisms to attach the endoscope to the syringe gun may be used. A flexible distal end 1348 of an endoscope may follow the curvature of the needle shaft 1349 such that an objective lens 1350 situated at the end of flexible distal end 1348 is positioned in close proximity to the needle tip 1351. The flexible portion of the scope, in one embodiment (e.g., FIGS. 34-36), may be threaded through a series of metal loops 1329 attached to the fabricated needle 1353. As alluded to above, other implementations for attaching the distal scope to the needle are envisioned. In the illustrated configurations, direct visualization of needle tip 1351 as it enters the sub-mucosal tissue may be made possible via the attached hybrid flexible-rigid endoscope.

Once all components of syringe gun 1330 are assembled, the syringe gun with the coupled endoscope may be held with and positioned with one hand while the other hand is used to stabilize and protract the tongue or perform some other operation. The trigger mechanism 1357, when activated, may rotate one or two circular wheels 1358 coupled to a thin, firm, and flexible band or belt 1359 (e.g., a metallic band). At a distal end of the band (after it loops around the second bottom wheel), the band is coupled to a cylindrical metal plunger 1360 (FIG. 37) positioned directly opposite and in contact with a rubber stopper 1361 incorporated within syringe 1352 at an end opposite the needle attachment. Each time the trigger is depressed, plunger 1360 may advance a predetermined distance into the syringe, causing the rubber stopper 1361 within the syringe 1352 to move proximally, thereby dispensing a predetermined amount of a substance (e.g., approximately 0.1 cc) through needle tip 1351 into the injection site (e.g., laryngeal tissue).

One or both of the wheels 1358 around which the band passes may be motorized and may include teeth 1364 to interact with perforations 1365 along the length of the band 1359 to prevent slippage. The band 1359 may pass through a narrow stabilizing groove 1362 within the handle of the syringe gun. The groove 1362 may be incorporated in a firm plastic or machine tooled metal substance of a handle piece 1364. In implementations, a top part of the syringe gun 1300 may include a battery compartment housing one or more batteries (e.g., to power the motor for rotating the wheels) just underneath the syringe needle and endoscope attachment.

After use, syringe 1352 and needle 1353 may be disposed of, and syringe gun 1300 may be reused with a new syringe and needle during a subsequent procedure. Other mechanically activated injection mechanisms are also envisioned.

Endoscopic Eustachian Tube Balloon Dilator

The flexible-rigid hybrid endoscope described herein may be removably coupled to any number of balloon catheter devices, including those used for Eustachian tube, sinus, tracheal, and esophageal stricture dilation. Present balloon dilatation devices that are on the market require a surgeon to insert the balloon dilation catheter and the endoscope into a body cavity, separate from one another. This is problematic as it requires two hands to control the two devices simultaneously and may increase the device profile in the body cavity.

FIGS. 42-45 and 68 illustrate an example endoscopic Eustachian tube balloon dilator 1400 that improves on these prior designs by providing a mechanism for removably coupling an endoscope as described herein. As illustrated, dilator 1400 may include a housing 1467 for insertion of endoscope, a hollow tubing balloon cannula 1466 (rigid, semi-rigid, malleable, or flexible) for insertion of a balloon catheter 1468, where cannula 1466 has a distal segment 1472. In implementations, housing 1467 may be fixedly or removably coupled to cannula 1466. A hybrid endoscope 1447 may be inserted through a proximal opening 1469 of housing 1467. In the illustrated example, housing 1469 includes an insert ratchet mechanism as described above for securing the endoscope. In other implementations, other mechanisms may be used to secure the endoscope to the dilator. For example, a top down ratchet mechanism as described above may be utilized (FIG. 68).

A stopper 1470 located along a shaft of the balloon catheter may provide an easy grip to advance the balloon through the sheath and help to limit over advancement of the balloon catheter. A separate firm or flexible connector 1333 may be used to secure the distal flexible segment of the endoscope to a curved, distal segment 1472 of the balloon cannula 1466. The illustrated dilator may allow for a one handed, one instrument technique that maximizes space utilization, patient comfort, and surgeon dexterity within a confined nasal cavity. Currently available sinus balloon catheters could also be adapted to attach to the hybrid scope in a manner similar to that depicted in FIGS. 42-45, e.g. Acclarent Aera®.

Endoscopic Tracheal Dilator

From time to time, a patient will present electively or emergently with airway distress related to inadvertent tracheostomy tube removal. When a tracheostomy tube is accidentally removed (decannulation), the stomal tract through which it was placed often contracts, thereby preventing reinsertion of the tracheostomy tube. Forceful attempts at tube reinsertion can result in trauma, bleeding, airway distress, and occasional passage of the tube into a soft tissue tract under the skin but outside of the tracheal lumen resulting in patient mortality. Established methods used to dilate a tracheal stomal stenosis currently utilize tapered Bougie dilators. Unfortunately, these Bougie dilators (e.g., Cook® Medical, Blue Rhino®) obstruct the airway during passage thereby compounding respiratory distress and patient anxiety. Current systems fail to visually confirm adequate positioning of the dilator within the tracheal lumen prior to dilation.

FIGS. 48-55 illustrate an example implementation of an endoscopic tracheal dilator that allows an operator to visually confirm proper positioning of a balloon dilator 1477 within the tracheal stoma and tracheal lumen prior to inflation. The dilator includes a top down ratchet mechanism 1535 for removably coupling a flexible-rigid hybrid endoscope to a balloon pump hand piece 1573 of the instrument. Mechanism 1535 may operate in a manner similar to the top down ratchet mechanism described above. For example, it may include spaced ridges 1536 that may be spaced at intervals corresponding to the spacing between consecutive slots of a rigid proximal attachment segment of an endoscope. During attachment, a button 1522 may be actuated to retract a bar that is configured to lock into a groove of the rigid proximal attachment segment of the endoscope. Although a top down ratchet attachment mechanism is illustrated in this example, other mechanisms may be used to removably couple an endoscope to the instrument. For example, an insertion ratchet mechanism as discussed above may be used.

The balloon pump hand piece 1573 may comprise a pump handle 1574 that, when actuated, pumps air or liquid (e.g., water or saline) through a flexible tube 1575 that couples to a connection 1576 at the base of the balloon pump handle 1573. Pressurized air or fluid may then be transmitted from the base of the pump handle connection 1576 through the flexible tube 1575 to a distal balloon 1577 circumferentially attached to a hollow inner cannula 1578. Pressure may be measured by a pressure gauge 1590 incorporated into the pump handle 1573 (e.g., the upper left portion in the example shown).

Just inferior to the gauge may be a button 1591 that, when actuated, may release the pressure from the balloon. The hollow inner cannula may have on its proximal end an opening 1583 (FIG. 54) through which the flexible distal end of the hybrid endoscope may be inserted and advanced until the tip of distal end exits the distal part 1579 of the hollow inner cannula. The distal end of the scope contained within the hollow inner cannula 1578 and balloon 1577 may be advanced through the tracheal stoma stricture (the area of soft tissue between the external skin and anterior tracheal wall) until the lumen of the trachea is visualized. Once proper positioning of the inner cannula within the trachea is confirmed, the endoscope may be withdrawn and the patient can continue to breathe through the hollow inner cannula 1578.

In this example, because the high-pressure balloon dilator is external to the hollow inner cannula 1578, the patient may continue to safely breath through the hollow inner cannula while the balloon is inflated by activating the pump handle. A small removable stopper 1584 (FIGS. 51-53) may be placed just proximal to the balloon 1577 in order to help manually stabilize the apparatus during inflation and to prevent inadvertent over advancement of the balloon or cannula within the airway. A small curved flexible spring 1585 may allow widening of the stopper clamp positioned on the hollow inner cannula 1587. Squeezing together the lateral projections 1586 on the stopper may activate the spring and allow the stopper 1584 to be removed from the cannula. Prior to attaching the flexible tube to the coupling at the base of the handle, a separate tracheostomy tube 1582 and 1595 may be advanced over the tubing such that the tubing passes completely through the lumen of the tracheostomy tube.

For this implementation, a #4 tracheostomy tube may be used, although any tracheostomy tube with an inner diameter small enough to accommodate the caliber of the flexible tubing and the hollow inner cannula may be used. Once the stoma is dilated with the balloon, the stopper clamp 1584 may be removed and the tracheostomy tube advanced over the flexible tubing and inner cannula, through the dilated stoma, and into the tracheal lumen. The tube may then be secured to prevent inadvertent decannulation.

Figure 55:
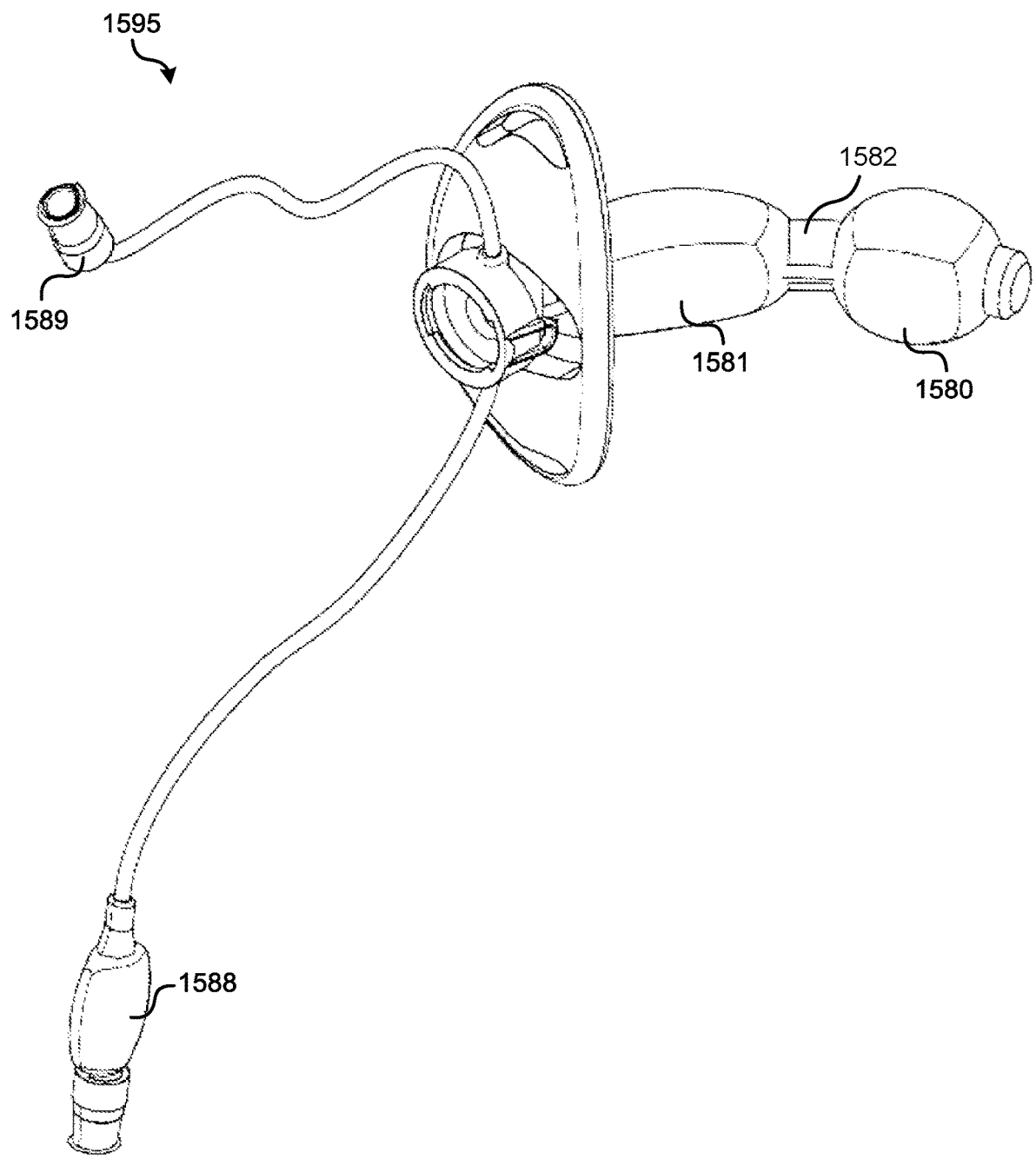
FIG. 55 shows a dilating tracheostomy tube, in accordance with implementations of the disclosure.
Figure 56:
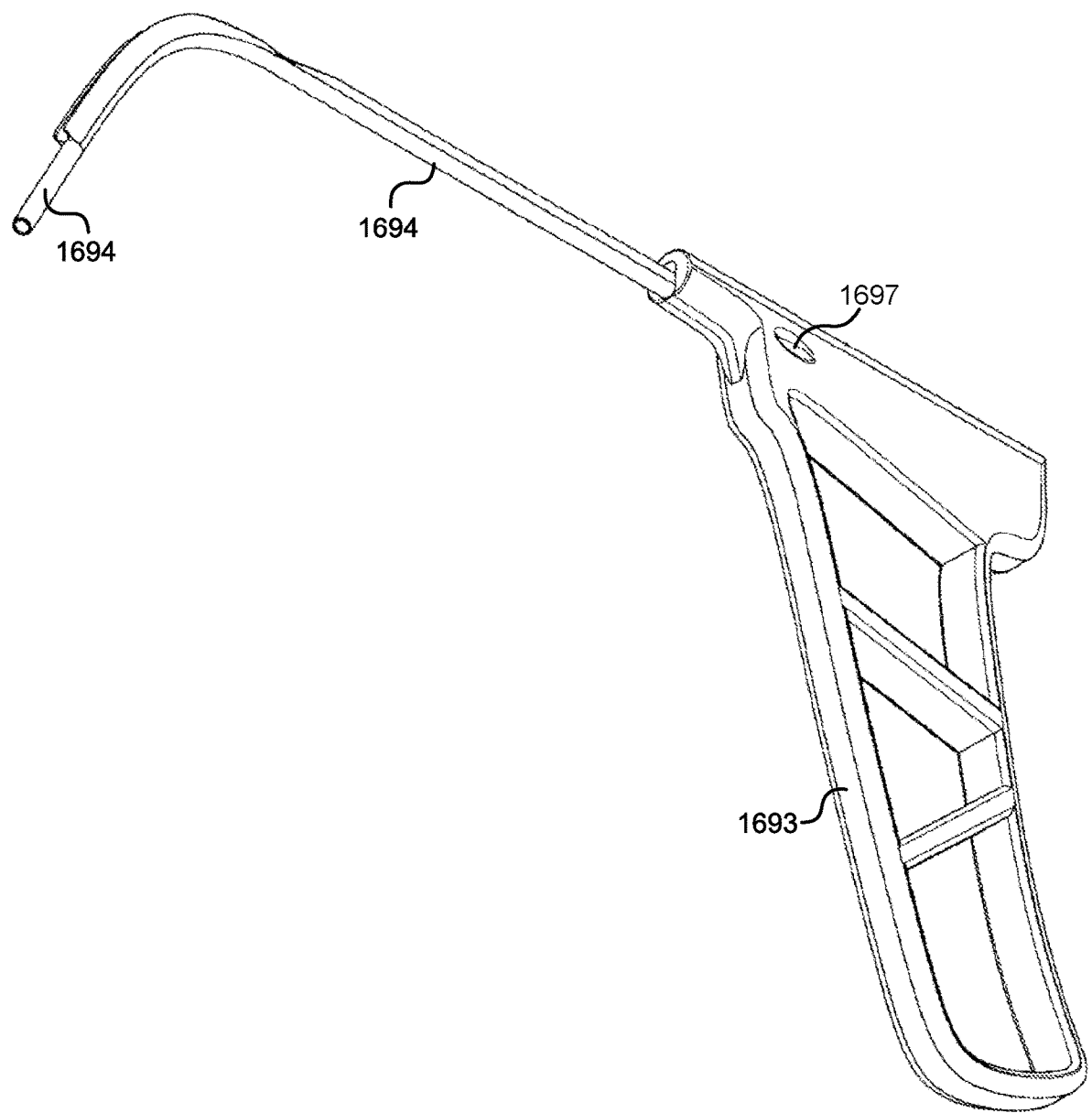
FIG. 56 shows a perspective view of an endoscopic trans-oral esophageal balloon dilator that an endoscope may couple to, in accordance with implementations of the disclosure.
Figure 57:
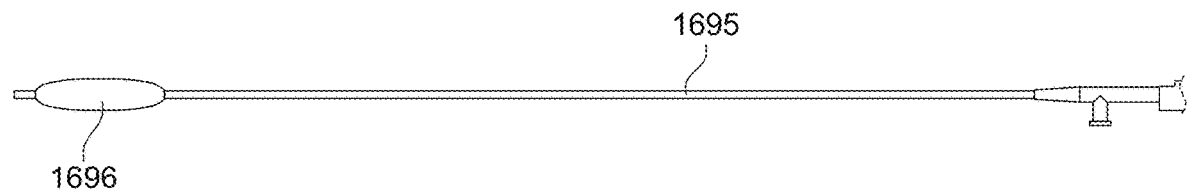
FIG. 57 shows a balloon catheter that may be used with an endoscopic trans-oral esophageal balloon dilator, in accordance with implementations of the disclosure.
Figure 58:
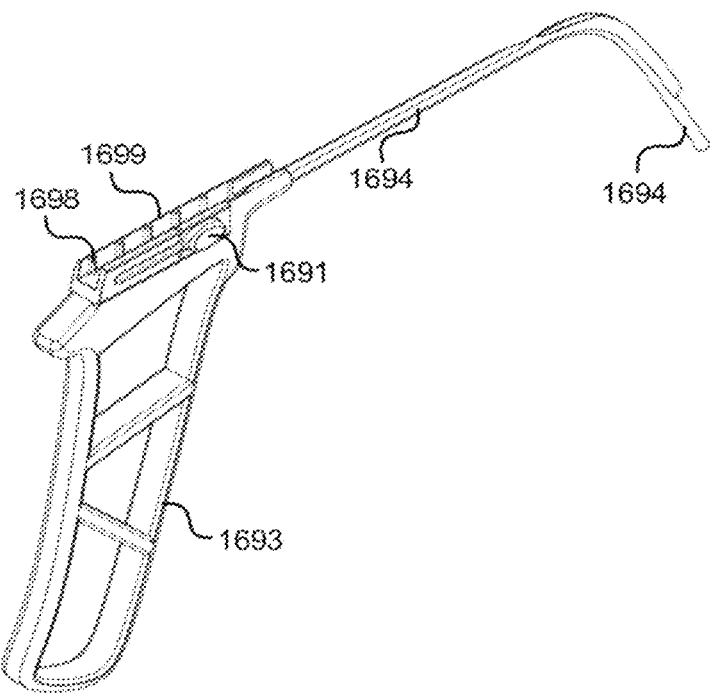
FIG. 58 shows a perspective view of an endoscopic trans-oral esophageal balloon dilator that an endoscope may couple to in accordance with implementations of the disclosure.
Figure 59:
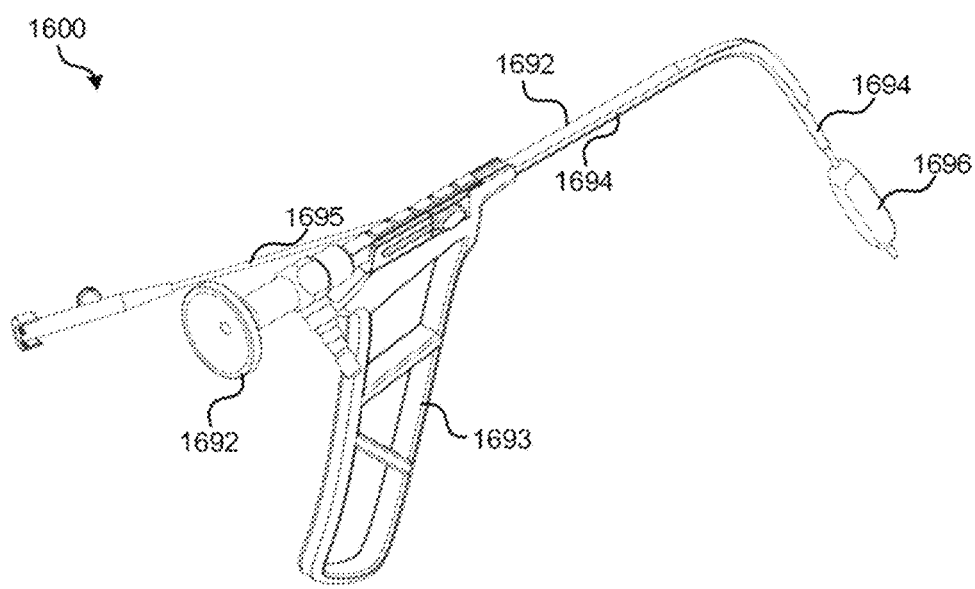
FIG. 59 shows a perspective view of the endoscopic trans-oral esophageal balloon dilator of FIG. 58 with a coupled endoscope, in accordance with implementations of the disclosure.

A dilating tracheostomy tube 1595 for this purpose is illustrated by FIG. 55. The dilating tracheostomy tube 1595 could be used independently or to further dilate the stoma beyond the diameter provided by the first balloon inflation. For example, this may become necessary should a larger diameter #6 or #8 tracheostomy tube be necessary. The dilating tube may have on its shaft two separate balloons—a distal balloon 1580 and a proximal balloon 1581. The distal balloon 1580 may be a low-pressure cuff similar to the cuffed tracheostomy tubes already on the market. This distal balloon/cuff may typically be advanced to a point within the tracheal lumen and then inflated. Similar to standard tracheostomy design, when inflated via the low-pressure inflation port 1588, the distal cuff may serve to protect the airway by creating a seal against the tracheal wall.

The proximal balloon 1581 may be a high-pressure balloon that in its un-inflated state may remain adherent and flush to the tube 1582. When the tube (with the uninflated proximal and distal balloon) is advanced through the recently dilated tracheal stoma, the proximal high-pressure balloon could be inflated via the inflation port 1589 to a larger diameter, thereby increasing the diameter of the tracheal stoma. Once the tracheal stoma is maximally dilated, the proximal balloon 1581 may be deflated, the double balloon tube removed, and a larger diameter, more conventional tracheostomy tube could be inserted in its place. This is referred to as upsizing the tracheostomy tube and may be useful in neonates or patients on chronic ventilator support who have a smaller tracheostomy tube that is not of sufficient size or diameter to provide adequate ventilator support or tracheal/pulmonary hygiene.

Endoscopic Trans-oral Esophageal Balloon Dilator

Patients who have difficulty swallowing secondary to cervical esophageal stricture or chronic cricopharyngeal spasm often require esophageal dilatation. Esophageal dilatation is rarely performed in the office setting and is almost always performed by gastroenterologists under sedative anesthesia. Esophageal dilatation is usually performed at the same time as esophagogastroduodenoscopy (EGD). Although EGD is sometimes necessary, it is not required every time a patient requires dilation. This is especially true for patients requiring multiple dilatations over time as might occur following radiation therapy or chronic laryngopharyngeal reflux. Current techniques for esophageal dilatation may involve serial dilation with progressively sized Bougie catheters and esophageal balloon catheters.

FIGS. 56-61 illustrate implementations of a new endoscopic trans-oral esophageal balloon dilator system in accordance with the disclosure. This system may allow for simple, low cost, safe, and effective cervical balloon esophageal dilatation that could be performed in the office setting, under endoscopic guidance, and without the need for anesthesia or accompanying EGD procedure. Another implementation, not shown, may involve an endoscopic trans-nasal esophageal balloon dilator of similar concept to the trans-oral dilator.

Figure 60:
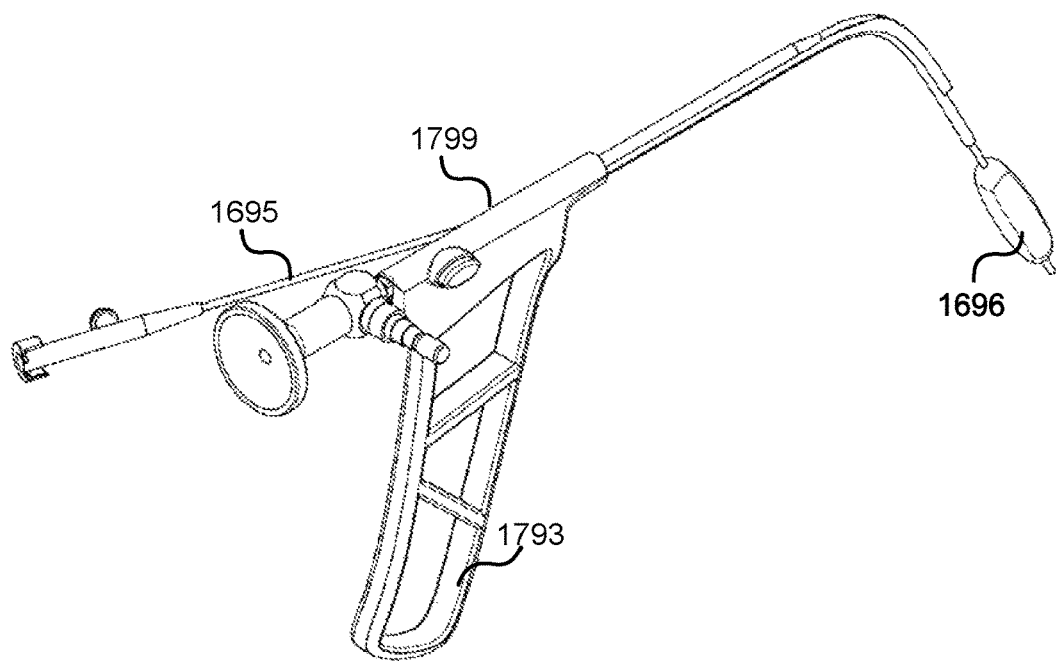
FIG. 60 shows a perspective view of the endoscopic trans-oral esophageal balloon dilator with a coupled endoscope, in accordance with implementations of the disclosure.

With reference to FIGS. 56-59, an endoscopic trans-oral esophageal balloon dilator system 1600 as shown includes a flexible-rigid hybrid endoscope 1692 that is removably coupled to a hand piece 1693. The hand piece 1693 may be disposable or reusable. In the example of FIGS. 56-59, the hand piece 1693 includes a levered top down ratchet attachment mechanism 1699 for receiving a rigid proximal end of an endoscope 1692. Mechanism 1699 may be similar to the levered top down ratchet attachment mechanisms discussed above. For example, mechanism 1699 may include ridges 1698 for receiving slots of a rigid proximal attachment segment of the endoscope, and a lever that is retracted from a groove of the endoscope by pressing button 1691. FIGS. 60-61 illustrate another example attachment mechanism—an insert ratchet mechanism 1799—that may be used to removably couple a hand piece 1793 of an endoscopic trans-oral esophageal balloon dilator system to a rigid proximal end of an endoscope. Mechanism 1799 may be similar to the insert ratchet attachment mechanisms discussed above. In other implementations, other attachment mechanisms may be used to removably couple a flexible-rigid hybrid endoscope in accordance with the disclosure to the endoscopic trans-oral esophageal balloon dilator system.

Figure 46:
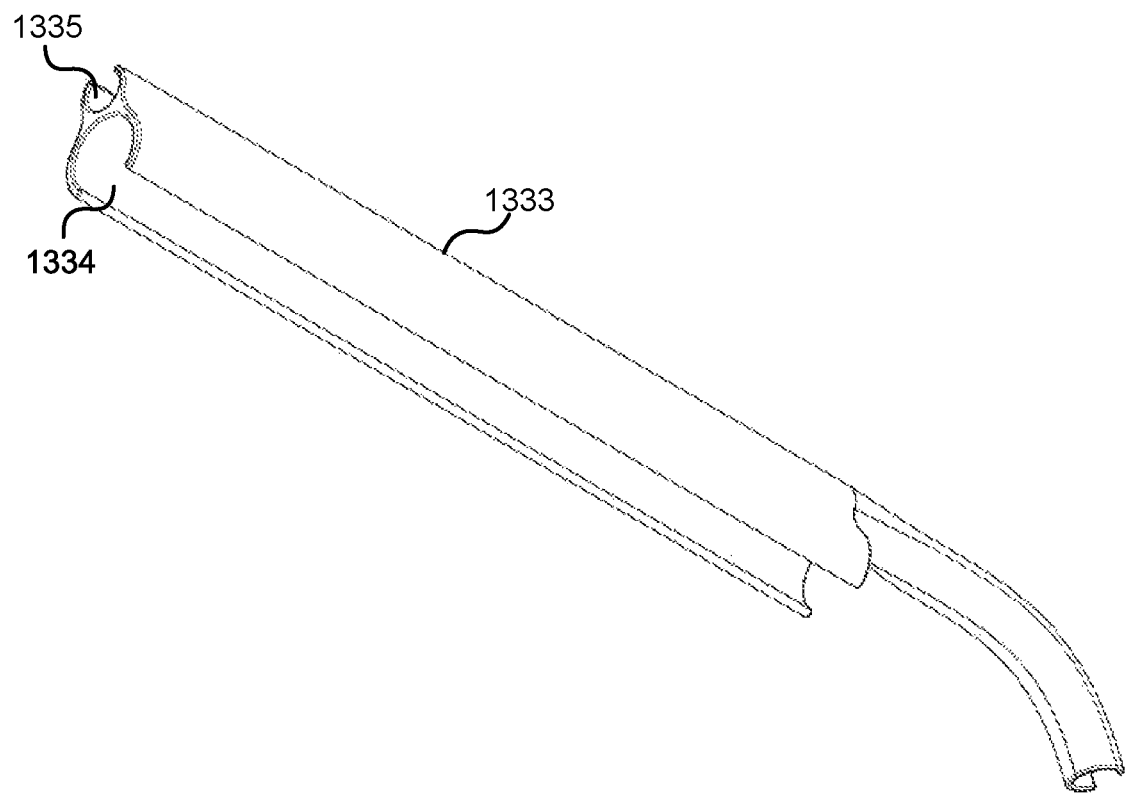
FIG. 46 shows a perspective view of a removable insert that may be used to couple an endoscope to a distal end of an instrument, in accordance with implementations of the disclosure.
Figure 47:
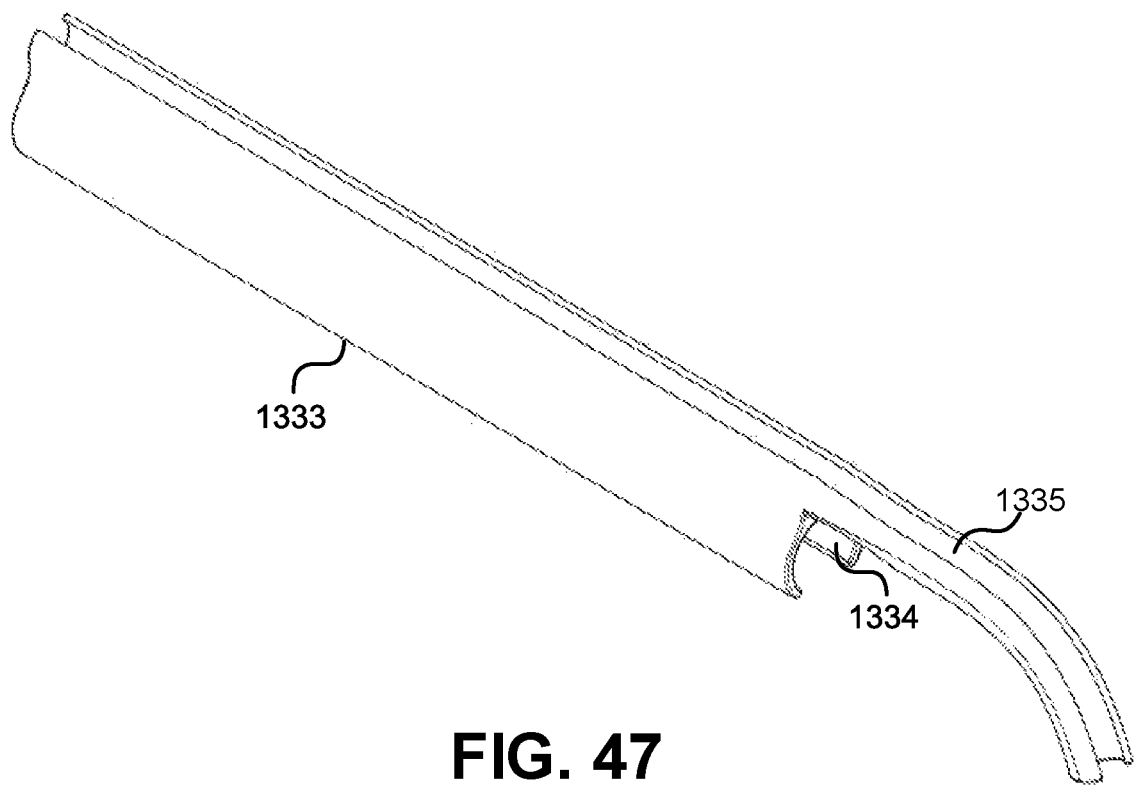
FIG. 47 shows another perspective view of the removable insert of FIG. 46.
Figure 49:
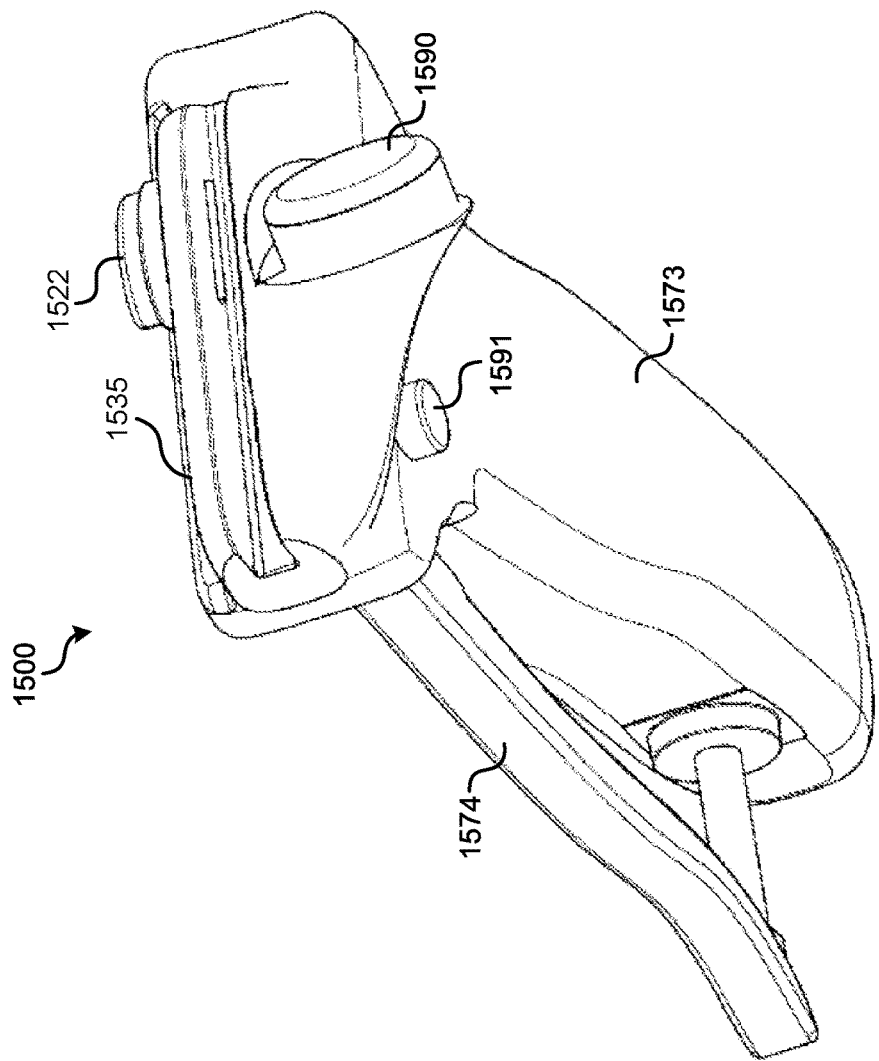
FIG. 49 shows another perspective view of the balloon hand pump of FIG. 48.
Figure 48:
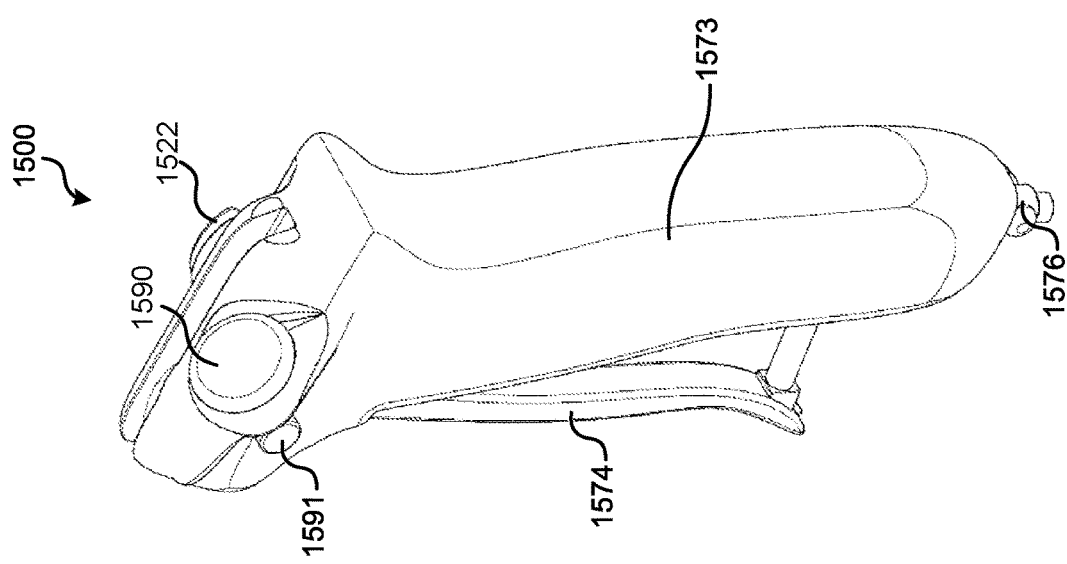
FIG. 48 shows a perspective view of a balloon hand pump to be used during endoscopic tracheal, sinus, or esophageal balloon dilation, in accordance with implementations of the disclosure.
Figure 50:
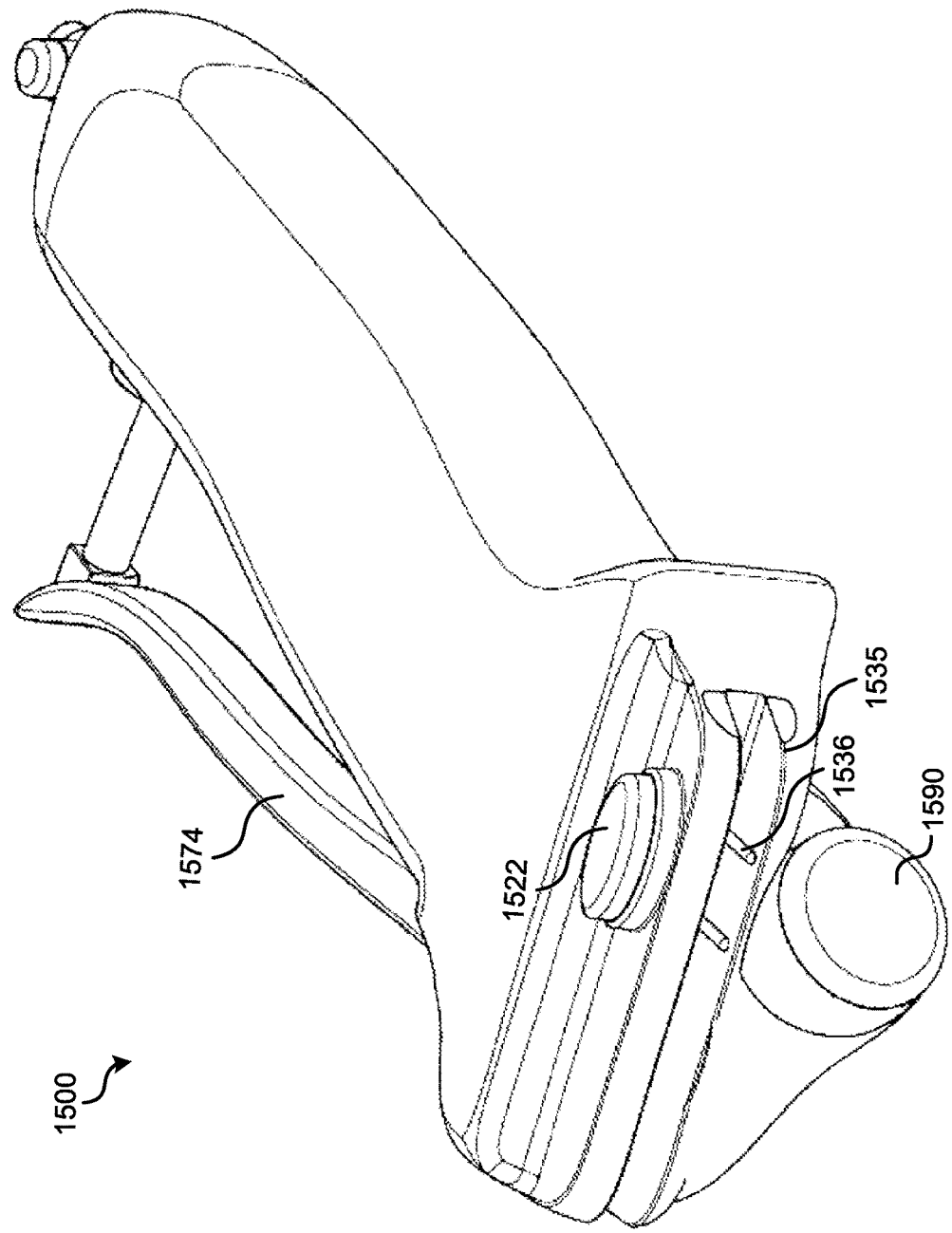
FIG. 50 shows another perspective view of the balloon hand pump of FIG. 48.
Figure 51:
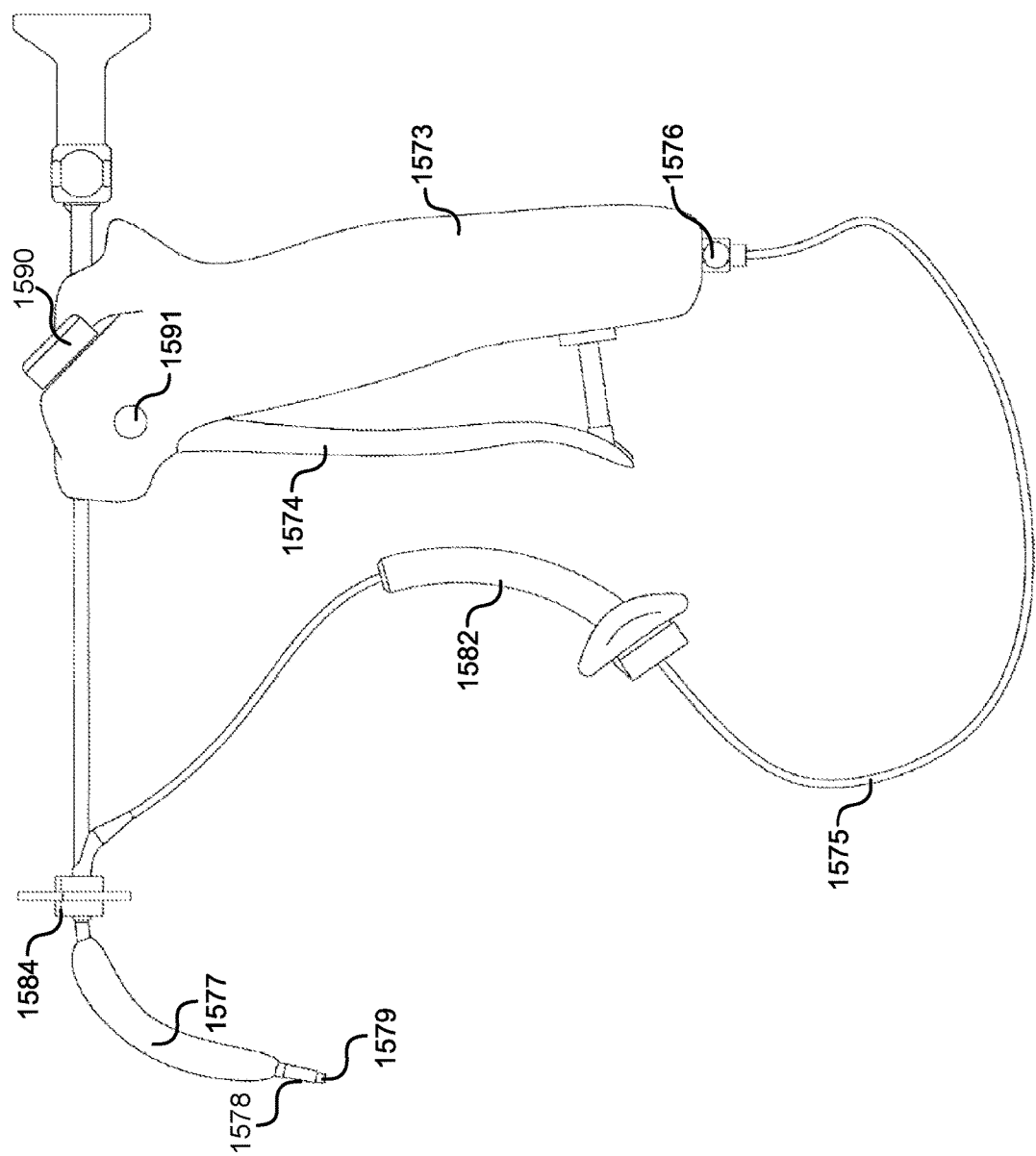
FIG. 51 shows a side view of the balloon hand pump of FIG. 48, including a coupled endoscope and tracheal balloon dilation assembly.
Figure 52:
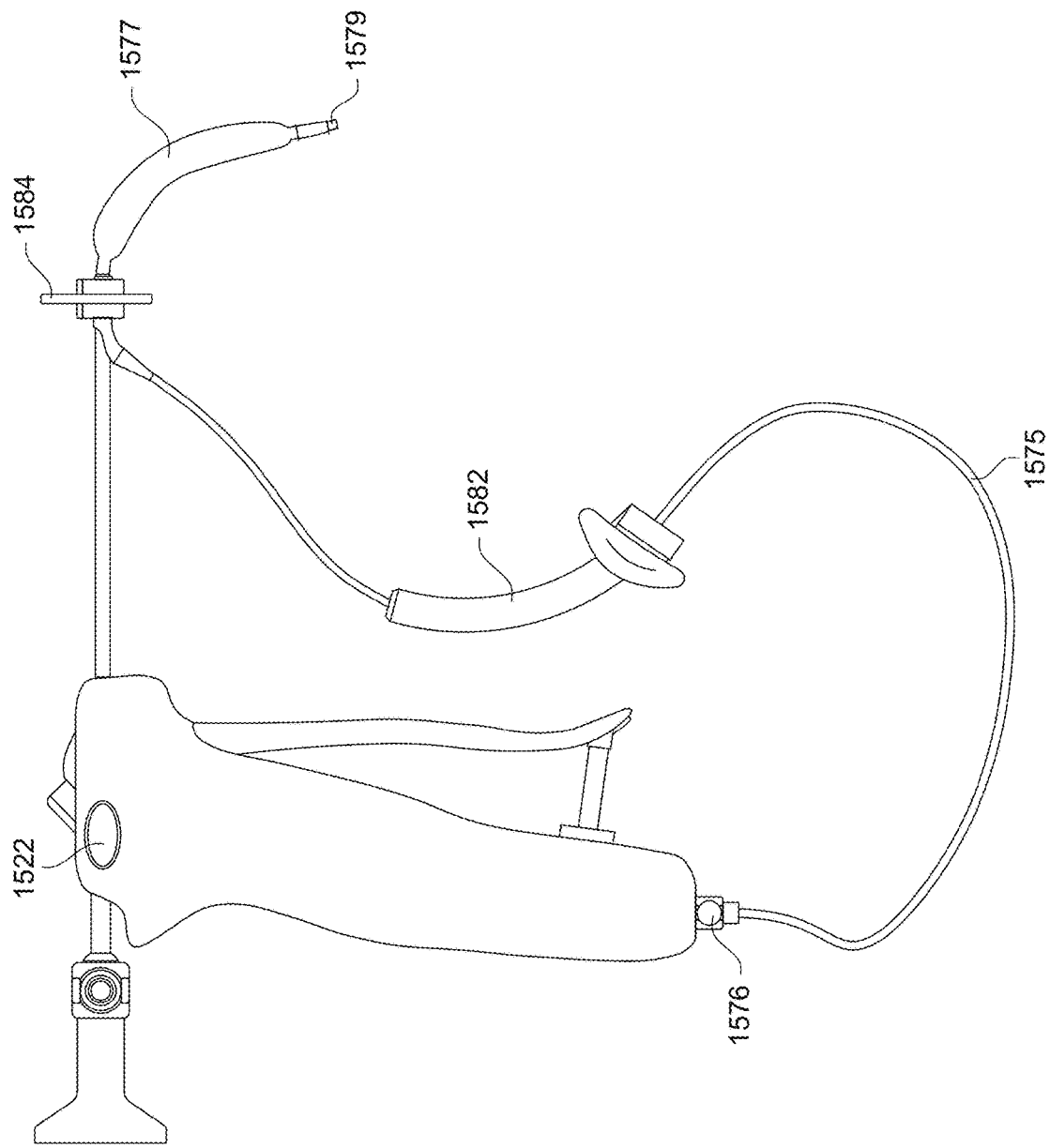
FIG. 52 shows a side view of the balloon hand pump of FIG. 48, including a coupled endoscope and balloon dilation assembly.
Figure 53:
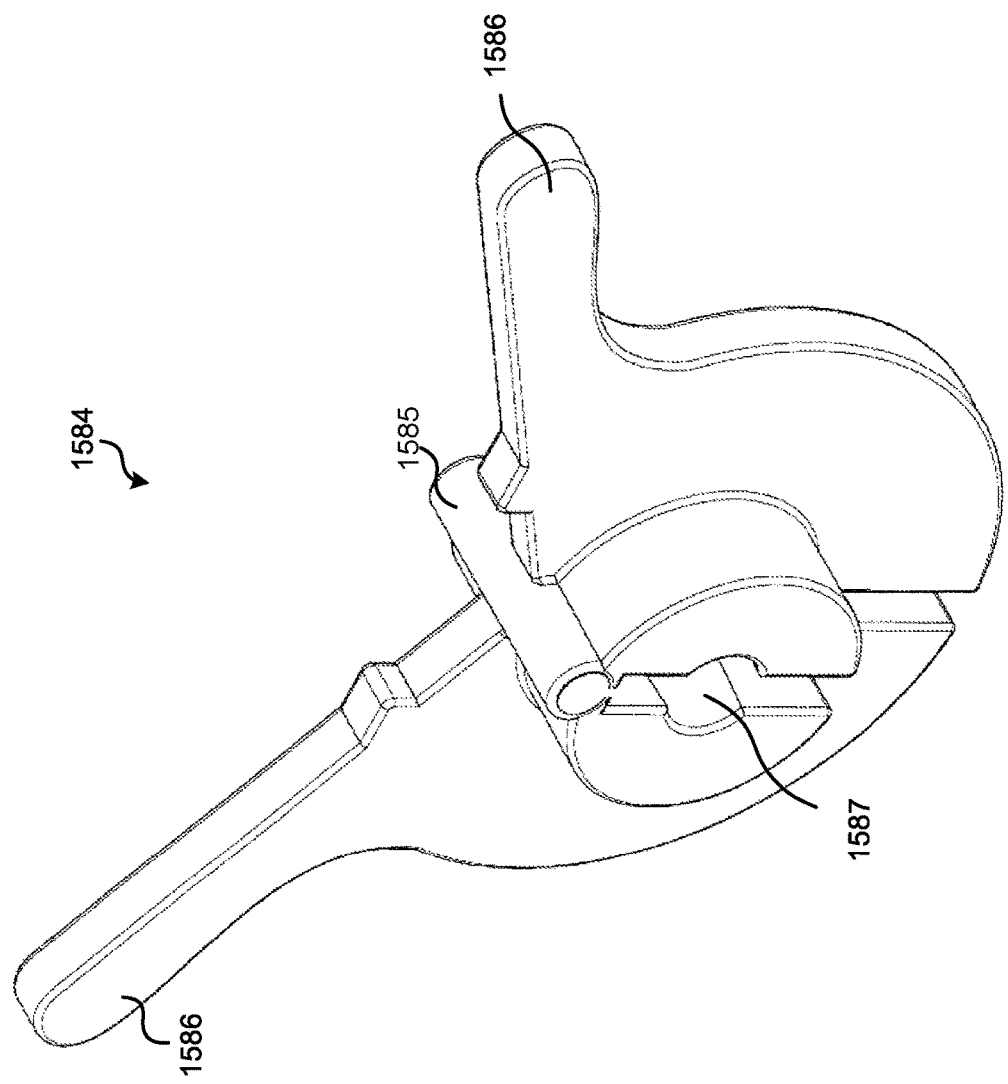
FIG. 53 shows a stopper that may be used with an endoscopic tracheal dilator in accordance with implementations of the disclosure.
Figure 54:
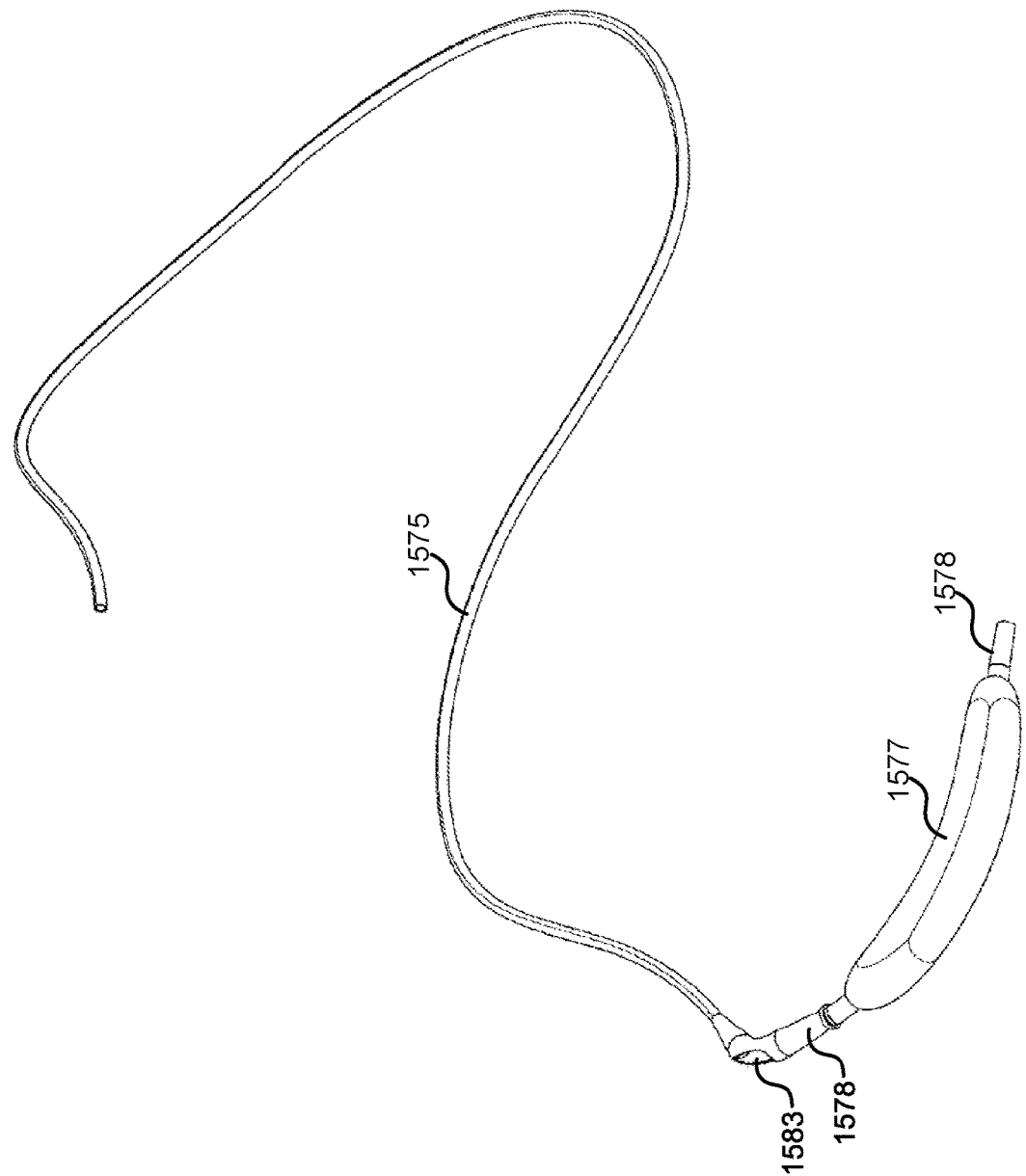
FIG. 54 shows a balloon dilator assembly, in accordance with implementations of the disclosure.

Extending from the hand piece 1693 may be a hollow tube 1694 which could be rigid, malleable, or flexible. The hollow tube 1694 may be of adequate caliber to internally accommodate a thin, flexible balloon catheter 1695. The flexible balloon catheter 1695 may have on its distal end an inflatable balloon 1696. In its non-inflated state, the balloon could be advanced through a hole 1697 on the side of the hand piece. The flexible balloon catheter may be of sufficient length to allow extension of the balloon beyond the distal end of the hollow tube. The flexible end of the hybrid endoscope may be attached to the curved aspect of the hollow tube 1694 by a removable, firm or flexible, insert as depicted in FIGS. 46-47. The endoscope may be used to visualize the balloon 1696 and balloon catheter 1695 as it passes from the distal end of the hollow tube into the cervical esophagus. A small marking on the catheter proximal to the balloon may be used to help endoscopically approximate the proper distance to insert the catheter into the esophagus prior to balloon inflation. The tracheal balloon pump hand piece as depicted in FIGS. 48-52 could also be adapted for use with the esophageal dilator and may facilitate one handed operation.

Figure 72:
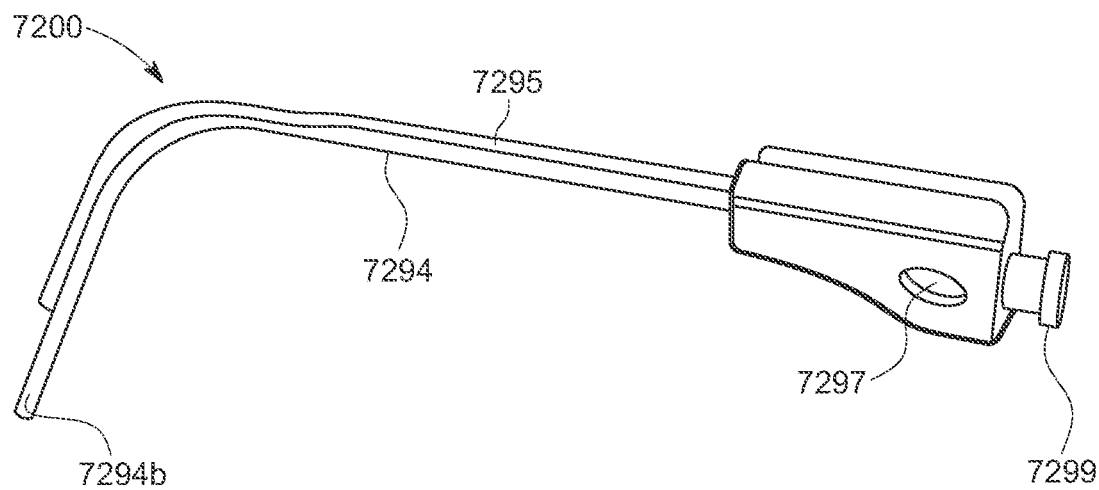
FIG. 72 illustrates a cannula of a balloon dilator system, in accordance with implementations.
Figure 73:
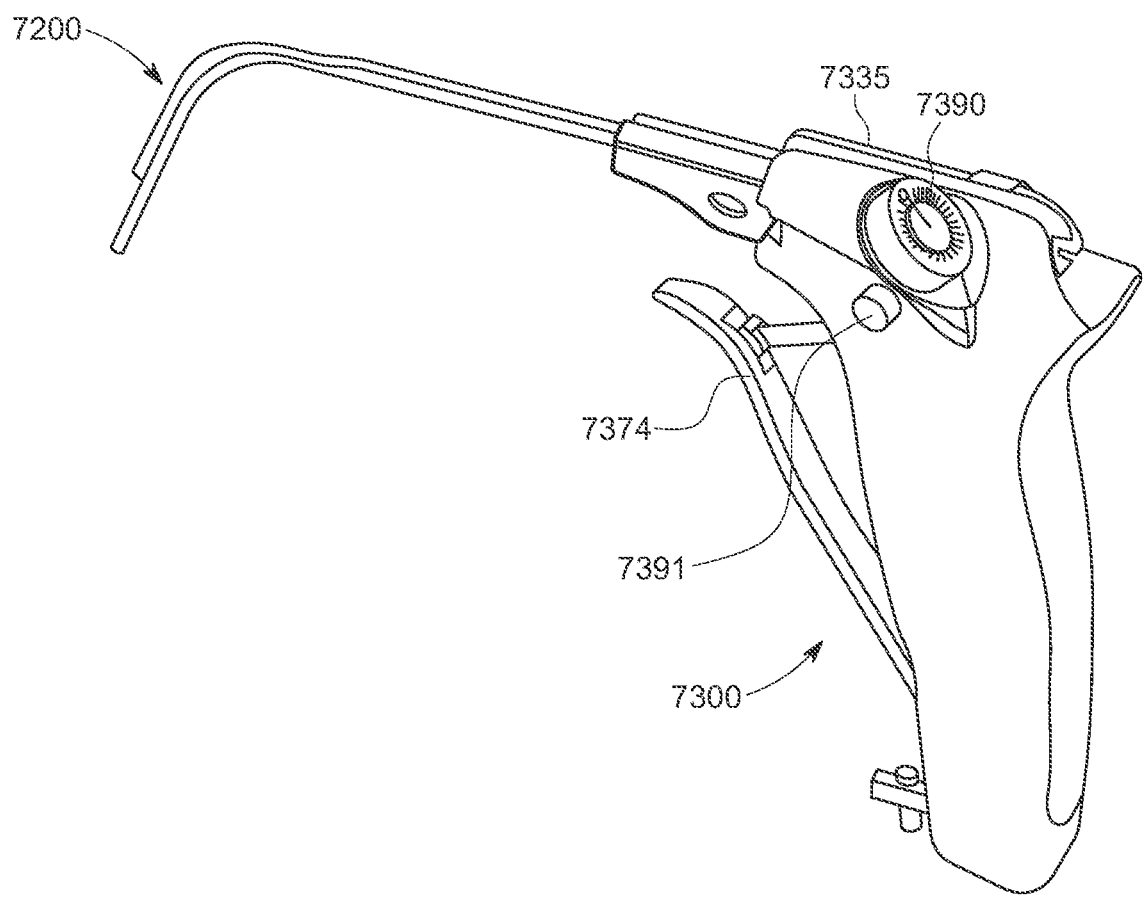
FIG. 73 illustrates a balloon pump hand piece of a balloon dilator system, in accordance with implementations.

FIGS. 72-73 illustrate another example balloon dilator system, in accordance with implementations of the disclosure. The balloon dilator system includes a cannula 7200 and a balloon pump hand piece 7300. The system may be utilized in endoscopic applications that require dilation of a human cavity, such as sinus, tracheal, or esophageal applications. For example, the system may function as an esophageal dilator as discussed above with reference to FIGS. 56-59, or as a tracheal dilator as discussed above with reference to FIGS. 48-55. The system may be used in trans-nasal or transoral procedures.

The cannula 7200 includes a proximal end including a connector 7299 configured to removably couple to a top portion of hand piece 7300. The removable connection may be made via press fitting, snap fitting, friction fitting, magnetic coupling, clamps, threaded turns, or some other suitable mechanism. By virtue of a removable connection, the cannula may be disposed of after a procedure. Alternatively, the distal end of cannula 7200 may be integrated into hand piece 7300.

The cannula includes a hollow tube 7294 that may be rigid, malleable, or flexible. The hollow tube 7294 may be of adequate caliber to internally accommodate a thin, flexible balloon catheter (e.g., thin, flexible balloon catheter 1695). The flexible balloon catheter 1695 may have on its distal end an inflatable balloon (e.g., inflatable balloon 1696). When the balloon is in a non-inflated state, the balloon catheter may be threaded through hollow tube 7294 by first advancing it through a hole 7297 on the side of the proximal end of cannula 7200. Alternatively the hole may be placed in some other suitable location on cannula 7200. The hole 7297 may connect to a proximal end of a hollow tube 7294. Alternatively, the balloon catheter may be advanced through a hole on the side of or back of hand piece 7300 (not illustrated in this embodiment) that connects to hollow tube 7294. The flexible balloon catheter may be of sufficient length to allow extension of the balloon beyond the distal end 7294*b* of the hollow tube 7294.

As further depicted, cannula 7200 includes a channel 7295 for guiding and/or removably coupling to a shaft of an endoscope. The channel 7295 may run parallel to hollow tube 7294, and it may be open or closed. The channel 7295 may couple to the distal end of the shaft of the endoscope.

Referring to FIG. 73, the balloon pump hand piece 7300 includes a pump handle 7374 that, when actuated, pumps air or liquid (e.g., water or saline) through a flexible tube (not shown) that couples on one end to a connection of the balloon pump hand piece 7300 and on the other end to the balloon catheter. Alternatively, the flexible tube may be a component of the balloon catheter that couples to the balloon pump hand piece. The connection may be made at the base of the hand piece 7300 or some other convenient or ergonomic location. Pressurized fluid (e.g., air or liquid) may then be transmitted from the pump handle connection through the flexible tube to the distal balloon of the balloon catheter. Pressure may be measured by a pressure gauge 7390 incorporated into the balloon pump hand piece 7300. The balloon pump hand piece 7300 also includes a button 7391 that, when actuated, may release the pressure from the balloon.

The pressurized fluid may be stored in a chamber incorporated into the balloon pump hand piece 7300. The chamber may be removable or refillable via a port (not shown). In some implementations, the chamber is a fluid syringe that may snap into the body of the handle, or the syringe may be part of the handle.

Balloon pump hand piece 7300 also includes an endoscope attachment mechanism incorporated into its top side. The attachment mechanism includes a channel 7335 for receiving a proximal end of a shaft of the endoscope. Although depicted as open in this example, the channel may be closed. The channel may incorporate any suitable mechanism, (e.g., levered top down ratchet mechanism) including the mechanisms discussed above, for removably coupling the endoscope.

While the endoscopes, attachment mechanisms, and instruments described herein have generally been described with respect to Otorhinolaryngologic (Ear, nose, and throat, ENT) surgical applications, it should be noted that endoscopes disclosed herein need not be limited these applications. For example, the endoscopes described herein could be utilized in other surgical and medical specialties such as general surgery, gastroenterology, pulmonology, urology, plastic surgery, neurosurgery, and orthopedics for applications such as surgical stapling. Commercial, non-surgical, applications for the technology disclosed herein are also applicable.

In this document, the terms "machine readable medium," "computer readable medium," and similar terms are used to generally refer to non-transitory mediums, volatile or non-volatile, that store data and/or instructions that cause a machine to operate in a specific fashion. Common forms of machine-readable media include, for example, a hard disk, solid state drive, magnetic tape, or any other magnetic data storage medium, an optical disc or any other optical data storage medium, any physical medium with patterns of holes, a RAM, a PROM, EPROM, a FLASH-EPROM, NVRAM, any other memory chip or cartridge, and networked versions of the same.

These and other various forms of computer readable media may be involved in carrying one or more sequences of one or more instructions to a processing device for execution. Such instructions embodied on the medium, are generally referred to as "instructions" or "code." Instructions may be grouped in the form of computer programs or other groupings. When executed, such instructions may enable a processing device to perform features or functions of the present application as discussed herein.

In this document, a "processing device" may be implemented as a single processor that performs processing operations or a combination of specialized and/or general-purpose processors that perform processing operations. A processing device may include a CPU, GPU, APU, DSP, FPGA, ASIC, SOC, and/or other processing circuitry.

Although described above in terms of various example implementations and implementations, it should be understood that the various features, aspects and functionality described in one or more of the individual implementations are not limited in their applicability to the particular implementation with which they are described, but instead can be applied, alone or in various combinations, to one or more of the other implementations of the application, whether or not such implementations are described and whether or not such features are presented as being a part of a described implementation. Thus, the breadth and scope of the present application should not be limited by any of the above-described example implementations.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

To the extent applicable, the terms "first," "second," "third," etc. herein are merely employed to show the respective objects described by these terms as separate entities and are not meant to connote a sense of chronological order, unless stated explicitly otherwise herein.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide some instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various implementations set forth herein are described in terms of example block diagrams, flow charts and other illustrations. As will become apparent to one of ordinary skill in the art after reading this document, the illustrated implementations and their various alternatives can be implemented without confinement to the illustrated examples. For example, block diagrams and their accompanying description should not be construed as mandating a particular architecture or configuration.

While various implementations of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various implementations be implemented to perform the recited functionality in the same order unless the context dictates otherwise.

What is claimed is:

1. A balloon dilator system, comprising:
a balloon pump hand piece configured to pump pressurized fluid through a flexible tube to inflate a high-pressure, inflatable balloon, the balloon pump hand piece configured to removably couple to a proximal end of an endoscope;
the flexible tube, wherein the flexible tube is configured to be in fluid communication with the balloon pump hand piece at a first end of the flexible tube, and the high-pressure, inflatable balloon at a second end of the flexible tube;
a cannula having a hollow interior, the cannula separated from the balloon pump hand piece, the cannula comprising a first opening at its proximal end and a second opening at its distal end, the first opening configured to receive a flexible distal end of the endoscope that is advanced until a tip of the flexible distal end of the endoscope exits the second opening of the cannula; and
the high-pressure, inflatable balloon, wherein the high-pressure, inflatable balloon is external to and circumferentially attached to the cannula between the proximal end of the cannula and the distal end of the cannula, wherein the high-pressure, inflatable balloon is configured to be positioned within and dilate a tracheal stoma of a patient, and the patient can breathe through the cannula when the endoscope is not inserted into the cannula and while the high-pressure, inflatable balloon is being inflated.

2. The balloon dilator system of claim 1, wherein the balloon pump hand piece further comprises: a pressure gauge configured to measure pressure of the pressurized fluid that is pumped to inflate the inflatable balloon; and a control that, when actuated, releases pressure and deflates the inflatable balloon.

3. The balloon dilator system of claim 1, wherein the balloon pump hand piece further comprises a pump handle that, when actuated, pumps the pressurized fluid through the flexible tube.

4. The balloon dilator system of claim 1, wherein the balloon pump hand piece further comprises a connection at a base of the balloon pump hand piece, the connection configured to fluidically couple to the first end of the flexible tube.

5. The balloon dilator system of claim 1, further comprising: a removable stopper configured to be placed on the cannula proximal to the high-pressure, inflatable balloon to stabilize the balloon dilator system during inflation of the high-pressure, inflatable balloon.

6. The balloon dilator system of claim 5, wherein the removable stopper comprises a spring and lateral projections that are squeezable to activate the spring and release the stopper.

7. The balloon dilator system of claim 1, further comprising: a tracheostomy tube configured to slide over the flexible tube and the cannula.

8. The balloon dilator system of claim 7, wherein the tracheostomy tube comprises:
a first inflation port;
a second inflation port; and
a shaft comprising a distal balloon configured to be inflated via the first inflation port, and a proximal balloon configured to be inflated via the second inflation port to a higher pressure than the distal balloon is inflated via the first inflation port.

9. The balloon dilator system of claim 8, wherein:
the distal balloon is configured to be advanced within a tracheal lumen of a patient and inflated via the first inflation port; and
the proximal balloon is configured to be advanced within a tracheal stoma of the patient and inflated via the second inflation port to dilate the tracheal stoma.

10. The balloon dilator system of claim 1, wherein the balloon pump hand piece comprises a levered top down ratchet attachment mechanism for removably coupling the balloon pump hand piece to the proximal end of an endoscope.

11. The balloon dilator system of claim 1, wherein the pressurized fluid is a liquid.

12. The balloon dilator system of claim 1, wherein the pressurized fluid is air.

13. A balloon dilator system, comprising:
a flexible tube configured to be in fluid communication with a fluid pump at a first end of the flexible tube, and a high-pressure, elongate inflatable balloon at a second end of the flexible tube;
a cannula having a hollow interior, the cannula coupled to the flexible tube, the cannula comprising a first opening at its proximal end and a second opening at its distal end, the first opening configured to receive a distal end of an endoscope that is advanced until a tip of the distal end of the endoscope exits the second opening of the cannula; and
the high-pressure, elongate inflatable balloon, wherein the high-pressure elongate inflatable balloon is external to and circumferentially attached to the cannula between the proximal end of the cannula and the distal end of the cannula, wherein the high-pressure, elongate inflatable balloon is configured to be positioned within and dilate a tracheal stoma of a patient, and the patient can breathe through the cannula when the endoscope is not inserted into the cannula and while the high-pressure, elongate inflatable balloon is being inflated.

14. The endoscopic tracheal balloon dilator system of claim 13, further comprising: a tracheostomy tube configured to slide over the flexible tube and the cannula.

15. The balloon dilator system of claim 10, wherein the levered top down ratchet attachment mechanism is integrated on a top side of the balloon pump hand piece and comprises a housing with an elongated open channel to removably couple the endoscope in a top-down manner.

16. The balloon dilator system of claim 15, wherein the housing comprises:
spaced ridges for receiving respective transverse slots of a rigid proximal attachment segment of the endoscope; and
a retractable interior protuberance located on an interior side surface of the elongated open channel for engaging a longitudinal groove of the rigid proximal attachment segment of the endoscope.

17. The balloon dilator system of claim 1, wherein the balloon pump hand piece comprises an insert ratchet attachment mechanism for removably coupling the balloon pump hand piece to the proximal end of the endoscope, the insert ratchet attachment mechanism integrated on a top side of the balloon pump hand piece.

18. The balloon dilator system of claim 17, wherein the insert ratchet attachment mechanism comprises an external housing with a channel including opening and exit apertures through which the endoscope can be inserted, the housing including a retractable interior protuberance configured to engage a transverse slot of the endoscope to secure the endoscope in place, the retractable interior protuberance configured to be actuated by an external housing button.

19. A balloon dilator system, comprising:
- a balloon pump hand piece configured to pump a pressurized fluid through a flexible tube to inflate a high-pressure, inflatable balloon, the balloon pump hand piece comprising: an attachment mechanism for removably coupling the balloon pump hand piece to a proximal end of an endoscope;
- the flexible tube, wherein the flexible tube is configured to be in fluid communication with the balloon pump hand piece at a first end of the flexible tube, and the high-pressure, inflatable balloon at a second end of the flexible tube;
- a cannula having a hollow interior, the cannula separated from the balloon pump hand piece, the cannula comprising a first opening at its proximal end and a second opening at its distal end, the first opening configured to receive a flexible distal end of the endoscope that is advanced until a tip of the flexible distal end of the endoscope exits the second opening of the cannula;
- the high-pressure, inflatable balloon, wherein the high-pressure, inflatable balloon is external to circumferentially attached to the cannula between the proximal end of the cannula and the distal end of the cannula; and
- a tracheostomy tube configured to slide over the flexible tube and cannula, the tracheostomy tube comprising: a first inflation port, a second inflation port, and a shaft comprising a distal balloon configured to be inflated via the first inflation port, and a proximal balloon configured to be inflated via the second inflation port to a higher pressure than the distal balloon is inflated via the first inflation port.

\* \* \* \* \*